(12) United States Patent
Raj et al.

(10) Patent No.: US 12,215,367 B2
(45) Date of Patent: Feb. 4, 2025

(54) LACTASE ENZYMES WITH IMPROVED PROPERTIES

(71) Applicant: Kerry Group Services International Ltd, Tralee (IE)

(72) Inventors: Hans Raj, Hoersholm (DK); Pernille Smith, Broenshoej (DK); Thomas Eckhardt, Birkeroed (DK); Vojislav Vojinovic, Graested (DK); Charlotte Elisabeth Grüner Schöller, Virum (DK); Johannes Maarten van den Brink, Herlev (DK)

(73) Assignee: Kerry Group Services International Ltd, Tralee (IE)

( * ) Notice: Subject to any disclaimer, the term of this patent is extended or adjusted under 35 U.S.C. 154(b) by 0 days.

(21) Appl. No.: 17/986,618

(22) Filed: Nov. 14, 2022

(65) Prior Publication Data
US 2023/0235307 A1    Jul. 27, 2023

Related U.S. Application Data

(63) Continuation of application No. 16/604,129, filed as application No. PCT/EP2018/059250 on Apr. 11, 2018, now Pat. No. 11,525,129.

(30) Foreign Application Priority Data

Apr. 11, 2017   (EP) .................... 17166021

(51) Int. Cl.
  *C12N 9/38*   (2006.01)
  *A23L 29/00*  (2016.01)
(52) U.S. Cl.
  CPC ............ *C12N 9/2471* (2013.01); *A23L 29/06* (2016.08)
(58) Field of Classification Search
  CPC ................. C12N 9/2471; A23L 29/06; C12Y 302/01023; C07K 14/195
  See application file for complete search history.

(56) References Cited

U.S. PATENT DOCUMENTS

| | | | |
|---|---|---|---|
| 8,030,049 B2 * | 10/2011 | Tzortzis | C12Y 302/01023 435/71.1 |
| 10,058,107 B2 | 8/2018 | Hendriksen et al. | |
| 10,306,902 B2 | 6/2019 | Hendriksen et al. | |
| 10,555,541 B2 | 2/2020 | Hendriksen et al. | |
| 2009/0110770 A1 | 4/2009 | Tzortzis et al. | |
| 2009/0117080 A1 | 5/2009 | Tzortzis et al. | |
| 2009/0297660 A1 | 12/2009 | Silver et al. | |
| 2010/0113383 A1 | 5/2010 | Mills et al. | |
| 2010/0285175 A1 | 11/2010 | Hendriksen et al. | |
| 2012/0058223 A1 | 3/2012 | Stougaard et al. | |
| 2016/0333331 A1 | 11/2016 | De Jong et al. | |
| 2017/0215449 A1 | 8/2017 | Nagahata et al. | |
| 2019/0343138 A1 | 11/2019 | Ba et al. | |
| 2020/0120946 A1 | 4/2020 | Hendriksen et al. | |
| 2020/0123519 A1 | 4/2020 | Bongiorni et al. | |
| 2021/0032615 A1 | 2/2021 | Raj et al. | |
| 2021/0037844 A1 | 2/2021 | Hendriksen et al. | |
| 2021/0348147 A1 | 11/2021 | Raj et al. | |
| 2023/0076578 A1 | 3/2023 | Raj et al. | |
| 2023/0210121 A1 | 7/2023 | Raj et al. | |

FOREIGN PATENT DOCUMENTS

| | | |
|---|---|---|
| CN | 103431042 B | 1/2015 |
| EP | 1 227 152 A1 | 7/2002 |
| EP | 2 530 148 A1 | 12/2012 |
| EP | 2 957 180 B1 | 12/2015 |
| RU | 2278160 C2 | 9/2005 |
| RU | 2009120742 | 12/2010 |
| WO | WO-2005/084411 A2 | 9/2005 |
| WO | WO-2005/086794 A2 | 9/2005 |
| WO | WO-2007/088324 A1 | 8/2007 |
| WO | WO-2007/110619 A1 | 10/2007 |
| WO | WO-2008/033520 A2 | 3/2008 |
| WO | WO-2009/009142 A2 | 1/2009 |
| WO | WO-2009/071539 A1 | 6/2009 |
| WO | WO-2010/092057 A1 | 8/2010 |
| WO | WO-2013/160413 A1 | 10/2013 |
| WO | WO-2015/107050 A1 | 7/2015 |
| WO | WO-2017/216000 A1 | 12/2017 |
| WO | WO-2018/041869 A1 | 3/2018 |
| WO | WO-2018/130630 A1 | 7/2018 |
| WO | WO-2018/187524 A1 | 10/2018 |
| WO | WO-2018/189238 A1 | 10/2018 |
| WO | WO-2018/189242 A1 | 10/2018 |

OTHER PUBLICATIONS

Odamaki et al., Comparative Genomics Revealed Genetic Diversity and Species/Strain-Level Differences in Carbohydrate Metabolism of Three Probiotic Bifidobacterial Species. Int. J. Genomics., 2015, Article ID 567809, 12 pages (Year: 2015).*

"Beta-galactosidase [*Bifidobacterium angulatum*]"; NCBI Reference Sequence: WP_033508907.1; NCBI; https://www.ncbi.nlm.nih.gov/protein/WP_033508907.1?report=genbank&log$=prottop&blast_rank=1&RID=STY73TRP013; Nov. 7, 2014; 1 page.

"Beta-galactosidase [*Bifidobacterium bifidum*]"; NCBI Reference Sequence: ALE11829.1; NCBI; https://www.ncbi.nlm.nih.gov/protein/ALE11829.1?report=genbank&log$=prottop&blast_rank=1&RID=STXB9JWN016; Sep. 14, 2015; 2 pages.

"Beta-galactosidase [*Bifidobacterium longum*]"; NCBI Reference Sequence: WP_013582379.1; NCBI; https://www.ncbi.nlm.nih.gov/protein/WP_013582379.1?report=genbank&log$=prottop&blast_rank=1&RID=STXT9S92016; May 18, 2013; 1 page.

(Continued)

*Primary Examiner* — Ganapathirama Raghu
(74) *Attorney, Agent, or Firm* — Foley & Lardner LLP

(57) ABSTRACT

Disclosed are peptides exhibiting betagalactosidase enzyme activity as well as dairy products comprising them and related methods for reducing the lactose content in compositions, such as dairy products.

18 Claims, 16 Drawing Sheets

Figure 1:
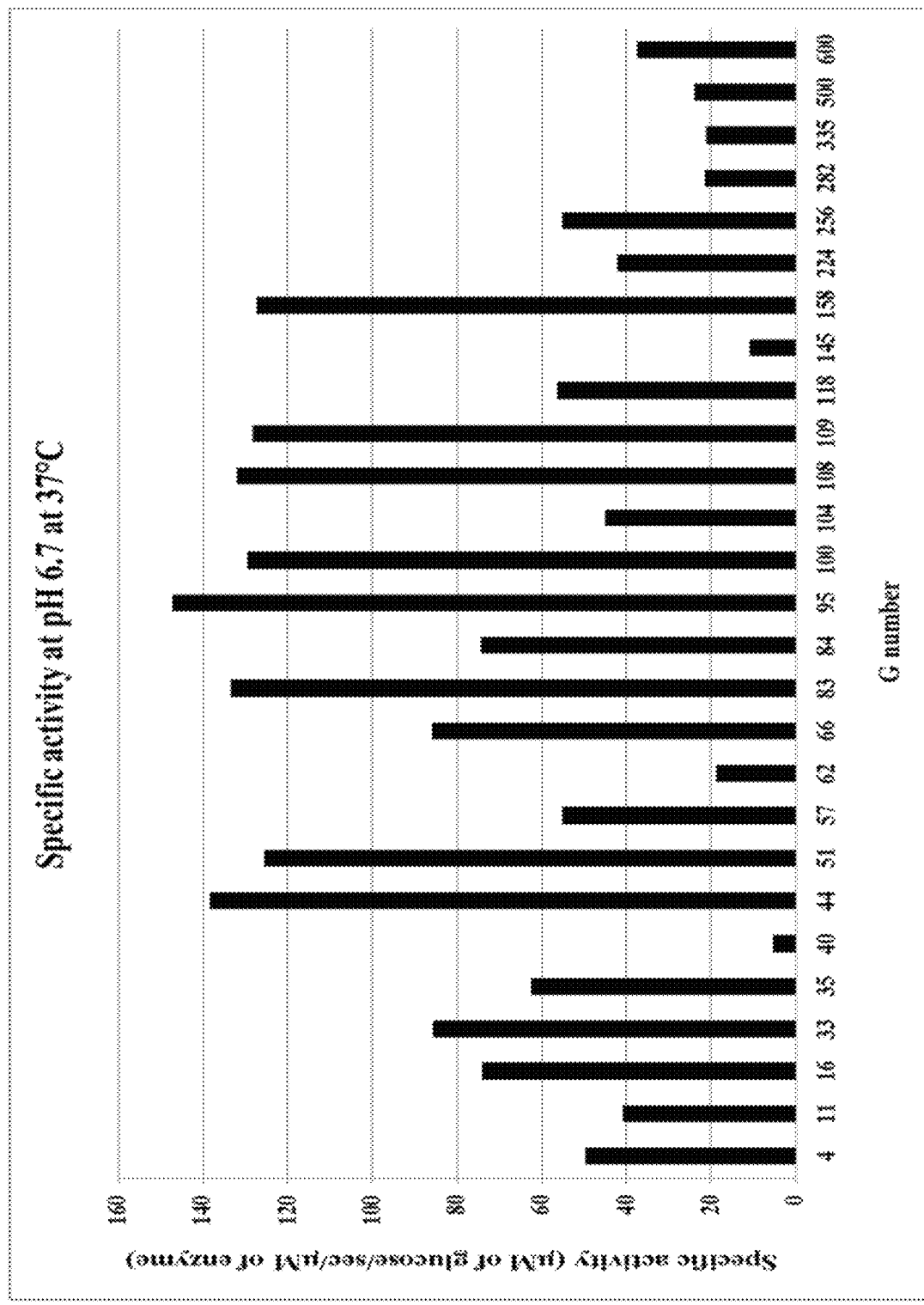

Specification includes a Sequence Listing.

(56) References Cited

OTHER PUBLICATIONS

"Beta-galactosidase [*Lactobacillus amylovorus*]"; NCBI Reference Sequence: WP_013438360.1; NCBI; https://www.ncbi.nlm.nih.gov/protein/WP_013438360.1?report=genbank&log$=prottop&blast_rank=1&RID=STWKFN82013; May 18, 2013; 1 page.
"Beta-galactosidase [*Limosilactobacillus reuteri*]"; NCBI Reference Sequence: WP_003666991.1; NCBI; https://www.ncbi.nlm.nih.gov/protein/WP_003666991.1?report=genbank&log$=prottop&blast_rank=1&RID=STXX2K05013; Jul. 31, 2013; 1 page.
U.S. Appl. No. 16/604,133, filed Oct. 9, 2019.
U.S. Appl. No. 16/604,134, filed Oct. 9, 2019.
"Chapter 3 Lactose content of milk and milk products," The American Journal of Clinical Nutrition, vol. 48, No. 4 pp. 1099-1044 (Oct. 1988) Available online, URL: https://academic.oup.com/ajcn/article-abstract/48/4/1099/4791817?redirectedFrom=fulltext.
"Uniprot: A0A0B5J47" (Apr. 1, 2015), Retrieved from the Internet, URL:http://ibis/exam/dbfetch.jsp?id=UNIPROT:A0A0B5J47 (Retrieved on May 11, 2017).
"Uniprot: A0AS2MCC8—beta galactosidase," (Feb. 17, 2016) Retrieved from the Internet, URL: https://ibis/exam/dbfetch.jsp?id=UNIPROT:A0A0S2MCC8 [retrieved on Mar. 9, 2018).
Broune et al. "Catalytic Plasticity of Fatty Acid Modification Enzymes Underlying Chemical Diversity of Plant Lipids," Science, vol. 282, pp. 1315-1317 (1998).
Database GenBank: ACE06986.1, (Jun. 8, 2012).
Database GenBank: CDR82630.1, (Jun. 11, 2014).
Devos et al., "Practical Limits of Function Prediction," Proteins: Structure, Function, and Genetics, vol. 41, pp. 98-107 (Aug. 2000).
GenBank Accession No. CAI98003.1 Feb. 27, 2015.
Guo et al., "Protein tolerance to random amino acid change," PNAS, vol. 101, No. 25, pp. 9205-9210 (Jun. 2004).
Horner et al., "ß-Galactosidase activity of commercial lactase samples in raw and pasteurized milk at refrigerated temperatures," J. Dairy Sci. 94: 3242-3249 (2011).
Keskin et al., "A new, structurally nonredundant, diverse data set of protein-protein interfaces and its implications," Protein Science, vol. 13, pp. 1043-1055 (2004).
Klimova E.V. Advantages of using beta-galactosidase for hydrolysis of lactose and obtaining galactooligosaccharides; prospects for the use of the obtained products in industrial food technologies, Food and processing industry, Abstract journal, No. 4, 2008, p. 1269.
Kreft et al., "Lactose hydrolysing ability of sonicated cultures of *Lactobacillus delbrueckii* ssp. bulgaricus 11842," le Lait, INRA Editions 81(3) pp. 355-364 (2001).
Nakagawa et al., "Overexpression and functional analysis of cold-active B-galactosidase from Arthrobacter psychrolocatohilus strain F2," Protein Expression and Purification 54 (2007) 295-299 (Available on line Mar. 2007).
Office Action and Search Report issued on May 14, 2021 in Russian Application No. 2019134223/10.
Office Action issued on Apr. 12, 2022 in U.S. Appl. No. 16/998,706 (US 2021-0032615).
Office Action issued on Jan. 22, 2021, in U.S. Appl. No. 16/998,706 (US 2021-0032615).
Ogurtsov A.N., Methods of bioinformatic analysis, Textbook, Kharkov, 2011, NTU "KhPI", pp. 4-5, 25.
Palak-Szukalska et al., "A novel cold-active B-D-galactosidase with transglycosylation activity from the *Arthrobacter* sp. 32cB—Gene cloning, purification and characterization," Process Biochemistry 49 (214) 2122-2133 (Available online Sep. 28, 2014).
Rhimi et al., "Exploring the acidotolerance of ß-galactosidase from *Lactobacillus delbrueckii* subsp. bulgaricus: an attractive enzyme for lactose bioconversion," Research in Microbiology, vol. 160 pp. 775-784 (2009) (Available online Sep. 2009).
Schmidt et al., "Identification, cloning and expression of a cold-active B-galactosidase from a novel Arctic bacterium, Alkalilactibacillus ikkense," (2010) Environmental Technology, 31:10, 1107-1114 (Published online Jun. 2010).
Seffernick et al., "Melamine Deaminase and Atrazine Chlorohydrolase: 98 Percent Identical but Functionally Different," Journal of Bacteriology, vol. 183, No. 8, pp. 2405-2410 (Apr. 2001).
Singer et al., "Genes & Genomes, A changing Perspective," University Science Books Mill Valley, CA (1998).
U.S. Patent and Trademark Office; Final Office Action; U.S. Appl. No. 16/998,706; dated Jun. 9, 2021; 15 pages.
UniProt Accession No. A0AOS2MCC8 Feb. 17, 2016.
UniProt Accession No. F0K2P6, May 3, 2011.
UniProt Accession No. G6F860, Jan. 25, 2012.
UniProt Accession Nos. TrEMBL, A7A6G3_BIFAD, Sep. 11, 2007, Q38UW6_LACSS, Nov. 22, 2005, Q38UW7_LACSS, Nov. 22, 2005, R5YYAO_9LACO, Jul. 24, 2013, F0TG79_LACAM, May 3, 2011, K2MWD3_BIFBI, Nov. 28, 2012, D4QFE8_BIFBI, Jul. 15, 2012, A0A133L394_BIFBR, Jul. 8, 2016, A0A1VSPPN6_9BIFI, Jul. 7, 2017, A0A1Q6ESN3_9BIFI, Apr. 12, 2016, A0A045FVZ6_LACDE, Mar. 16, 2017, 0A1L3JVR5_LACDL, Mar. 15, 2017, F0K2P6_LACD2, May 3, 2011 A0A0D5MI45_LACHE, May 27, 2015, A0A0D5MHU_LACHE, May 27, 2015, A0A1V8RDS6_BIFIN, Jun. 7, 2017, B3XQL8_LACRI, Sep. 23, 2008, B3XQL9_LACRI, Sep. 23, 2008, U6F4Q6_LACHE, Jan. 22, 2014, A8YWAO_LACH4, Jan. 15, 2008, LOCMGO_9LACO, Mar. 6, 2016, A0A0M410A2_STRR, Dec. 9, 2015, A0A0C0RIHO_9LACO, Nov. 11, 2015, 0A174B8K1_BIFAD, Apr. 7, 2016.
Uniprot:G6F860 (Oct. 2020).
UniProtKB—A0A076JKA5 (A0A076JKA5_BIFAD); Oct. 29, 2014; 7 pages.
UniProtKB—A0A0A1GLP4 (A0A0A1GLP4_BIFLN); Feb. 4, 2015; 8 pages.
UniProtKB—A0A0A715K5 (A0A0A715K5_9BIFI); Mar. 4, 2015; 8 pages.
UniProtKB—A0A0H2P357 (A0A0H2P357_BIFBI); Sep. 16, 2015; 7 pages.
UniProtKB—A0A0U5FVZ6 (A0A0U5FVZ6_LACDE); Mar. 16, 2016; 9 pages.
UniProtKB—A0A126SWK6 (A0A126SWK6_9BIFI); Jul. 6, 2016; 8 pages.
UniProtKB—A0A174BAQ4 (A0A174BAQ4_9BIFI); Sep. 7, 2016; 8 pages.
UniProtKB—A0A174BB61 (A0A174BB61_BIFAD); Sep. 7, 2016; 8 pages.
UniProtKB—A0A174BH17 (A0A174BH17_9FIRM); Sep. 7, 2016; 5 pages.
UniProtKB—A0A1D7UM07 (A0A1D7UM07_BIFLN); Jan. 18, 2017; 8 pages.
UniProtKB—A0A1D7ZXL7 (A0A1D7ZXL7_LIMFE); Jan. 18, 2017; 7 pages.
UniProtKB—A0A1S2W2V3 (A0A1S2W2V3_BIFLN); Apr. 12, 2017; 8 pages.
UniProtKB—A0A1X2Z956 (A0A1X2Z956_BIFAD); Jul. 5, 2017; 8 pages.
UniProtKB—A0A1X2ZA47 (A0A1X2ZA47_BIFAD); Jul. 5, 2017; 7 pages.
UniProtKB—A0A1X2ZAP4 (A0A1X2ZAP4_BIFAD); Jul. 5, 2017; 7 pages.
UniProtKB—A0A2G5Q4A6 (A0A2G5Q4A6_9BIFI); Jan. 31, 2018; 8 pages.
UniProtKB—A0A4ROSL12 (A0A4ROSL12_BIFLN); Jul. 31, 2019; 8 pages.
UniProtKB—A0A4R0U1N4 (A0A4R0U1N4_BIFLN); Jul. 31, 2019; 8 pages.
UniProtKB—A0A6A2R535 (A0A6A2R535_BIFAD); Jun. 17, 2020; 7 pages.
UniProtKB—A0A6B1X5Q7 (A0A6B1X5Q7_9BIFI); Jun. 17, 2020; 6 pages.
UniProtKB—A0A611DQE1 (A0A611DQE1_BIFLN); Aug. 12, 2020; 8 pages.
UniProtKB—A0A6L4K944 (A0A6L4K944_BIFAD); Oct. 7, 2020; 7 pages.
UniProtKB—A0A6L4V5B5 (A0A6L4V5B5_9BIFI); Oct. 7, 2020; 8 pages.
UniProtKB—A0A7D9N5G4 (A0A7D9N5G4_LACJH); Dec. 2, 2020; 8 pages.

(56) References Cited

OTHER PUBLICATIONS

UniProtKB—A0A829LWJ6 (A0A829LWJ6_LIMFE); Sep. 29, 2021; 7 pages.
UniProtKB—A5VKG8 (A5VKG8_LIMRD); Jul. 10, 2007; 8 pages.
UniProtKB—B2GAA1 (B2GAA1_LIMF3); Jun. 10, 2008; 7 pages.
UniProtKB—B2GAA2 (B2GAA2_LIMF3); Jun. 10, 2008; 6 pages.
UniProtKB—D6ZY97 (D6ZY97_BIFLJ); Aug. 10, 2010; 8 pages.
UniProtKB—E4SLB1 (E4SLB1_LACAR); Feb. 8, 2011; 8 pages.
UniProtKB—E8MRV2 (E8MRV2_BIFL1); Apr. 5, 2011; 8 pages.
UniProtKB—F0HTF8 (F0HTF8_LACDL); May 3, 2011; 9 pages.
UniProtKB—F0TG75 (F0TG75_LACAM); May 3, 2011; 8 pages.
UniProtKB—F2M1D8 (F2MID8_LACAL); May 11, 2011; 8 pages.
UniProtKB—F4AFP0 (F4AFP0_LACJH); Jun. 28, 2011; 8 pages.
UniProtKB—F8ASA8 (F8ASA8_BIFLN); Sep. 21, 2011; 8 pages.
UniProtKB—G6F860 (G6F860_LACDE); Jan. 25, 2012; 9 pages.
UniProtKB—I3WJ66 (I3WJ66_BIFBI); Sep. 5, 2012; 8 pages.
UniProtKB—K215J0 (K215J0_BIFBI); Nov. 28, 2012; 8 pages.
UniProtKB—Q5FJD5 (Q5FJD5_LACAC); Mar. 1, 2005; 9 pages.
UniProtKB—Q74KL4 (Q74KL4_LACJO); Jul. 5, 2004; 8 pages.
UnitProtKB—D9ZDZ1 (D9ZDZ1_9ZZZZ); Oct. 5, 2010; 7 pages.
Van De Guchte, et al., Beta-galactosidase [*Lactobacillus delbrueckii* subsp. bulgaaricus ATCC 11842 = JCM 1002] GenBank: CAI98003 [Feb. 2015].
Wang et al., "A novel cold-adapted B-galactosidase isolated from *Halomonas* sp. S62: gene cloning, purification and enzymatic characterization," World J. Microbiol Biotechnol (2013) 29:1473-1480 (Published on line Mar. 2013).
Whisstock et al., "Prediction of protein function from protein sequence and structure," Quarterly Reviews of Biophysics, vol. 36, No. 3 (pp. 307-340) (2003).
Wierzbicka-Wos et al., "A novel cold-active B-D-galactosidase from the *Paracoccus* sp. 32d—gene cloning, purification and characterization," Microbial Cell Factories 2011, 10:108 pp. 1-12.
Witkowski et al. "Conversion of B-Ketoacyl Synthase to a Malonyl Decarboxylase by Replacement of the Active-Site Cysteine with Glutamine," Biochemistry, vol. 38, pp. 11643-11650 (1999).
Skripnyuk A.A., et al.; "Modern methods for producing ß-galactosidase"; Science Innovations Technologies, 3; 2014; pp. 198-204.
Banerjee, Goutam et al.; "Is divalent magnesium cation the best cofactor for bacterial beta-galactosidase?"; J Biosci, vol. 43, No. 5; Oct. 4, 2018; pp. 941-945.
Biocceleration Ltd.; Seq Alignment Result (U.S. Appl. No. 16/604,134 SEQ #7 vs Tzortis et al. (US2009/0110770); Seq #2 using SLIC and ABSS SEQ—to SEQ (aa); Jun. 27, 2023.
Karlsson, Maria A. et al.; "Changes in stability and shelf-life of ultra-high temperature treated milk during long term storage at different temperatures"; Heliyon, vol. 5; Sep. 12, 2019; 9 pages.
Kuznetsova, E., "Brackets in Text of Legal Document as a Linguistic and Cognitive Phenomenon"; Institute of Humanities, Severodvinsk branch of Lomonosov Northern (Arctic) Federal University; Vestnik Moskovskogo gosudarstvennogo oblastnogo universiteta: Russian Philology, No. 3; ISSN 2072-8522; 2015; pp. 37-43.
Nguyen, Thao Thi et al.; "Effect of mutations to amino acid A301 and F361 in thermostability and catalytic activity of the beta-galactosidase from Bacillus subtilis VTCC-DVN-12-01"; BMC Biochemistry (2016) 17:15; Jul. 2016; 11 pages.
Patent Office of the Russian Federation: Federal Institute of Industrial Property; Office Action (Enquiry) (English translation); Russian Patent Application No. 2021112325/10(026315); Jun. 19, 2023; 10 pages.
Seffernick, Jennifer et al.; "Melamine Deaminase and Atrazine Chlorohydrolase: 98 Percent Identical but Functionally Different"; Journal of Bacteriology, vol. 183, No. 8; Apr. 2001; pp. 2405-2410.
Whisstock, James C. et al.; "Prediction of protein function from protein sequence and structure"; Quarterly Review of Biophysics 36, 3; Aug. 2003; pp. 307-340.
Cecchini et al.; OM protein—protein search, using sw model; GenCore version 6.4.2; run on Jan. 31, 2022; title: US-16-604-129A-22; 6 pages.
Genbank Accession KRO12099 (https://www.ncbi.nlm.nih.gov/protein/KRO12099.1?report=genbank&log$=protalign&blast_rank=1&RID=NRM8Y7MN016); publication date: Nov. 6, 2015; 2 pages.
UniProt—A0A174B8K1_BIFAD; Sep. 7, 2016; 6 pages.

\* cited by examiner

| G no | pH 6,7 at 4°C | pH 6,7 at 37°C | pH 6,7 at 43°C | % gal inhibition |
|---|---|---|---|---|
| 4 | 9,4 | 118,1 | 84,7 | 34 |
| 11 | 8,4 | 69,2 | 111,3 | 9 |
| 16 | 1,6 | 23,4 | 17,0 | 45 |
| 33 | 12,5 | 130,1 | 173,3 | 3 |
| 35 | 12,5 | 121,0 | 100,9 | 27 |
| 40 | 1,2 | 15,8 | 12,4 | 53 |
| 44 | 24,2 | 331,5 | 295,9 | 35 |
| 51 | 20,7 | 250,6 | 214,3 | 35 |
| 57 | 7,4 | 104,6 | 97,2 | 47 |
| 62 | 5,2 | 48,5 | 37,6 | 83 |
| 66 | 15,2 | 187,2 | 136,8 | 23 |
| 83 | 26,9 | 272,9 | 195,1 | 37 |
| 84 | 15,9 | 161,9 | 118,0 | 31 |
| 95 | 28,8 | 288,1 | 250,7 | 37 |
| 100 | 27,9 | 339,9 | 238,1 | 39 |
| 104 | 12,9 | 90,5 | 112,9 | 1 |
| 108 | 27,2 | 277,9 | 213,1 | 34 |
| 109 | 25,3 | 300,1 | 218,3 | 30 |
| 118 | 16,9 | 113,8 | 122,3 | 14 |
| 145 | 2,4 | 24,1 | 22,6 | 64 |
| 158 | 34,2 | 254,7 | 334,8 | 27 |
| 224 | 11,2 | 389,9 | 131,4 | 48 |
| 256 | 15,5 | 111,3 | 112,8 | 14 |
| 282 | 8,4 | 58,5 | 48,6 | 62 |
| 335 | 4,4 | 42,4 | 30,9 | 50 |
| 500 | 3,9 | 46,9 | 13,1 | 35 |
| 600 | 7,4 | 61,9 | 45,6 | 44 |

Figure 14

| G no | pH 5.5 at 4°C | pH 5.5 at 37°C | pH 5.5 at 43°C |
|---|---|---|---|
| 4 | 1,4 | 44,1 | 29,6 |
| 11 | 7,6 | 57,9 | 75,5 |
| 16 | 0,2 | 0,7 | 0,4 |
| 33 | 10,4 | 88,2 | 89,9 |
| 35 | 1,7 | 51,3 | 40,9 |
| 40 | 3,3 | 21,8 | 15,7 |
| 44 | 4,9 | 111,2 | 80,7 |
| 51 | 4,0 | 84,6 | 58,8 |
| 57 | 0,6 | 17,8 | 13,1 |
| 62 | 6,0 | 60,5 | 49,7 |
| 66 | 0,8 | 63,3 | 42,7 |
| 83 | 6,7 | 108,4 | 57,2 |
| 84 | 8,4 | 99,4 | 62,4 |
| 95 | 7,0 | 121,3 | 64,7 |
| 100 | 5,9 | 128,2 | 55,2 |
| 104 | 10,6 | 60,4 | 60,5 |
| 108 | 7,0 | 116,5 | 69,5 |
| 109 | 5,7 | 116,5 | 62,6 |
| 118 | 14,8 | 76,0 | 65,0 |
| 145 | 4,9 | 28,8 | 15,8 |
| 158 | 18,4 | 129,4 | 126,8 |
| 224 | 4,4 | 21,0 | 7,4 |
| 256 | 14,0 | 62,7 | 57,0 |
| 282 | 6,4 | 50,8 | 24,9 |
| 335 | 0,3 | 9,4 | 3,1 |
| 500 | 0,1 | 0,4 | 0,5 |
| 600 | 4,0 | 32,7 | 26,9 |

Figure 15

| G no | pH 4.5 at 4°C | pH 4.5 at 37°C | pH 4.5 at 43°C |
| --- | --- | --- | --- |
| 4 | 1,2 | 2,9 | 2,0 |
| 11 | 1,7 | 18,9 | 3,3 |
| 16 | 0,1 | 0 | 0 |
| 33 | 1,6 | 24,7 | 0,7 |
| 35 | 1,6 | 3,7 | 2,5 |
| 40 | 3,4 | 12,9 | 10,6 |
| 44 | 4,3 | 12,5 | 11,8 |
| 51 | 3,9 | 12,8 | 11,0 |
| 57 | 0,4 | 0,1 | -0,5 |
| 62 | 4,2 | 19,9 | 16,6 |
| 66 | 0,8 | 1,6 | 1,2 |
| 83 | 5,6 | 11,2 | 12,4 |
| 84 | 7,9 | 22,7 | 17,1 |
| 95 | 7,0 | 12,8 | 10,4 |
| 100 | 5,6 | 12,5 | 11,4 |
| 104 | 4,5 | 29,7 | 24,1 |
| 108 | 6,7 | 14,3 | 12,8 |
| 109 | 5,5 | 10,4 | 19,8 |
| 118 | 5,8 | 37,5 | 25,6 |
| 145 | 5,0 | 8,9 | 7,2 |
| 158 | 4,2 | 12,7 | 25,1 |
| 224 | 4,1 | 0,0 | 0,0 |
| 256 | 7,9 | 23,2 | 17,2 |
| 282 | 6,3 | 7,5 | 7,2 |
| 335 | 0,3 | 0 | 0,0 |
| 500 | 0,0 | 0 | 0 |
| 600 | 1,6 | 12,2 | 5,0 |

Figure 16

LACTASE ENZYMES WITH IMPROVED PROPERTIES

CROSS REFERENCE TO RELATED APPLICATIONS

The present application is a continuation of U.S. application Ser. No. 16/604,129, filed Oct. 9, 2019, now U.S. Pat. No. 11,525,129, issued on Dec. 13, 2022, which is the U.S. National Stage of International Application No. PCT/EP2018/059250, filed Apr. 11, 2018, which claims priority to European Patent Application No. 17166021.0, filed Apr. 11, 2017.

SEQUENCE LISTING

The instant application contains a Sequence Listing which has been submitted electronically in XML format and is hereby incorporated by reference in its entirety. Said XML copy, created on Jan. 16, 2023, is named "030427-0380_SL.xml" and is 70,779 bytes in size.

FIELD OF THE INVENTION

The present invention relates to new improved peptide or dimeric peptides exhibiting beta-galactosidase enzyme activity as well as improved methods for reducing the lactose content in compositions, such as dairy products.

BACKGROUND OF THE INVENTION

In order to grow on milk, lactose hydrolysis is a good way for lactic acid bacteria to obtain glucose and galactose as carbon source. Lactase (beta-galactosidase; EC 3.2.1.23) is the enzyme that performs the hydrolysis step of the milk sugar lactose into monosaccharides. The commercial use of lactase is to break down lactose in dairy products. Lactose intolerant people have difficulties to digest dairy products with high lactose levels. It is estimated that about 70% of the world's population has a limited ability to digest lactose. Accordingly, there is a growing demand for dairy food products that contain no or only low levels of lactose.

Lactases have been isolated from a large variety of organisms, including microorganisms like *Kluyveromyces* and *Bacillus*. *Kluyveromyces*, especially *K. fragilis* and *K. lactis*, and other fungi such as those of the genera *Candida*, *Torula* and *Torulopsis*, are a common source of fungal lactases, whereas *B. coagulans* and *B. circulans* are well known sources for bacterial lactases. Several commercial lactase preparations derived from these organisms are available such as Lactozym® (available from Novozymes, Denmark), HA-Lactase (available from Chr. Hansen, Denmark) and Maxilact® (available from DSM, the Netherlands), all from *K. lactis*. All these lactases are so-called neutral lactases having a pH optimum between pH 6 and pH 8, as well as a temperature optimum around 37° C. When such lactases are used in the production of, e.g. low-lactose yoghurt, the enzyme treatment will either have to be done in a separate step before fermentation or rather high enzyme dosages have to be used because their activity will drop as the pH decreases during fermentation. Also, these lactases are not suitable for hydrolysis of lactose in milk performed at high temperature, which would in some cases be beneficial in order to keep the microbial count low and thus ensure high milk quality. Furthermore, the known lactases would not be suitable for use in a desired process for the production of ultra-heat treated (UHT) milk, wherein enzymes were added prior to the UHT treatment.

WO2010092057 and WO0104276 relates to cold-active beta-galactosidases. WO07110619 relates to beta-galactosidase with high transgalactosylating activity, whereas WO2009071539 relates to beta-galactosidase with lower transgalactosylating activity.

OBJECT OF THE INVENTION

It is an object of embodiments of the invention to provide beta-galactosidases with properties that enable the production of improved lactose-free or low-lactose products.

It is a further object of embodiments of the invention to provide beta-galactosidases with properties that enable the improved, such as easier, faster, more reliable or less expensive production methods for the lowering of lactose in a product, such as lactose-free or low-lactose products.

SUMMARY OF THE INVENTION

The present inventor(s) have identified beta-galactosidases with properties not previously described that enable the production of improved lactose-free or low-lactose products as well as enabling improved production methods for such lactose-free or low-lactose products. In particular these beta-galactosidases have been shown to be very stable with relatively high activity at a very broad range of both temperatures as well as pH values. They are also useable at specific temperatures, such as at high temperatures and pH values not normally seen with these enzymes. First of all, this enables to the use of beta-galactosidases at specific pH values and temperatures that were not known to be possible. It also enables the use of the same specific enzyme in several different applications, which is highly requested in the industry.

So, in a first aspect the present invention relates to a peptide exhibiting beta-galactosidase enzyme activity, which has an amino acid sequence represented by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

In a second aspect the present invention relates to a dimeric peptide exhibiting beta-galactosidase enzyme activity, which dimeric peptide consist of two peptides having an amino acid sequence represented by SEQ ID NO: 2 and 3; 5 and 6; 20 and 21; 23 and 24; 26 and 27; or 28 and 29, or enzymatically active fragments thereof, or an amino acid sequence of any one thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

In a third aspect the present invention relates to a nucleotide sequence which encodes a peptide or dimeric peptide exhibiting beta-galactosidase enzyme activity according to the invention.

In a further aspect the present invention relates to a host cell comprising a nucleotide sequence which encodes a peptide or dimeric peptide exhibiting beta-galactosidase enzyme activity according to the invention.

In a further aspect the present invention relates to a method for producing a peptide or dimeric peptide exhibiting beta-galactosidase enzyme activity according to the invention, which method comprises the expression of a vector containing a nucleotide sequence according to the invention in a suitable host cell; and purifying said peptide or dimeric peptide from the expression products of said host cell.

In a further aspect the present invention relates to a method for reducing the lactose content in a composition containing lactose, such as in a dairy products, comprising the step of contacting said composition with a peptide or dimeric peptide exhibiting beta-galactosidase enzyme activity, which peptide has an amino acid sequence represented by SEQ ID NO:1-33; or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences; or a host cell expressing any one of said peptides, at a pH ranging from 3-10 and at a temperature ranging from 0° C.-140° C.

In a further aspect the present invention relates to the use of a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences; or a host cell expressing any one of said peptides for producing a dairy product with a reduced lactose content.

In some embodiments this composition containing lactose or this dairy product is selected from the group consisting of lactose-free milk, low-lactose milk, yoghurt, including unpasteurized as well as pre and post-pasteurized yoghurt, cheese, fermented milk products, dietary supplement and probiotic dietary products. In some other embodiments this host cell is any one selected from a bacteria of the genus *Bifidobacterium*, such as *Bifidobacterium adolescentis*, *Bifidobacterium bifidum*, *Bifidobacterium breve*, *Bifidobacterium catenulatum*, *Bifidobacterium longum* or from the genus *Lactobacillus*, such as *L. sakei*, *L. amylovorus*, *L. delbrueckii* subsp. *bulgaricus*, *L. delbrueckii* subsp. *lactis*, *L. delbrueckii* subsp. *Indicus*, *L. crispatus*, *L. reuteri*, *L. helveticus* or from *Streptococcus thermophilus*. In some other embodiments the lactose concentration is reduced to less than about 1%, such as to less than about 0.1% or lower, such as to less than about 0.01%.

In a further aspect the present invention relates to a method for producing a dairy product the method comprising the steps of:

a) providing a milk-based substrate comprising lactose;

b) adding a peptide or dimeric peptide exhibiting beta-galactosidase activity, which peptide has an amino acid sequence represented by SEQ ID NO:1-33; or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences to said milk-based substrate comprising lactose; and c) treating said milk-based substrate with said peptide or dimeric peptide exhibiting beta-galactosidase activity.

In a further aspect the present invention relates to a dairy product prepared by a method according to the invention.

In a further aspect the present invention relates to a food product, such as a dairy product comprising a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences.

In a further aspect the present invention relates to a food product, such as a dairy product comprising a host cell expressing a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences. In some specific embodiments such a food product is selected from beverages, infant foods, cereals, bread, biscuits, confectionary, cakes, food supplements, dietary supplements, probiotic comestible products, prebiotic comestible products, animal feeds, poultry feeds and medicaments, or a dairy product selected from the group consisting of lactose-free milk, low-lactose milk, dried milk powder, baby milks, yoghurt, ice cream, cheese, fermented milk products, dietary supplement and probiotic dietary products.

LEGENDS TO THE FIGURE

FIG. 1. The specific activity of the purified enzymes determined at pH 6.7 at 37° C. with lactose as substrate, described SUAL-1, discussed in example 6. The measured standard deviation at the given condition was less than 6%.

Figure 2:
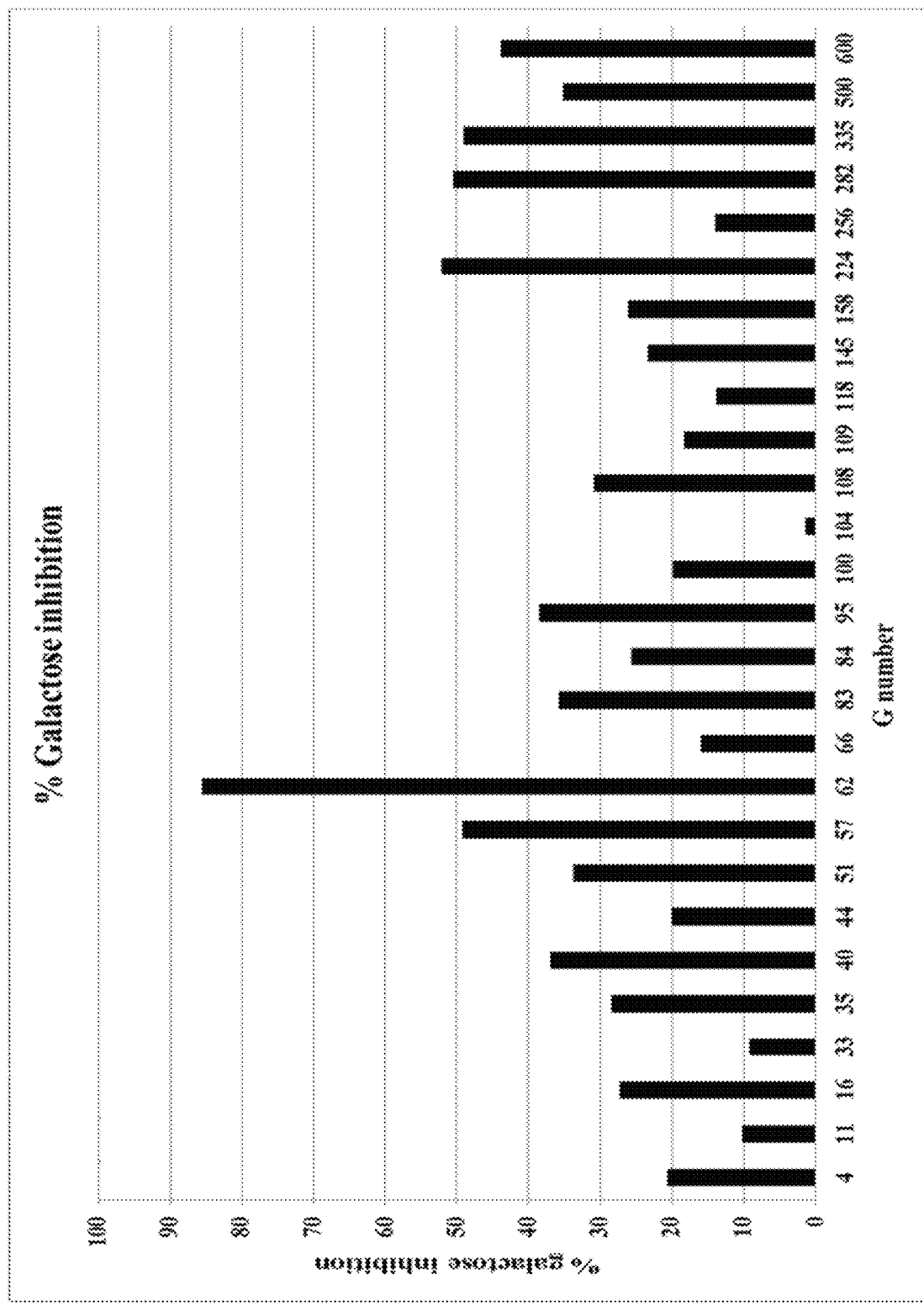

FIG. 2. The specific activity of the purified enzymes determined at pH 6.7 at 37° C. in presence of galactose, described as SUAG, discussed in example 7. The measured standard deviation at the given condition was less than 15%.

Figure 3:
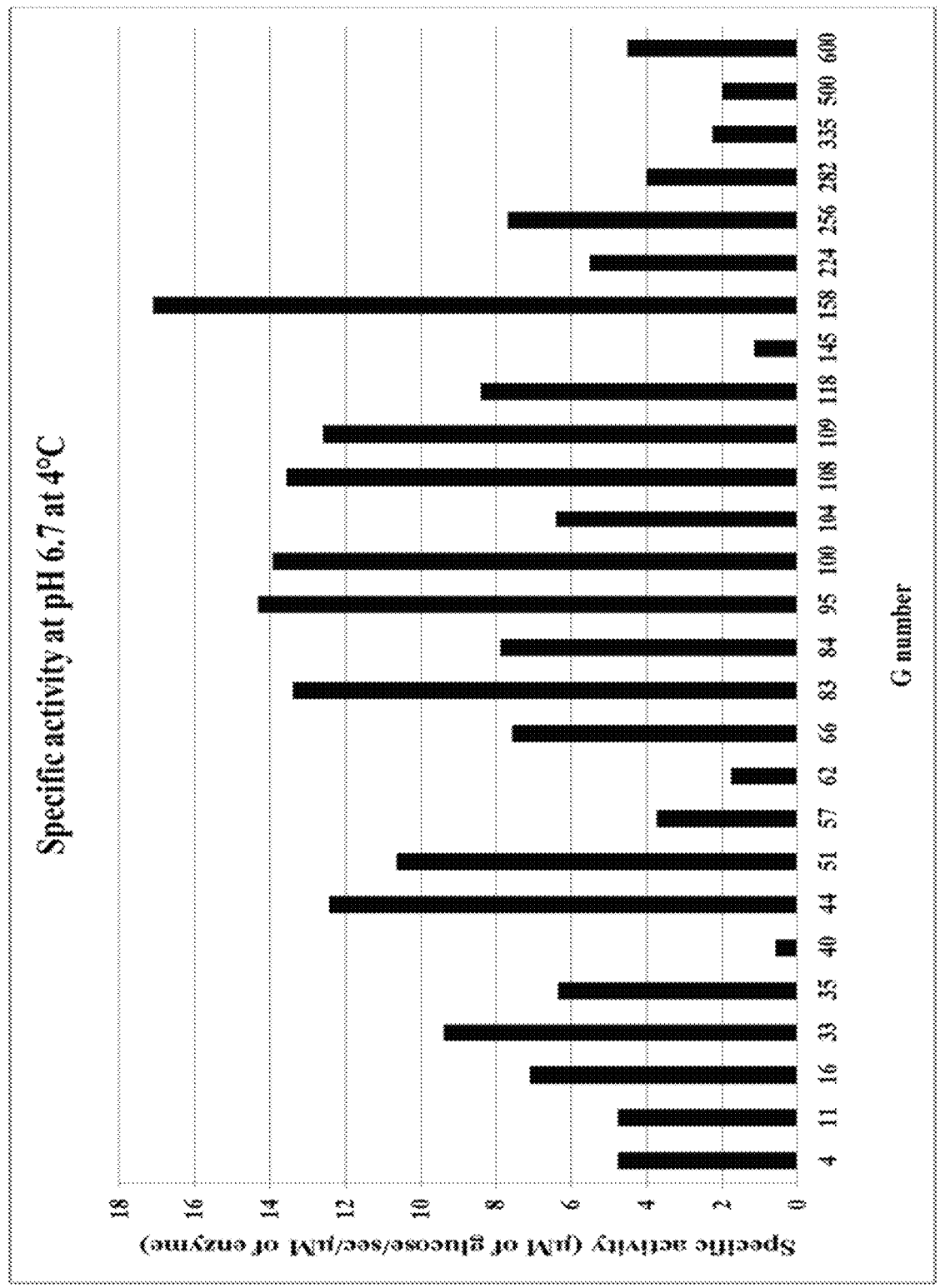

FIG. 3. The specific activity of the purified enzymes determined at pH 6.7 at 4° C. with lactose as substrate, described as SUAL-2, discussed in example 8. The measured standard deviation at the given condition was less than 5%.

Figure 4:
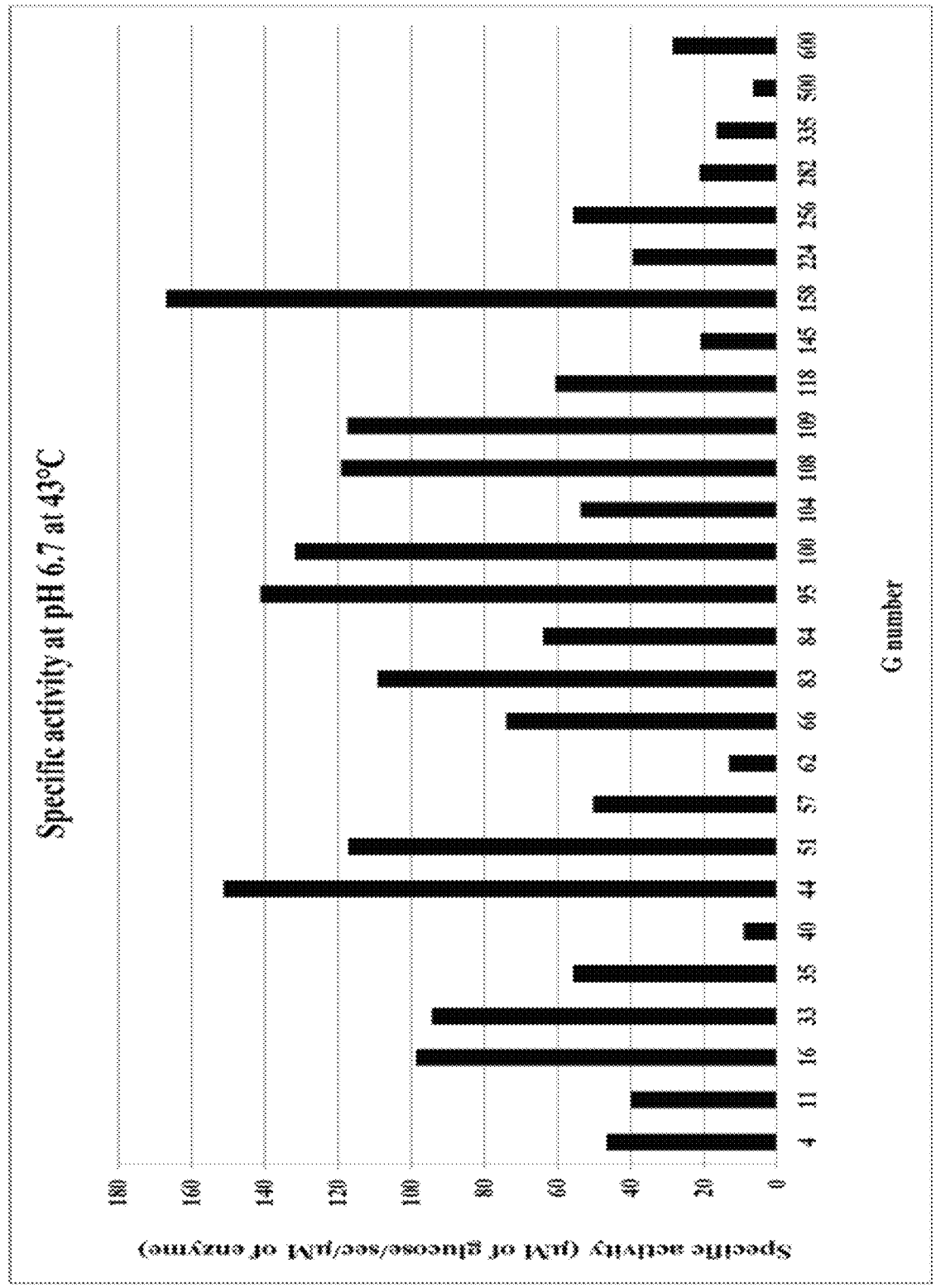

FIG. 4. The specific activity of the purified enzymes determined at pH 6.7 at 43° C. with lactose as substrate, described as SUAL-3, discussed in example 9. The measured standard deviation at the given condition was less than 5%.

Figure 5:
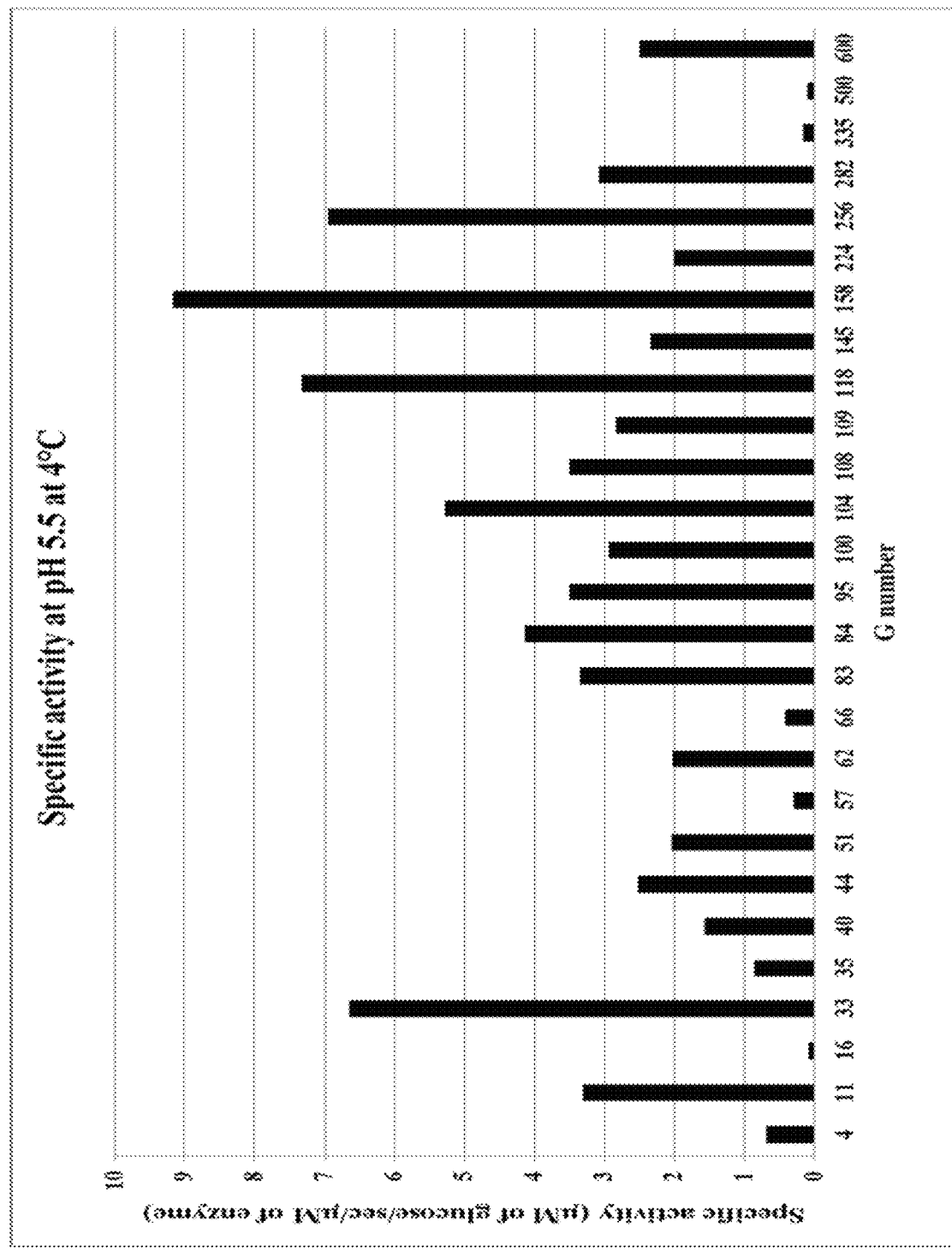

FIG. 5. The specific activity of the purified enzymes determined at pH 5.5 at 4° C. with lactose as substrate, described as SUAL-4, discussed in example 10. The measured standard deviation at the given condition was less than 5%.

Figure 6:
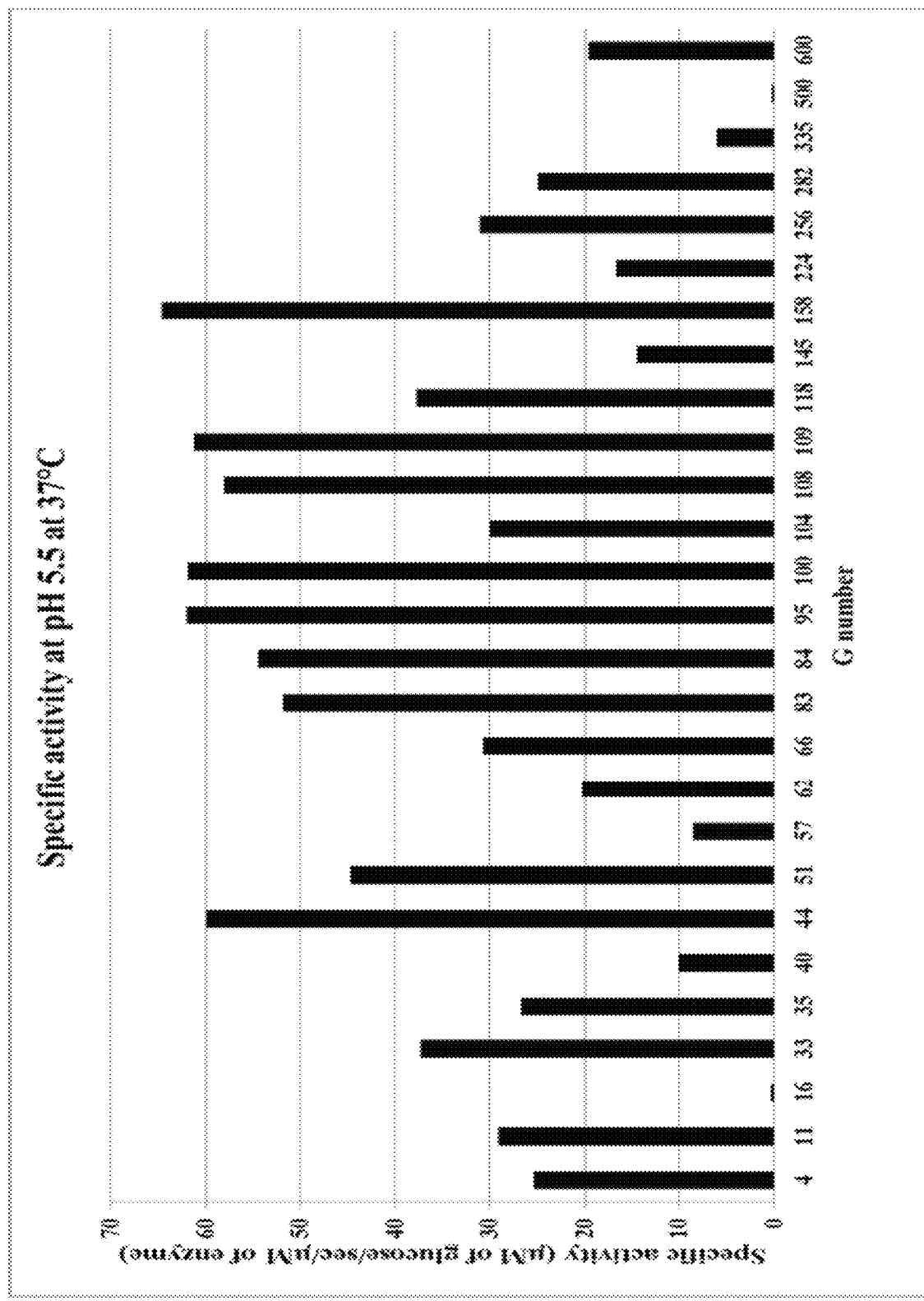

FIG. 6. The specific activity of the purified enzymes determined at pH 5.5 at 37° C. with lactose as substrate, described as SUAL-5, discussed in example 11. The measured standard deviation at the given condition was less than 5%.

Figure 7:
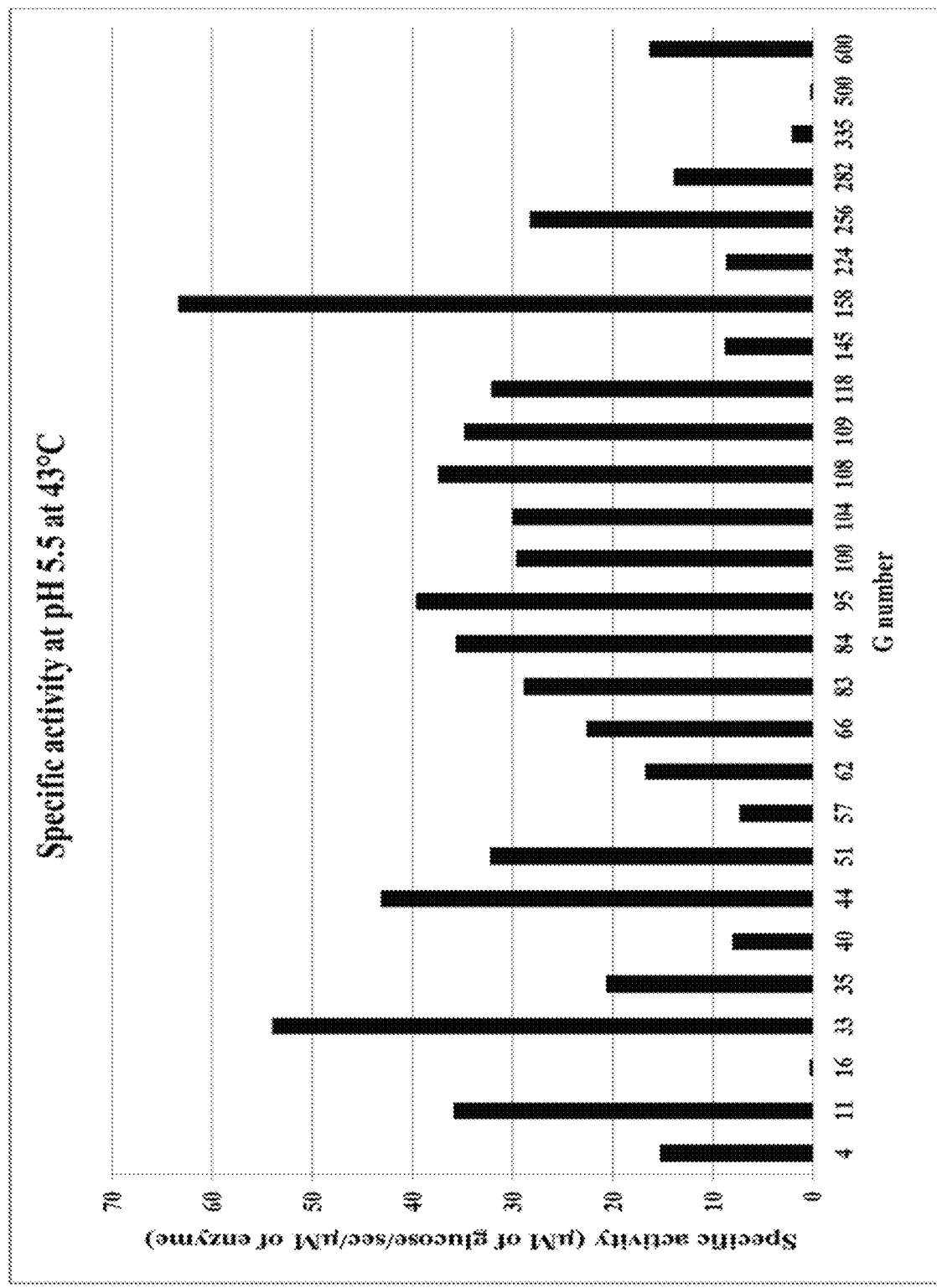

FIG. 7. The specific activity of the purified enzymes determined at pH 5.5 at 43° C. with lactose as substrate, described as SUAL-6, discussed in example 12. The measured standard deviation at the given condition was less than 5%.

Figure 8:
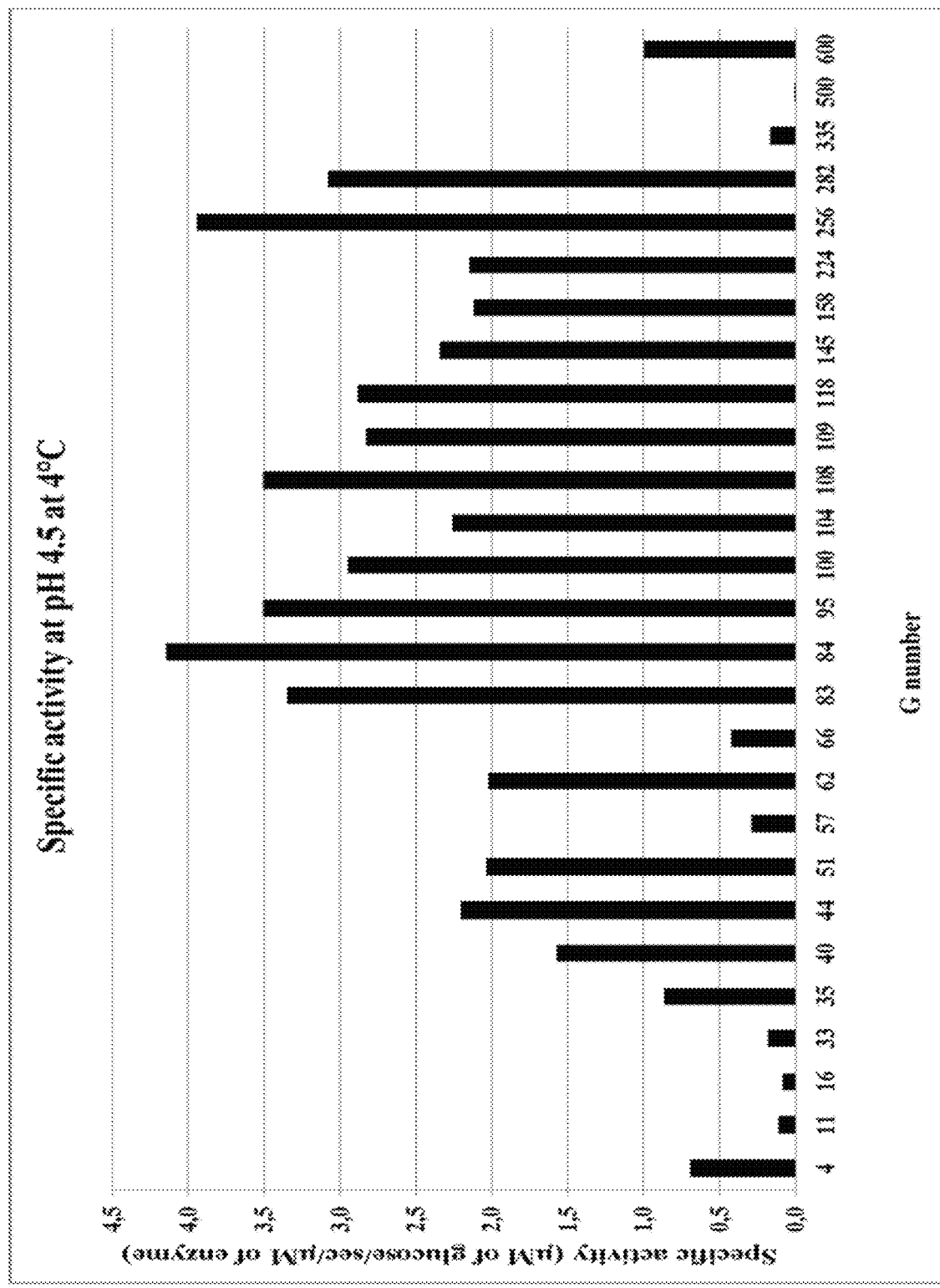

FIG. 8. The specific activity of the purified enzymes determined at pH 4.5 at 4° C. with lactose as substrate, described as SUAL-7, discussed in example 13. The measured standard deviation at the given condition was less than 5%.

Figure 9:
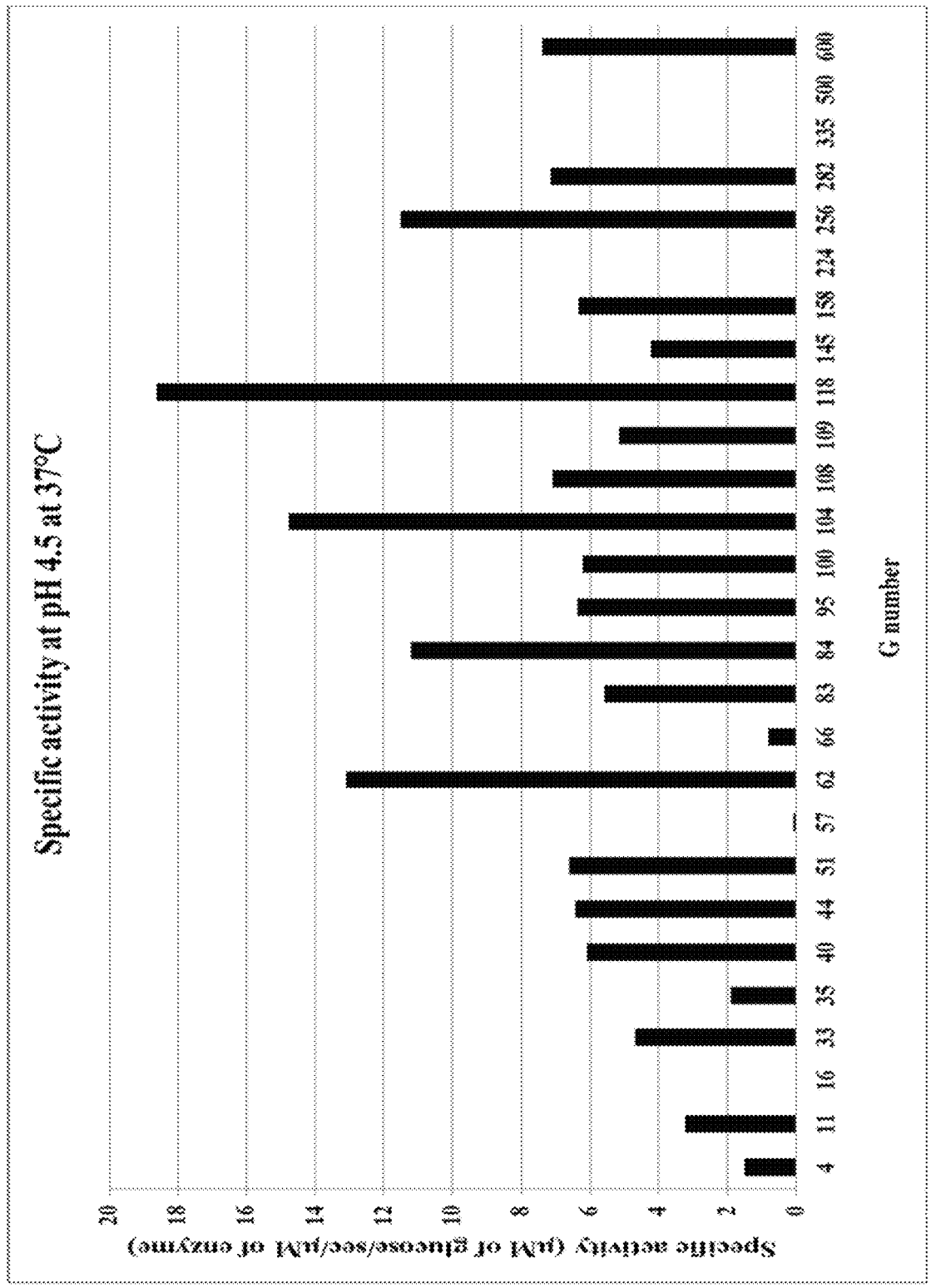

FIG. 9. The specific activity of the purified enzymes determined at pH 4.5 at 37° C. with lactose as substrate, described as SUAL-8, discussed in example 14. The measured standard deviation at the given condition was less than 5%.

Figure 10:
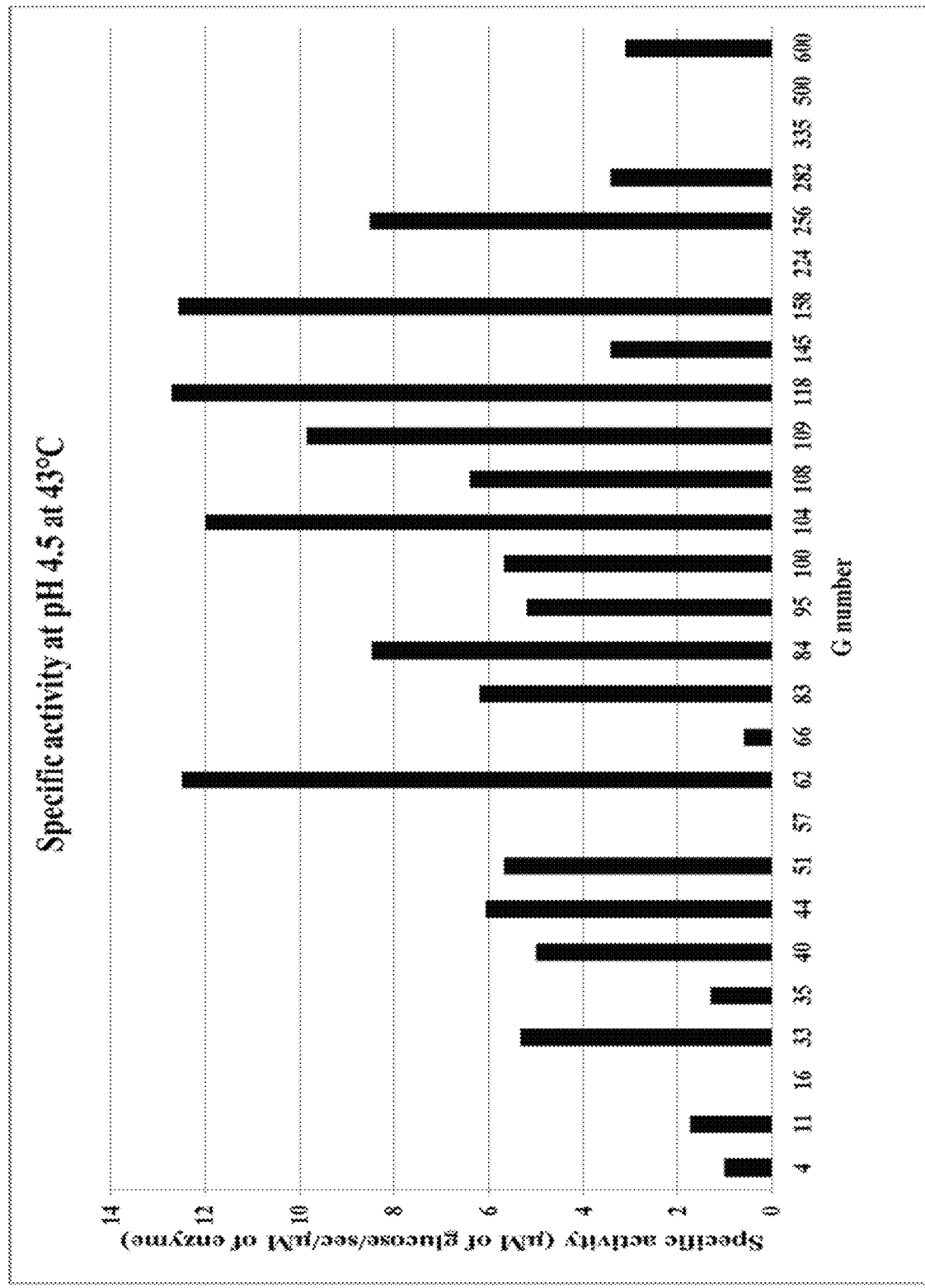

FIG. 10. The specific activity of the purified enzymes determined at pH 4.5 at 43° C. with lactose as substrate, described as SUAL-9, discussed in example 15. The measured standard deviation at the given condition was less than 5%.

Figure 11:
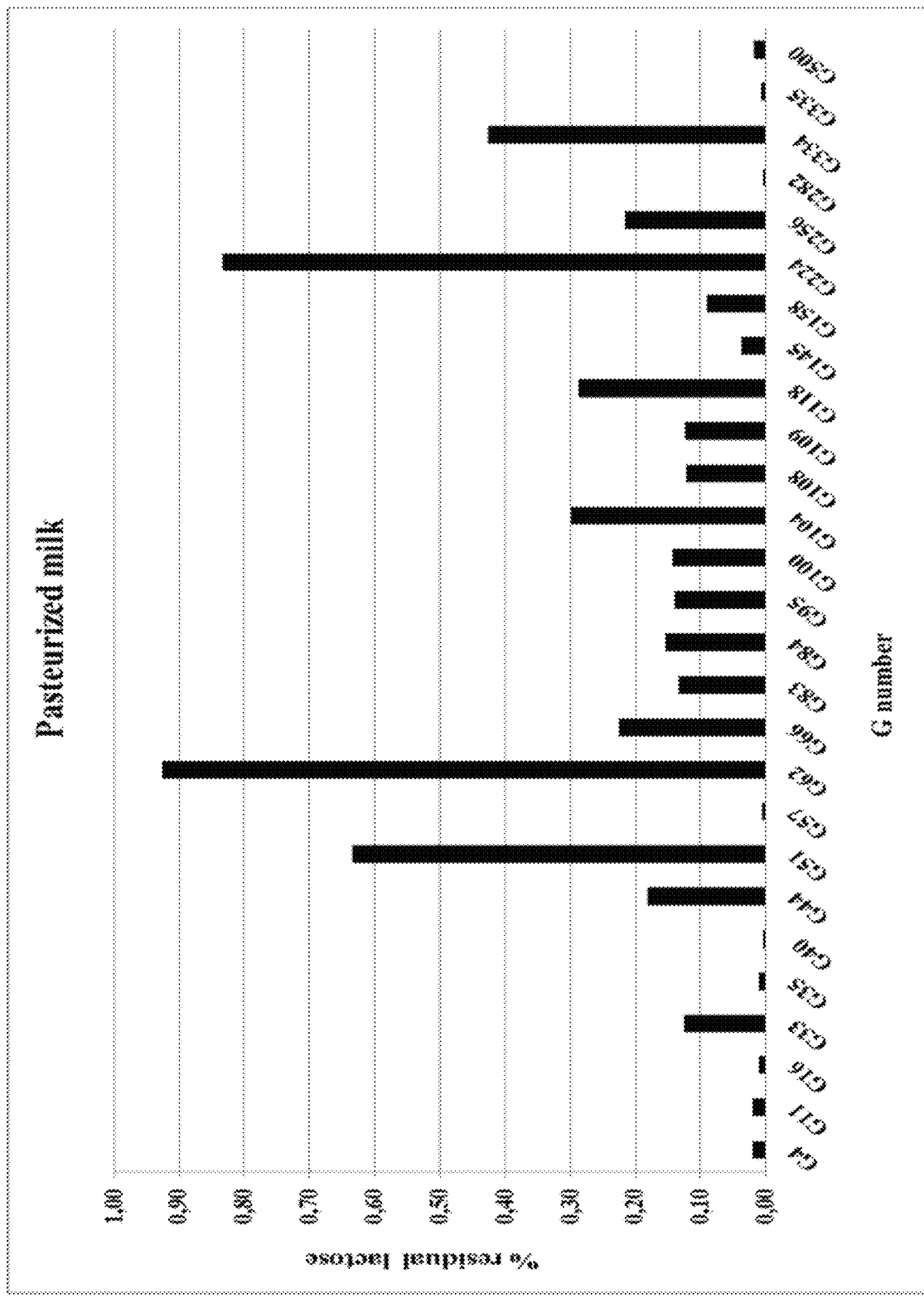

FIG. 11. The percentage residual lactose in the pasteurized milk, after the treatment with a fixed amount of the enzyme, after 24 hr at 5° C. determined using HPLC.

Figure 12:
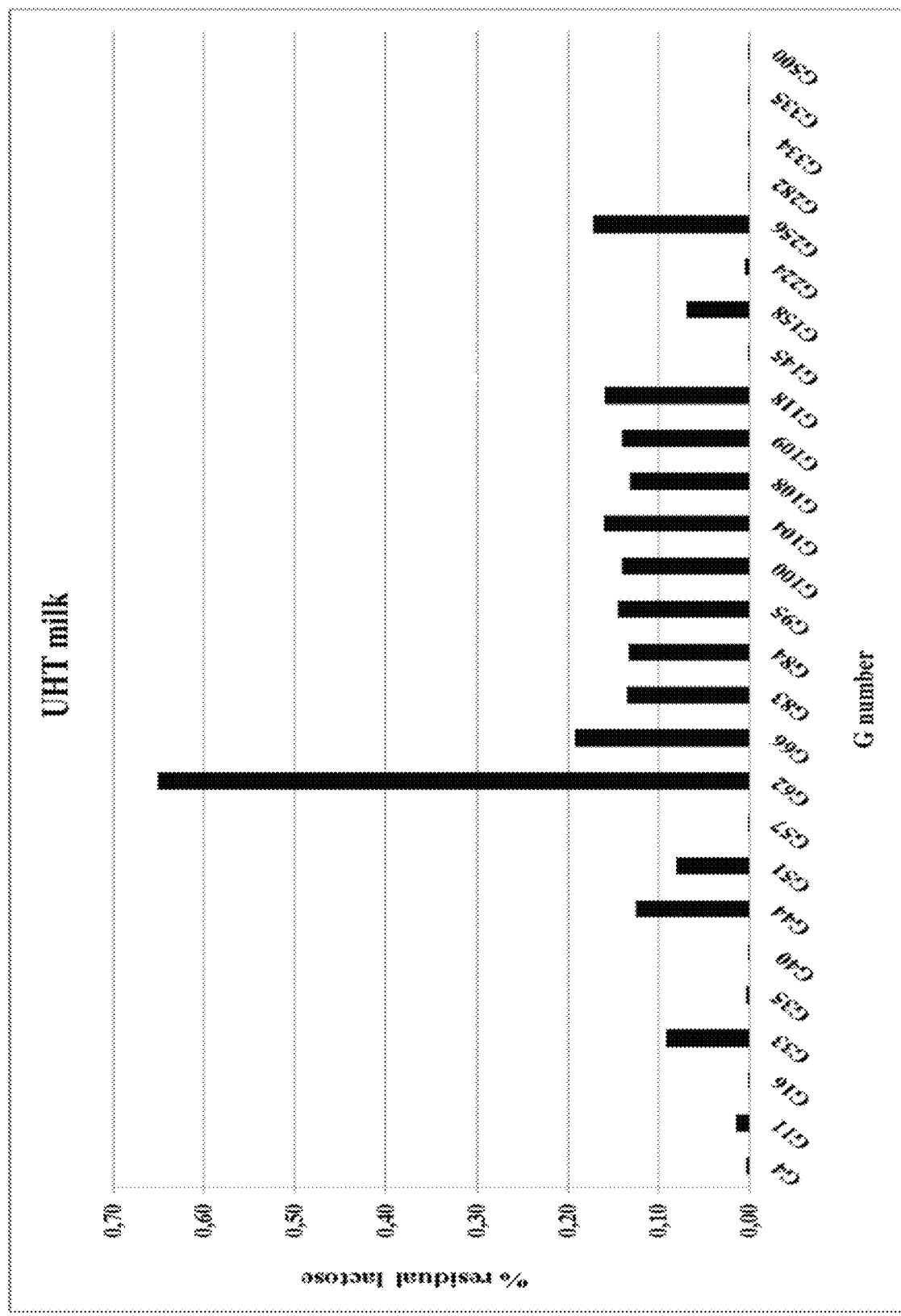

FIG. 12. The percentage residual lactose in the UHT milk, after the treatment with a fixed amount of the enzyme, after 24 hr at 25° C. determined using HPLC.

Figure 13:
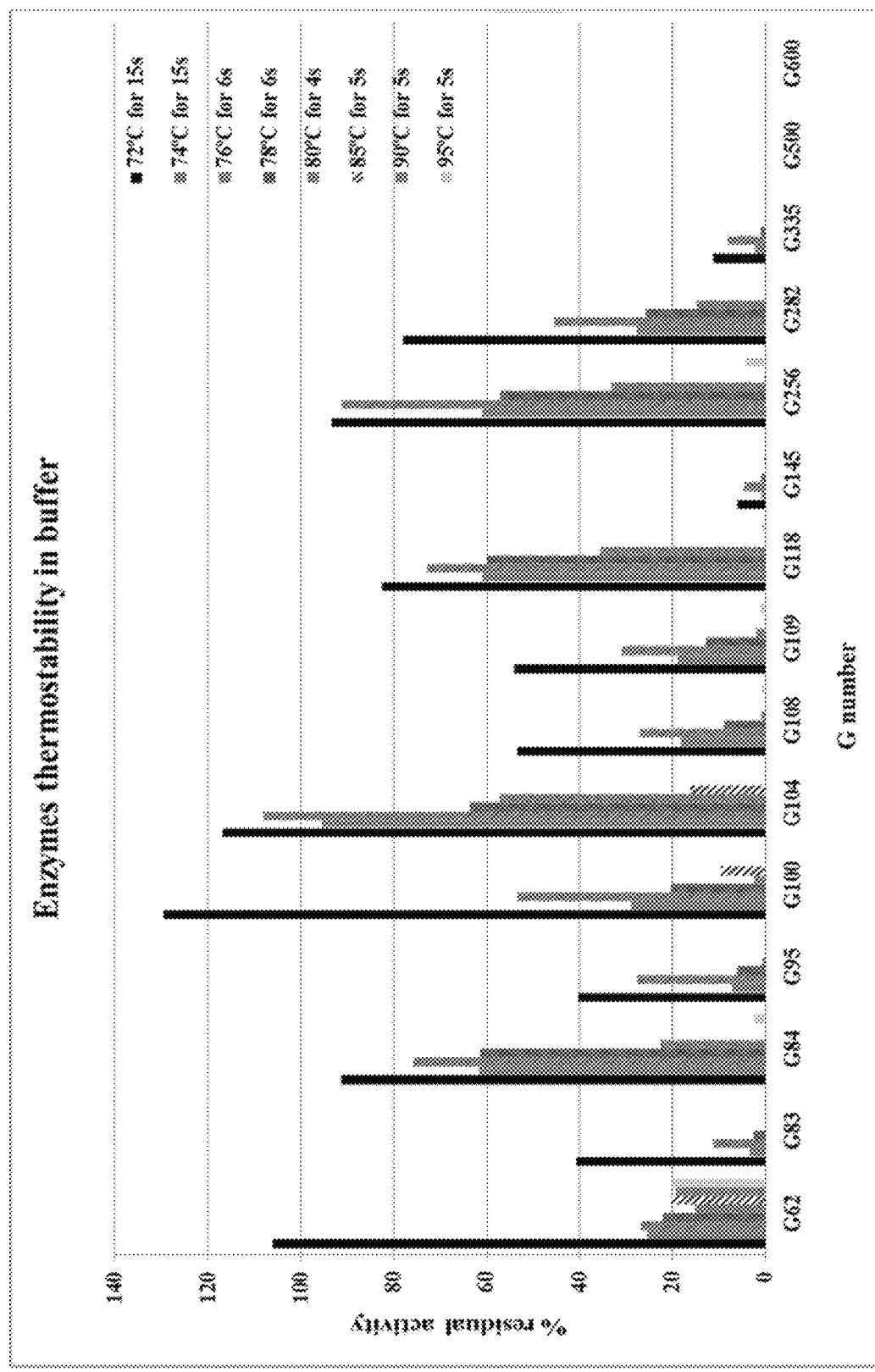

FIG. 13. The percentage residual activity of the purified enzymes at elevated temperatures, determined using lactose as substrate. The activity at pH 6.7 at 37° C. was considered as 100%.

FIG. 14. The specific activity of the purified enzymes determined at pH 6.7 at 4° C., 37° C. and 43° C. The measured specific activity is described as µmol glucose formed per minute per mg of enzyme. The galactose inhibition method is described in example 7 and calculated based on the µmol glucose formed per minute per mg of enzyme.

FIG. 15. The specific activity of the purified enzymes determined at pH 5.5 at 4° C., 37° C. and 43° C. The measured specific activity is described as µmol glucose formed per minute per mg of enzyme.

FIG. 16. The specific activity of the purified enzymes determined at pH 4.5 at 4° C., 37° C. and 43° C. The measured specific activity is described as µmol glucose formed per minute per mg of enzyme.

DETAILED DISCLOSURE OF THE INVENTION

The present inventors have found that certain peptides and dimeric peptides exhibiting beta-galactosidase enzyme activity are surprisingly stabile at many different physical conditions giving a relatively high activity outside of the ranges normally seen to be optimal for this class of enzymes.

Accordingly, these by the present inventors identified enzymes have a relatively high activity around 4° C. or 5° C. and may thus be used for lactose hydrolysis in the production of e.g. fresh milk. Moreover, the enzymes have also a relatively high activity in the range of 10° C.-25° C. and the exact same enzymes may thus be used for lactose hydrolysis in UHT milk. This feasibility of the enzymes even at broad ranges of temperatures is highly relevant since milk may be stored at room/ambient temperature which may be different in different parts of the world, also depending on the seasons. For the UHT treatment, the temperature is typically either around 135° C. or around 140° C. It is highly wanted that the enzymes may have activity in the range of a temperature up to 140° C. so that the enzyme may be added to raw milk before the UHT step. In the current practices the enzyme is added after the UHT step because the enzymes known in the art has a significant decrease in functional activity, such as to a value below measurable activity following the high heat treatment step. Also the milk is stored at room temperature which may vary significantly in different parts of the world.

Also these novel improved peptides exhibiting beta-galactosidase enzyme activity have been found to have activity in the temperature range normally used for pasteurization.

Accordingly, these enzymes may be added to raw milk prior to pasteurization. It is to be understood that the enzymes known in the art has a significant decrease in functional activity, such as to a value below measurable activity following a pasteurization step.

A further advantage of these novel improved peptides exhibiting beta-galactosidase enzyme activity is that they have a relatively low degree of galactose inhibition. The lower galactose inhibition of these novel enzymes is highly relevant for applications wherein very low lactose concentrations are desired.

In terms of applicability for fermented products it is highly advantageous that the enzymes as described herein have a high beta-galactosidase enzymatic activity at a relatively broad temperature range of between 4° C.-43° C., such as around 37° C., where fermentation would normally be optimal, but also that this activity of the beta-galactosidase enzyme is present at low pH, such as down to 4.5, or down to 4.0, or down to 3.5, or even down to pH 3.

In summary, it has been found by the present inventors that some peptides exhibiting beta-galactosidase enzyme activity is active over wide range of temperature, active over wide range of pH, has a general high hydrolytic activity without side activities, that these peptides have no or little galactose inhibition, such as less than 60%, and that they are stable over long-term storage.

The beta-galactosidase activity may be determined by measuring the amount of released glucose after incubation with lactose at set conditions. Released glucose can be detected by a coloring reaction.

Definitions

The term "milk", as used herein and in the context of the present invention, is to be understood as the lacteal secretion obtained by milking any mammal, such as cow, sheep, goats, buffalo or camel.

The term "composition containing lactose" as used herein refers to any composition, such as any liquid that contain lactose in significant measurable degree, such as a lactose content higher than 0.002% (0.002 g/100 ml). Encompassed within this term are milk and milk-based substrates.

The term "milk-based substrate", in the context of the present invention, may be any raw and/or processed milk material. Useful milk-based substrates include, but are not limited to solutions/suspensions of any milk or milk like products comprising lactose, such as whole or low fat milk, skim milk, buttermilk, low-lactose milk, reconstituted milk powder, condensed milk, solutions of dried milk, UHT milk, whey, whey permeate, acid whey, cream, fermented milk products, such as yoghurt, cheese, dietary supplement and probiotic dietary products. Typically the term milk-based substrate refers to a raw or processed milk material that is processed further in order to produce a dairy product.

The term "pasteurization" as used herein refers to the process of reducing or eliminating the presence of live organisms, such as microorganisms in a milk-based substrate. Preferably, pasteurization is attained by maintaining a specified temperature for a specified period of time. The specified temperature is usually attained by heating. The temperature and duration may be selected in order to kill or inactivate certain bacteria, such as harmful bacteria, and/or to inactivate enzymes in the milk. A rapid cooling step may follow.

The term "dairy product" as used herein may be any food product wherein one of the major constituents is milk-based. Usually the major constituent is milk-based and in some embodiments, the major constituent is a milk-based substrate which has been treated with an enzyme having beta-galactosidase activity according to a method of the present invention.

A dairy product according to the invention may be, e.g., skim milk, low fat milk, whole milk, cream, UHT milk, milk having an extended shelf life, a fermented milk product, cheese, yoghurt, butter, dairy spread, butter milk, acidified milk drink, sour cream, whey based drink, ice cream, condensed milk, dulce de leche or a flavored milk drink.

A dairy product may additionally comprise non-milk components, e.g. vegetable components such as, e.g., vegetable oil, vegetable protein, and/or vegetable carbohydrates. Dairy products may also comprise further additives such as, e.g., enzymes, flavoring agents, microbial cultures such as probiotic cultures, salts, sweeteners, sugars, acids, fruit, fruit prep, fruit juices, or any other component known in the art as a component of, or additive to, a dairy product.

The terms "fermented dairy product" or "fermented milk product" as used herein is to be understood as any dairy product wherein any type of fermentation forms part of the production process. Examples of fermented dairy products are products like yoghurt, buttermilk, creme fraiche, quark and fromage frais. A fermented dairy product may be produced by or include steps of any method known in the art.

The term "fermentation" as used herein refers to the conversion of carbohydrates into alcohols or acids through the action of a microorganism. In some embodiments fermentation according to the present invention comprises the conversion of lactose to lactic acid. In the context of the present invention, "microorganism" may include any bacterium or fungus being able to ferment the milk substrate.

The term "increased beta-galactosidase enzyme activity" as used herein refers to a relatively higher specific activity of a beta-galactosidase enzyme in comparison to a reference sequence.

The term "peptide exhibiting beta-galactosidase enzyme activity" as used herein refers to any peptide, which has enzymatic activity to catalyze the hydrolysis of the disaccharide lactose into its component monosaccharides glucose and galactose. This peptide may also be referred to as a lactase or simply a beta-galactosidase (EC: 3.2.1.23).

The terms "peptide" and "oligopeptide" as used in the context of this present application are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All peptide and polypeptide formulas or sequences herein are written from left to right and in the direction from amino terminus to carboxy terminus. "Proteins" as used herein refers to peptide sequences as they are produced by some host organism and may include posttranslational modification, such as added glycans.

The terms "amino acid" or "amino acid sequence," as used herein, refer to an oligopeptide, peptide, polypeptide, or protein sequence, or a fragment of any of these, and to naturally occurring or synthetic molecules. In this context, "fragment" refer to fragments of a peptide exhibiting beta-galactosidase enzyme activity, which retain some enzymatic activity. Where "amino acid sequence" is recited herein to refer to an amino acid sequence of a naturally occurring protein molecule, "amino acid sequence" and like terms are not meant to limit the amino acid sequence to the complete native amino acid sequence associated with the recited peptide molecule.

Exemplary peptides of the invention also include fragments of at least about 50,100,150, 200, 250, 300, 350, 400, 450, 500, 550, 600, 650, 700, 750, 800 or more residues in length, or over the full length of an enzyme. Accordingly a "peptide fragment" or "enzymatically active fragment" of the invention are fragments that retain at least some functional enzymatic activity. Typically a peptide fragment of the invention will still contain the functional catalytic domain or other essential active sites of the peptide exhibiting beta-galactosidase enzyme activity. Other domains may be deleted.

Typically, the specific beta-galactosidase enzyme activity will be measured and indicated as μmol of glucose formed/min/mg of enzyme used. This specific value however will vary depending on conditions applied, such as temperature, and pH. Accordingly, values for beta-galactosidase enzyme activity may also be referred to as relative to a reference known enzyme, such as the beta-galactosidase enzyme defined by SEQ ID NO:34 OR SEQ ID NO:35.

Alternatively the specific beta-galactosidase enzyme activity may be measured and indicated as μM of glucose formed per second per μM of enzyme used. This specific value however will vary depending on conditions applied, such as temperature, and pH. ½

Unless otherwise stated the term "Sequence identity" for amino acids as used herein refers to the sequence identity calculated as $(n_{ref}-n_{dif}) \cdot 100/n_{ref}$, wherein $n_{dif}$ is the total number of non-identical residues in the two sequences when aligned and wherein $n_{ref}$ is the number of residues in one of the sequences.

In some embodiments the sequence identity is determined by conventional methods, e.g., Smith and Waterman, 1981, Adv. Appl. Math. 2:482, by the search for similarity method of Pearson & Lipman, 1988, Proc. Natl. Acad. Sci. USA 85:2444, using the CLUSTAL W algorithm of Thompson et al., 1994, Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., 1990, Mol. Biol. 215:403-10) for which software may be obtained through the National Center for Biotechnology Information www.ncbi.nlm.nih.gov/) may also be used. When using any of the aforementioned algorithms, the default parameters for "Window" length, gap penalty, etc., are used.

A peptide with a specific amino acid sequence as described herein may vary from a reference peptide sequence by any of amino acid substitutions, additions/insertions, or deletions.

Some embodiments according to the present invention refers to the use of a peptide with an amino acid sequence represented by SEQ ID NO:1-33 or a sequence with at least 80% sequence identity to any one of said sequences. In some embodiments this sequence identity may be at least about 81%, 82%, 83%, 84%, 85%, 86%, 87%, 88%, 89%, 90%, 91%, 92%, 93%, 94%, 95%, 96%, 97%, 98%, or 99%, such as a peptide with not more than 1, 2, 3, 4, 5, 6, 7, 8, 9, 10, 11, 12, 13, 14, 15, 16, 17, 18, 19, 20, 21, or 22 amino acid substitutions, additions or deletions as compared to any one reference amino acid sequence represented by SEQ ID NO:1-33. The invention also features biologically active fragments of the peptides according to the invention. Biologically active fragments of a peptide of the invention include peptides comprising amino acid sequences sufficiently identical to or derived from the amino acid sequence of peptide of the invention which include fewer amino acids than the full length protein but which exhibit a substantial part of the biological activity of the corresponding full-length peptide. Typically, biologically active fragments comprise a domain or motif with at least one activity of a variant protein of the invention. A biologically active fragment of a peptide of the invention can be a peptide which is, for example, 100, 200, 300, 400, 500, 600, 700, 800, 900, 1000 or more amino acids in length.

The term "host cell", as used herein, includes any cell type which is susceptible to transformation, transfection, transduction, and the like with a nucleic acid construct or expression vector comprising a polynucleotide encoding the peptides of the present invention. A host cell may be the cell type, where a specific enzyme is derived from or it may be an alternative cell type susceptible to the production of a specific enzyme. The term includes both wild type and attenuated strains.

Suitable host cell may be any bacteria including lactic acid within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Also included are lactic acid producing bacteria belonging to the group of anaerobic bacteria, bifidobacteria, i.e. *Bifidobacterium* spp., which are frequently used as food cultures alone or in combination with lactic acid bacteria. Also included within this definition are *Lactococcus lactis*, *Lactococcus lactis* subsp. *cremoris*, *Leuconostoc mesenteroides* subsp. *cremoris*, *Pseudoleuconostoc mesenteroides* subsp. *cremoris*, *Pediococcus pentosaceus*, *Lactococcus lactis* subsp. *lactis* biovar. *diacetylactis*, *Lactobacillus casei* subsp. *casei* and *Lactobacillus paracasei* subsp. *Paracasei* and thermophilic lactic acid bacterial species include as examples *Streptococcus thermophilus*, *Enterococcus faecium*, *Lactobacillus delbrueckii* subsp. *lactis*, *Lactobacillus helveticus*, *Lactobacillus delbrueckii* subsp. *bulgaricus* and *Lactobacillus acidophilus*. Other specific bacteria within this definition includes bacteria of the family Bifidobacteriaceae, such as from the genus *Bifidobacterium*, such as from a strain of *Bifidobacterium animalis* or *Bifidobacterium longum*, *bifidobacterium adolescentis*, *bifidobacterium bifidum*, *Bifidobacterium breve*, *bifidobacterium catenulatum*, *bifidobacterium infantus* or from the genus *Lactobacillus*, such as *L. sakei*, *L. amylovorus*, *L. delbrueckii* subsp. *Lactis*, and *L. helveticus*.

Also included within this definition of host cells include strain of *Agaricus*, e.g. *A. bisporus*; *Ascovaginospora*; *Aspergillus*, e.g. *A. niger, A. awamori, A. foetidus, A. japonicus, A. oryzae*; *Candida*; *Chaetomium*; *Chaetotomastia*; *Dictyostelium*, e.g. *D. discoideum*; *Kluveromyces*, e.g. *K. fragilis, K. lactis*; *Mucor*, e.g. *M. javanicus, M. mucedo, M. subtilissimus*; *Neurospora*, e.g. *N. crassa*; *Rhizomucor*, e.g. *R. pusillus*; *Rhizopus*, e.g. *R. arrhizus, R. japonicus, R. stolonifer*; *Sclerotinia*, e.g. *S. libertiana*; *Torula*; *Torulopsis*; *Trichophyton*, e.g. *T. rubrum*; *Whetzelinia*, e.g. *W. sclerotiorum*; *Bacillus*, e.g. *B. coagulans, B. circulans, B. megaterium, B. novalis, B. subtilis, B. pumilus, B. stearothermophilus, B. thuringiensis*; *Bifidobacterium*, e.g. *B. longum, B. bifidum, B. animalis*; *Chryseobacterium*; *Citrobacter*, e.g. *C. freundii*; *Clostridium*, e.g. *C. perfringens*; *Diplodia*, e.g. *D. gossypina*; *Enterobacter*, e.g. *E. aerogenes, E. cloacae Edwardsiella, E. tarda*; *Erwinia*, e.g. *E. herbicola*; *Escherichia*, e.g. *E. coli*; *Klebsiella*, e.g. *K. pneumoniae*; *Miriococcum*; *Myrothesium*; *Mucor*; *Neurospora*, e.g. *N. crassa*; *Proteus*, e.g. *P. vulgaris*; *Providencia*, e.g. *P. stuartii*; *Pycnoporus*, e.g. *Pycnoporus cinnabarinus, Pycnoporus sanguineus*; *Ruminococcus*, e.g. *R. torques*; *Salmonella*, e.g. *S. typhimurium*; *Serratia*, e.g. *S. liquefasciens, S. marcescens*; *Shigella*, e.g. *S. flexneri*; *Streptomyces*, e.g. *S. antibioticus, S. castaneoglobisporus, S. violeceoruber*; *Trametes*; *Trichoderma*, e.g. *T. reesei, T. viride*; *Yersinia*, e.g. *Y. enterocolitica*.

Specific Embodiments of the Invention

As described above the present invention relates to a peptide exhibiting beta-galactosidase enzyme activity, which has an amino acid sequence represented by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

Accordingly, in one embodiment the present invention relates to a peptide exhibiting beta-galactosidase enzyme activity, which has an amino acid sequence represented by SEQ ID NO: 1, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 2, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 3, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 4, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 5, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 6, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 7, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 8, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 9, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 10, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 11, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 12, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 13, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 14, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 15, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 16, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 17, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 18, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 19, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 20, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 21, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 22, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 23, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 24, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 25, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 26, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 27, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 28, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 29, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 30, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 31, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 32, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 33, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

In some embodiments the peptide according to the invention has a beta-galactosidase activity measured as µM of glucose formed per second per µM of enzyme under conditions as given in example 8 described herein at a temperature of about 4° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 4° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 4° C. and a pH of 6.7, which activity is higher than about 2, such as higher than about 4, such as higher than about 6, such as higher than about 8, such as higher than about 10, such as higher than about 12, such as higher than about 14, such as higher than about 16 µM of glucose formed per second per µM of enzyme.

In some embodiments the peptide according to the invention has a beta-galactosidase activity measured as µM of glucose formed per second per µM of enzyme under conditions as given in example 10 described herein at a temperature of about 4° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 4° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 4° C. and a pH of 5.5, which activity is higher than about 1, such as higher than about 2, such as higher than about 3, such as higher than about 4, such as higher than about 5, such as higher than about 6, such as higher than about 7, such as higher than about 8 µM of glucose formed per second per µM of enzyme.

In some embodiments the peptide according to the invention has a beta-galactosidase activity measured as µM of glucose formed per second per µM of enzyme under conditions as given in example 13 described herein at a temperature of about 4° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 4° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 4° C. and a pH of 4.5, which activity is higher than about 0.5, such as higher than about 1.0, such as higher than about 1.5, such as higher than about 2.0, such as higher than about 2.5, such as higher than about 3.0, such as higher than about 3.5, such as higher than about 4.0 µM of glucose formed per second per µM of enzyme.

In some embodiments the peptide according to the invention has a beta-galactosidase activity measured as µM of glucose formed per second per µM of enzyme under conditions as given in example 9 described herein at a temperature of about 43° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 43° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 43° C. and a pH of 6.7, which activity is higher than about 10, such as higher than about 20, such as higher than about 40, such as higher than about 60, such as higher than about 80, such as higher than about 100, such as higher than about 120, such as higher than about 140, such as higher than about 160 µM of glucose formed per second per µM of enzyme.

In some embodiments the peptide according to the invention has a beta-galactosidase activity measured as µM of glucose formed per second per µM of enzyme under conditions as given in example 12 described herein at a temperature of about 43° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 43° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 43° C. and a pH of 5.5, which activity is higher than about 5, such as higher than about 10, such as higher than about 15, such as higher than about 20, such as higher than about 25, such as higher than about 30, such as higher than about 35, such as higher than about 40, such as higher than about 45, such as higher than about 50, such as higher than about 55, such as higher than about 60 µM of glucose formed per second per µM of enzyme.

In some embodiments the peptide according to the invention has a beta-galactosidase activity measured as µM of glucose formed per second per µM of enzyme under conditions as given in example 15 described herein at a temperature of about 43° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 43° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 43° C. and a pH of 4.5, which activity is higher than about 1, such as higher than about 2, such as higher than about 3, such as higher than about 4, such as higher than about 5, such as higher than about 6, such as higher than about 7, such as higher than about 8, such as higher than about 9, such as higher than about 10, such as higher than about 11, such as higher than about 12 µM of glucose formed per second per µM of enzyme.

In some embodiments the peptide according to the invention has a beta-galactosidase activity measured as µM of glucose formed per second per µM of enzyme under conditions as given in example 6 described herein at a temperature of about 37° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 37° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 37° C. and a pH of 6.7, which activity is higher than about 10, such as higher than about 20, such as higher than about 30, such as higher than about 40, such as higher than about 50, such as higher than about 60, such as higher than about 70, such as higher than about 80, such as higher than about 90, such as higher than about 100, such as higher than about 110, such as higher than about 120, such as higher than about 130 µM of glucose formed per second per µM of enzyme.

In some embodiments the peptide according to the invention has a beta-galactosidase activity measured as µM of glucose formed per second per µM of enzyme under conditions as given in example 11 described herein at a temperature of about 37° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 37° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 37° C. and a pH of 5.5, which activity is higher than about 5, such as higher than about 10, such as higher than about 15, such as higher than about 20, such as higher than about 25, such as higher than about 30, such as higher than about 35, such as higher than about 40, such as higher than about 45, such as higher than about 50, such as higher than about 55, such as higher than about 60 µM of glucose formed per second per µM of enzyme.

In some embodiments the peptide according to the invention has a beta-galactosidase activity measured as µM of glucose formed per second per µM of enzyme under conditions as given in example 14 described herein at a temperature of about 37° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 37° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 37° C. and a pH of 4.5, which activity is higher than about 1, such as higher than about 2, such as higher than about 3, such as higher than about 4, such as higher than about 5, such as higher than about 6, such as higher than about 7, such as higher than about 8, such as higher than about 9, such as higher than about 10, such as higher than about 11, such as higher than about 12, such as higher than about 13, such as higher than about 14, such as higher than about 15, such as higher than about 16, such as higher than about 17, such as higher than about 18 µM of glucose formed per second per µM of enzyme.

In some embodiments the peptide according to the invention is derived from a bacteria of the genus *Bifidobacterium*, such as *Bifidobacterium adolescentis*, *Bifidobacterium bifidum*, *Bifidobacterium breve*, *Bifidobacterium catenulatum*, *Bifidobacterium longum* or from the genus *Lactobacillus*, such as *L. sakei*, *L. amylovorus*, *L. delbrueckii* subsp. *bulgaricus*, *L. delbrueckii* subsp. *lactis*, *L. delbrueckii* subsp. *Indicus*, *L. crispatus*, *L. reuteri*, *L helveticus* or from *Streptococcus thermophilus*.

In some embodiments the peptide according to the invention exhibit a galactose inhibition less than 60%, such as less than 55%, such as less than 50%, such as less than about 45%, such as less than about 40%.

As described above at part of the present invention relates to a method for producing a dairy product the method comprising the steps of
a) providing a milk-based substrate comprising lactose;
b) adding an peptide exhibiting beta-galactosidase activity and having an amino acid sequence represented by SEQ ID NO:1-33 or a sequence with at least 80% sequence identity to any one of said sequences to said milk-based substrate comprising lactose; and c) treating said milk-based substrate with said peptide exhibiting beta-galactosidase activity.

In some embodiments according to the present invention this peptide is derived from any one bacteria of the genus *Bifidobacterium*, such as *Bifidobacterium adolescentis*, *Bifidobacterium bifidum*, *Bifidobacterium breve*, *Bifidobacterium catenulatum*, *Bifidobacterium longum* or from the genus *Lactobacillus*, such as *L. sakei*, *L. amylovorus*, *L. delbrueckii* subsp. *bulgaricus*, *L. delbrueckii* subsp. *lactis*, *L. delbrueckii* subsp. *Indicus*, *L. crispatus*, *L. reuteri*, *L. helveticus* or from *Streptococcus thermophilus*.

In some embodiments according to the present invention step c) takes place at a pH within a range of 3-10, such as within a range of 3-9, such as within a range of 3-8, such as within a range of 3-7, such as within a range of 3-6, such as within a range of 3-5, such as within a range of 3-4, such as within a range of 4-10, such as within a range of 4-9, such as within a range of 4-8, such as within a range of 4-7, such as within a range of 4-6, such as within a range of 4-5, such as within a range of 5-10, such as within a range of 5-9, such as within a range of 5-8, such as within a range of 5-7, such as within a range of 5-6, such as within a range of 6-10, such as within a range of 6-9, such as within a range of 6-8, such as within a range of 6-7.

In some embodiments according to the present invention step c) or a part of step c) takes place at a temperature of not more than about 25° C., such as not more than about 20° C., such as not more than about 18° C., such as not more than about 16° C., such as not more than about 14° C., such as not more than about 12° C., such as not more than about 10° C., such as not more than about 8° C., such as not more than about 7° C., such as not more than about 6° C., such as not more than about 5° C., such as not more than about 4° C., such as not more than about 3° C., such as not more than about 2° C.

In some embodiments according to the present invention step c) or a part of step c) takes place at a temperature of at least about 25° C., such as at least about 30° C., such as at least about 35° C., such as at least about 40° C., such as at least about 45° C., such as at least about 50° C., such as at least about 55° C., such as at least about 60° C., such as at least about 65° C., such as at least about 70° C., such as at least about 75° C., such as at least about 80° C., such as at least about 85° C., such as at least about 90° C., such as at least about 95° C., such as at least about 100° C., such as at least about 110° C., such as at least about 120° C., such as at least about 130° C., such as at least about 120° C., such as at least about 130° C., such as at least about 135° C., such as at least about 140° C.

In some embodiments according to the present invention the dairy product is selected from the group consisting of lactose-free milk, low-lactose milk, yoghurt, cheese, fermented milk products, dietary supplement and probiotic dietary products.

In some embodiments according to the present invention the milk-based substrate is selected from fresh milk or raw milk obtained directly from a step of pasteurization, milk obtained directly after a step of ultra-heat treatment (UHT), or milk obtained directly after a step of fermentation.

In some embodiments according to the present invention the galactose inhibition of the peptide used is less than 60%, such as less than 55%, such as less than 50%, such as less than about 45%, such as less than about 40%.

In some embodiments according to the present invention the dairy product is fermented milk product and said step b) is performed during or prior to fermentation.

In some embodiments according to the present invention the method does not require the addition of further enzyme after fermentation.

In some embodiments according to the present invention the dairy product is fermented milk product and said step b) is performed immediately following fermentation.

In some embodiments according to the present invention the dairy product is fresh milk and said step b) is performed prior to, in conjunction with, or immediately following a step of pasteurization.

In some embodiments according to the present invention the dairy product is ultra-heat treatment (UHT) milk and said step b) is performed prior to, in conjunction with, or immediately following a step of ultra-heat treatment.

In some embodiments according to the present invention step c) is started at a temperature of between 40° C. and 100° C., such as at a temperature of between 50° C. and 100° C. such as at a temperature of between 60° C. and 100° C., such as at a temperature of between 70° C. and 100° C., such as at a temperature of between 80° C. and 100° C., such as at a temperature of between 40° C. and 90° C., such as at a temperature of between 40° C. and 80° C., such as at a temperature of between 40° C. and 70° C., such as at a temperature of between 40° C. and 60° C., such as at a temperature of between 40° C. and 50° C.

In some embodiments according to the present invention the peptide when hydrolyzing the lactose in the milk-based substrate has a ratio of lactase to transgalactosylase activity of more than 1:1.

In some embodiments according to the present invention less than 80% of the lactose has been hydrolyzed when step c) is completed, and wherein more than 90% of the lactose has been hydrolyzed after one week.

Numbered Embodiments

1. A peptide exhibiting beta-galactosidase enzyme activity, which has an amino acid sequence represented by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or enzymatically active fragments thereof, or an amino acid sequence of any one thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

2. A dimeric peptide exhibiting beta-galactosidase enzyme activity, which dimeric peptide consist of two peptides having an amino acid sequence represented by SEQ ID NO: 2 and 3, 5 and 6, 20 and 21, 23 and 24, 26 and 27, or 28 and 29; or enzymatically active fragments thereof, or an amino acid sequence of any one thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

3. The peptide or dimeric peptide according to embodiments 1 or 2, which has a beta-galactosidase activity measured as μM of glucose formed per second per μM of enzyme under conditions as given in example 8 described herein at a temperature of about 4° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

4. The peptide or dimeric peptide according to any one of embodiments 1-3, which has a beta-galactosidase activity measured as μM of glucose formed per second per μM of enzyme under conditions as given in example 10 described herein at a temperature of about 4° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

5. The peptide or dimeric peptide according to any one of embodiments 1-4, which has a beta-galactosidase activity measured as μM of glucose formed per second per μM of enzyme under conditions as given in example 13 described herein at a temperature of about 4° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

6. The peptide or dimeric peptide according to any one of embodiments 1-5, which has a beta-galactosidase activity measured as μM of glucose formed per second per μM of enzyme under conditions as given in example 9 described herein at a temperature of about 43° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

7. The peptide or dimeric peptide according to any one of embodiments 1-6, which has a beta-galactosidase activity measured as μM of glucose formed per second per μM of enzyme under conditions as given in example 12 described herein at a temperature of about 43° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

8. The peptide or dimeric peptide according to any one of embodiments 1-7, which has a beta-galactosidase activity measured as µM of glucose formed per second per µM of enzyme under conditions as given in example 15 described herein at a temperature of about 43° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

9. The peptide or dimeric peptide according to any one of embodiments 1-8, which has a beta-galactosidase activity measured as µM of glucose formed per second per µM of enzyme under conditions as given in example 6 described herein at a temperature of about 37° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

10. The peptide or dimeric peptide according to any one of embodiments 1-9, which has a beta-galactosidase activity measured as µM of glucose formed per second per µM of enzyme under conditions as given in example 11 described herein at a temperature of about 37° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

11. The peptide or dimeric peptide according to any one of embodiments 1-10, which has a beta-galactosidase activity measured as µM of glucose formed per second per µM of enzyme under conditions as given in example 14 described herein at a temperature of about 37° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

12. The peptide or dimeric peptide according to any one of embodiments 1-11, derived from a bacteria of the genus *Bifidobacterium*, such as *Bifidobacterium adolescentis*, *Bifidobacterium bifidum*, *Bifidobacterium breve*, *Bifidobacterium catenulatum*, *Bifidobacterium longum* or from the genus *Lactobacillus*, such as *L. sakei*, *L. amylovorus*, *L. delbrueckii* subsp. *bulgaricus*, *L. delbrueckii* subsp. *lactis*, *L. delbrueckii* subsp. *Indicus*, *L. crispatus*, *L. reuteri*, *L. helveticus* or from *Streptococcus thermophilus*.

13. The peptide or dimeric peptide according to any one of embodiments 1-12, wherein said peptide or dimeric peptide exhibit a galactose inhibition less than 60%, such as less than 55%, such as less than 50%, such as less than about 45%, such as less than about 40%.

14. A nucleotide sequence which encodes a peptide or dimeric peptide as defined in any one of embodiments 1-13.

15. A host cell comprising a nucleotide sequence as defined in embodiment 14.

16. A method for producing a peptide or dimeric peptide as defined in any one of the embodiments 1-13, which method comprises the expression of a vector containing a nucleotide sequence as defined in embodiment 14 in a suitable host cell; and purifying said peptide or dimeric peptide from the expression products of said host cell.

17. A method for reducing the lactose content in a composition containing lactose, such as in a dairy products, comprising the step of contacting said composition with a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or enzymatically active fragments thereof, or any sequence with at least 80% sequence identity to any one of said sequences or enzymatically active fragments; or a host cell expressing any one of said peptide or dimeric peptide, at a pH ranging from 3-10 and at a temperature ranging from 0° C.-140° C.

18. The method according to embodiment 17, wherein said composition is a dairy product selected from the group consisting of lactose-free milk, low-lactose milk, yoghurt, cheese, fermented milk products, dietary supplement and probiotic dietary products.

19. The method according to any one of embodiments 17-18, wherein said host cell is any one selected from a bacteria of the genus *Bifidobacterium*, such as *Bifidobacterium adolescentis*, *Bifidobacterium bifidum*, *Bifidobacterium breve*, *Bifidobacterium catenulatum*, *Bifidobacterium longum* or from the genus *Lactobacillus*, such as *L. sakei*, *L. amylovorus*, *L. delbrueckii* subsp. *bulgaricus*, *L. delbrueckii* subsp. *lactis*, *L. delbrueckii* subsp. *Indicus*, *L. crispatus*, *L. reuteri*, *L. helveticus* or from *Streptococcus thermophilus*.

20. The method according to any one of embodiments 17-19, wherein the lactose concentration is reduced to less than about 1%, such as to less than about 0.1% or lower, such as to less than about 0.01%.

21. Use of a peptide or dimeric peptide exhibiting beta-galactosidase enzyme activity, which peptide has an amino acid sequence represented by SEQ ID NO: 1-33, or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences; or a host cell expressing any one of said peptide or dimeric peptide for producing a dairy product with a reduced lactose content.

22. The use according to embodiment 21, wherein said dairy product is selected from the group consisting of lactose-free milk, low-lactose milk, yoghurt, cheese, fermented milk products, dietary supplement and probiotic dietary products.

23. The use according to any one of embodiments 21-22, wherein said host cell is any one selected from a bacteria of the genus *Bifidobacterium*, such as *Bifidobacterium adolescentis, Bifidobacterium bifidum, Bifidobacterium breve, Bifidobacterium catenulatum, Bifidobacterium longum* or from the genus *Lactobacillus*, such as *L. sakei, L. amylovorus, L. delbrueckii* subsp. *bulgaricus, L. delbrueckii* subsp. *lactis, L. delbrueckii* subsp. *Indicus, L. crispatus, L. reuteri, L. helveticus* or from *Streptococcus thermophilus*.

24. A method for producing a dairy product the method comprising the steps of
a) providing a milk-based substrate comprising lactose;
b) adding an peptide or dimeric peptide exhibiting beta-galactosidase activity, which peptide has an amino acid sequence represented by SEQ ID NO:1-33; or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences to said milk-based substrate comprising lactose; and
c) treating said milk-based substrate with said peptide or dimeric peptide exhibiting beta-galactosidase activity.

25. The method according to embodiment 24, wherein said peptide or dimeric peptide is derived from any one bacteria of the genus *Bifidobacterium*, such as *Bifidobacterium adolescentis, Bifidobacterium bifidum, Bifidobacterium breve, Bifidobacterium catenulatum, Bifidobacterium longum* or from the genus *Lactobacillus*, such as *L. sakei, L. amylovorus, L. delbrueckii* subsp. *bulgaricus, L. delbrueckii* subsp. *lactis, L. delbrueckii* subsp. *Indicus, L. crispatus, L. reuteri, L. helveticus* or from *Streptococcus thermophilus*.

26. The method according to any one of embodiments 24-25, wherein step c) takes place at a pH within a range of 3-10, such as within a range of 3-9, such as within a range of 3-8, such as within a range of 3-7, such as within a range of 3-6, such as within a range of 3-5, such as within a range of 3-4, such as within a range of 4-10, such as within a range of 4-9, such as within a range of 4-8, such as within a range of 4-7, such as within a range of 4-6, such as within a range of 4-5, such as within a range of 5-10, such as within a range of 5-9, such as within a range of 5-8, such as within a range of 5-7, such as within a range of 5-6, such as within a range of 6-10, such as within a range of 6-9, such as within a range of 6-8, such as within a range of 6-7.

27. The method according to any one of embodiments 24-26, wherein step c) or a part of step c) takes place at a temperature of not more than about 25° C., such as not more than about 20° C., such as not more than about 18° C., such as not more than about 16° C., such as not more than about 14° C., such as not more than about 12° C., such as not more than about 10° C., such as not more than about 8° C., such as not more than about 7° C., such as not more than about 6° C., such as not more than about 5° C., such as not more than about 4° C., such as not more than about 3° C., such as not more than about 2° C.

28. The method according to any one of embodiments 24-27, wherein step c) or a part of step c) takes place at a temperature of at least about 25° C., such as at least about 30° C., such as at least about 35° C., such as at least about 40° C., such as at least about 45° C., such as at least about 50° C., such as at least about 55° C., such as at least about 60° C., such as at least about 65° C., such as at least about 70° C., such as at least about 75° C., such as at least about 80° C., such as at least about 85° C., such as at least about 90° C., such as at least about 95° C., such as at least about 100° C., such as at least about 110° C., such as at least about 120° C., such as at least about 130° C., such as at least about 120° C., such as at least about 130° C., such as at least about 135° C., such as at least about 140° C.

29. The method according to any one of embodiments 24-28, wherein said dairy product is selected from the group consisting of lactose-free milk, low-lactose milk, yoghurt, cheese, fermented milk products, dietary supplement and probiotic dietary products.

30. The method according to any one of embodiments 24-29, wherein said milk-based substrate is selected from fresh milk or raw milk obtained directly from a step of pasteurization, milk obtained directly after a step of ultra-heat treatment (UHT), or milk obtained directly after a step of fermentation.

31. The method according to any one of embodiments 24-30, wherein the galactose inhibition of said peptide or dimeric peptide is less than 60%, such as less than 55%, such as less than 50%, such as less than about 45%, such as less than about 40%.

32. The method according to any one of embodiments 24-31, wherein said dairy product is fermented milk product and said step b) is performed during or prior to fermentation.

33. The method according to embodiment 32, which method does not require the addition of further enzyme after fermentation.

34. The method according to any one of embodiments 24-31, wherein said dairy product is fermented milk product and said step b) is performed immediately following fermentation.

35. The method according to any one of embodiments 24-31, wherein said dairy product is fresh milk and said step b) is performed prior to, in conjunction with, or immediately following a step of pasteurization.

36. The method according to any one of embodiments 24-31, wherein said dairy product is ultra-heat treatment (UHT) milk and said step b) is performed prior to, in conjunction with, or immediately following a step of ultra-heat treatment.

37. The method according to any one of embodiments 24-36, wherein step c) is started at a temperature of between 40° C. and 100° C., such as at a temperature of between 50° C. and 100° C. such as at a temperature of between 60° C. and 100° C., such as at a temperature of between 70° C. and 100° C., such as at a temperature of between 80° C. and 100° C., such as at a temperature of between 40° C. and 90° C., such as at a temperature of between 40° C. and 80° C., such as at a temperature of between 40° C. and 70° C., such as at a temperature of between 40° C. and 60° C., such as at a temperature of between 40° C. and 50° C.

38. The method according to any one of embodiments 24-37, wherein the peptide or dimeric peptide when hydrolysing the lactose in the milk-based substrate has a ratio of lactase to transgalactosylase activity of more than 1:1.

39. The method according to any one of embodiments 24-38, wherein less than 80% of the lactose has been hydrolyzed when step c) is completed, and wherein more than 90% of the lactose has been hydrolyzed after one week.

40. A dairy product prepared by a method as defined in any one of embodiments 24-39.

41. A food product, such as a dairy product comprising a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences.

42. A food product, such as a dairy product comprising a host cell expressing a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences.

43. The food product according to embodiment 42, which is selected from beverages, infant foods, cereals, bread, biscuits, confectionary, cakes, food supplements, dietary supplements, probiotic comestible products, prebiotic comestible products, animal feeds, poultry feeds and medicaments, or a dairy product selected from the group consisting of lactose-free milk, low-lactose milk, dried milk powder, baby milks, yoghurt, ice cream, cheese, fermented milk products, dietary supplement and probiotic dietary products.

Sequences

TABLE 1

The gene numbers with corresponding sequence identification number.

| Gene number | Sequence Identity number | Species name |
|---|---|---|
| G4 | SEQ ID No 1 | *Bifidobacterium adolescentis* |
| G16 | SEQ ID No 2 (domain a) SEQ ID No 3 (domain b) | *Lactobacillus sakei* |
| G35 | SEQ ID No 4 | *Bifidobacterium adolescentis* |
| G40 | SEQ ID No 5 (domain a) SEQ ID No 6 (domain b) | *Lactobacillus amylovorus* |
| G44 | SEQ ID No 7 | *Bifidobacterium bifidum* |
| G51 | SEQ ID No 8 | *Bifidobacterium bifidum* |
| G57 | SEQ ID No 9 | *Bifidobacterium breve* |
| G62 | SEQ ID No 10 | *Bifidobacterium catenulatum* |

TABLE 1-continued

The gene numbers with corresponding sequence identification number.

| Gene number | Sequence Identity number | Species name |
|---|---|---|
| G66 | SEQ ID No 11 | *Bifidobacterium catenulatum* |
| G83 | SEQ ID No 12 | *Lactobacillus delbrueckii* subsp. *bulparicus* |
| G84 | SEQ ID No 13 | *Lactobacillus delbrueckii* subsp. *lactis* |
| G95 | SEQ ID No 14 | *Lactobacillus delbrueckii* subsp. *buiparicus* |
| G100 | SEQ ID No 15 | *Lactobacillus delbrueckii* subsp. *buiparicus* |
| G104 | SEQ ID No 16 | *Lactobacillus delbrueckii* subsp. *lactis* |
| G108 | SEQ ID No 17 | *Lactobacillus delbrueckii* subsp. *buiparicus* |
| G109 | SEQ ID No 18 | *Lactobacillus delbrueckii* subsp. *buiparicus* |
| G118 | SEQ ID No 19 | *Lactobacillus delbrueckii* subsp. *lactis* |
| G145 | SEQ ID No 20 (domain a) SEQ ID No 21 (domain b) | *Lactobacillus helvaticus* |
| G158 | SEQ ID No 22 | *Bifidobacterium lonpum* |
| G224 | SEQ ID No 23 (domain a) SEQ ID No 24 (domain b) | *Lactobacillus reuteri* |
| G256 | SEQ ID No 25 | *Lactobacillus delbrueckii* subsp. *lactis* |
| G282 | SEQ ID No 26 (domain a) SEQ ID No 27 (domain b) | *Lactobacillus helvaticus* |
| G334 | SEQ ID No 28 (domain a) SEQ ID No 29 (domain b) | *Lactobacillus crispatus* |
| G335 | SEQ ID No 30 | *Streptococcus thermophilus* |
| G336 | SEQ ID No 31 | *Lactobacillus delbrueckii* subsp. *indicus* |
| G11 | SEQ ID No 32 | *Bifidobacterium adolescentis* |
| G33 | SEQ ID No 33 | *Bifidobacterium adolescentis* |
| G600 | SEQ ID No 34 | *Bifidobacterium bifidum* |
| G500 | SEQ ID No 35 | *Kluyveromyces lactis* |

```
SEQ ID No. 1
MADTAELAIVHATTASASWLTDPTVFAANRKPAHSSHRYVIGETSEPKQSLDGEWKVRIEQARNVDVESAPFAAVDFEDGDFG

AIEVPGHLQMAGYLKNKYVNIQYPWDGHEDPQAPNIPENNHVATYRRRFALDQALARTLENDGTVSLTFHGAATAIYVWLDGT

FVGYGEDGFTPSEFDVTEALRNGNGNAADSPEAEHTLTVACYEYSSAWSLEDQDFWRLHGLFRTVELAAQPHTHVETVQLEAD

YTAADTAGTADTAELNAALTLRNSADAMTIESTLRDGDGNVVSESTQACNGEIALNSGKMTNIAPWSAESPTLYTLTVRVVGH

DGAITETVTQKIGFRTFRIENGIMTLNGKRIVFKGADRHEFDAKRGRAITREDMLSDVVFCKRHNINAIRTSHYPNQEYWYDL

CDEYGLYLIDETNMETHGTWVANNVERPEDGTPGSRPEWEGACVDRINSMMRRDYNHPSVLIWSLGNESSAGEVFRAMYRHAH

TIDPNRPVHYEGSVHMREFEDVTDIESRMYAHADEIERYLNDGSPAHTDGPKKPYISCEYMHAMGNSCGNMDEYTALERYPMY

QGGFTWDFIDQAIETKLPDGTTRMCYGGDFGDRPSDYEFSGDGLLFADRTPSPKAQEVKQLYANVKIVVSVDEARITNDNLFV

STGDYRFVLRILADGKPVWSTTRRFDVAAGESASFEVDWPVDDYRSNAEELVLEVSQQLGNACDWAPAGYELAFGQCVVAGAK

TTADAVDAAGAPADGTVTLGRWNAGVRGQGREALFSRTQGGMVSYTFGEREFVLRRPSITTFRPLTDNDRGAGHAFERAAWAV

AGKYARCVDCAIANRGENAVEATYTYELAIPQRTKVTVRYVADTAGLVSLDVEYPGEKNGDLPTIPAFGIEWALPVEYANLRF

YGAGPEETYADRRHAKLGVWSTTAGDDCAPYLLPQETGNHEDVRWAEITDDSGHGVRVKRGAGAKPFAMSLLPYSSTMLEEAL

HQDELPKPRHMFLRLLAAQMGVGGDDSWMSPVHEQYQLPADQPLSLNVQLKLF (G16 Domain a)
                                                                        SEQ ID No. 2
MQPNIQWLDTPAVFRVGQLPAHSDHRYYATLAEMAQQQSSFEQSLNGTWQFHYSVNAASRPKSFYELAFDAQDFEPITVPQHI ELAGYEQLHYINTMYPWEGHYYRRPAFSTSDDKQHLGMFSEADYNPVGSYLHHFDLTPALRNQRVIIRFEGVEQAMYVWLNGQ FIGYAEDSFTPSEFDLTPYLKETDNCLAVEVHKRSSAAFIEDQDFFRFFGIFRDVKLLAKPRTHLEDLWVIPEYDVVQQTGQV
```

-continued

KLRLQFSGDENRVHLRIRDQHQIILTADLTSAAQVNGLYKMPELVQAWSNQTPNLYTLELEVVDQAGETIEISQQPFGFRKIE

IKDKVMLLNGKRLVINGVNRHEWHPETGRTITAEDEAWDIACMQRNHINAVRTSHYPDRLSFYNGCDQAGIYMMAETNLESHG

SWQKMGAVEPSWNVPGSYDEWEAATLDRARTNFETFKNHVSILFWSLGNESYAGSVLEKMNAYYKQQDPTRLVHYEGVFRAPE

YKATISDVESRMYATPAEIKAYLDNAPQKPFILCEYMHDMGNSLGGMQSYIDLLSQYDMYQGGFIWDFIDQALLVTDPVTGQR

ELRYGGDFDDRPSDYEFSGDGLVFATRDEKPAMQEVRYYYGEHK (G16 Domain b)

SEQ ID No. 3

MKNQQVRRLDTIMANTNKRLAVIFGDVTLGLKGPDFHYLFSYQTGGPESIRIQGKEWLYRSPKPTFWRATTDNDRGNQFPLKS

GMWLAADQFIACQSITVAIDGQTIPLPIAPENNRYCGQETAQEVTVTYTYQTITTPQTTVEVSYTIQASGKIRVAVTYHGQAG

LPSLPVFGLRFVMPTPATRFIYQGLSGETYPDRMAGGMAGEYEVTGLPVTPYLVPQDCGVHMATDWVTIYRQAVLDNRLREPV

ETGLKFKMVDQPFAFSCLPYTAEELENATHHSELPAPHRTVLSLLGAVRGVGGIDSWGSDVEAYYQIDATQDHHLEFETSF

SEQ ID No. 4

MADTAELAIVHATTASASWLTDPTVFAANRKPAHSSHRYVIGETSEPKQSLDGEWKVRIEQARNVDVESAPFAAVDFEDGDFG

AIEVPGHLQMAGYLKNKYVNIQYPWDGHEDPQAPNIPENNHVAIYRRRFALDAQLARTLENDGTVSLTFHGAATAIYVWLDGT

FVGYGEDGFTPSEFDVTEALRNGNGNAADSPEAEHTLTVACYEYSSASWLEDQDFWRLHGLFRTVELAAQPHTHVETVQLEAD

YTAADTAGTADTAELNAALTLRNPADAMTIESTLRDGDGNVVWESTQACNGEIALNSGKMTNIAPWSAESPTLYTLTVRVVGH

DGAITETVTQKIGFRTFRIENGIMTLNGKRIVFKGADRHEFDAKRGRAITREDMLSDVVFCKRHNINARITSHYPNQEYWYDL

CDEYGLYLIDETNMETHGTWVANNVERPGEDIPGSRPEWEGACVDRINSMMRRDYNHPSVLIWSLGNESSAGEVFRMAYRHAH

TIDPNRPVHYEGSVHMREFEDVTDIESRMYAHADEIERYLNDGSPAHTDGPKKPYISCEYMHAMGNSCGNMDEYTALERYPMY

QGGFIWDFIDQAIETKLPDGTTRMCYGGDFGDRPSDYEFSGDGLLFADRTPSPKAQEVKQLYANVKIAVSVDEARITNDNLFV

STGDYRFVLRILADGKPVWSTTRRFDVAAGESASFEVDWPVDDYRSNAEELVLEVSQLLGNACDWAPAGYELAFGQCVVAGAK

TTADAVDAAGAPADGTVTLGRWNAGVRGQGREALFSRTQGGMVSYTFGEREFVLRRPSITTFRPLTDNDRGAGHAFERAAWAV

AGKYARCVDCAIANRGENAVEATYTYELAIPQRTKVTVRYVADTAGLVSLDVEYPGEKNGDLPTIPAFGIEWALPVEYANLRF

YGAGPEETYADRRHAKLGVWSTTAGDDCAPYLLPQETGNHEDVRWAEITDDSGHGVRVKRGAGAKPFAMSLLPYSSTMLEEAL

HQDELPKPRHMFLRLLAAQMGVGGDDSWMSPVHEQYALPADQPLSLNVQLKLF (G40 Domain a)

SEQ ID No. 5

MKANIKWLDDPEVFRINQLPAHSDHPFYKDYREWQNHSSSFKQSLNGAWQFHFSKDPQSRPIDFYKRSFDSSSFDTIPVPSEI

ELNGYAQNQYTNILYPWESKIYRKPAYTLGRGIKDGDFSQGKDNTVGSYLKHFDLNPALAGHDIHIQFEGVERAMYVYLNGHF

IGYAEDSFTPSEFDLTPYIQAKDNILAVEVFKHSTASWLEDQDMFRFSGIFRSVELLALPRTHLMDLDIKPTVVNDYHDGVFN

AKLHFMGKTSGNVHVLIEDIDGKTLLNKKLPLKSTVEIENETFANVHLWDNHDPYLYQLIIEVHDQDGKLVELIPYQFGFRKI

EITKDHVVLLNGKRLIINGVNRHEWDAKRGRSITLADMKQDIATFKHNNINAVRTCHYPNQIPWYYLCDQNGIYMMAENNLES

HGTWQKLGQVEATSNVPGSIPEWREVVVDRARSNYETFKNHTAILFWSLGNESYAGSNIAAMNKLYKDHDSSRLTHYEGVFHA

PEFKKEISDLESCMYLPPKEAEEYLQNPKKPLVECEYMHDMGTPDGGMGSYIKLIDKYPQYMGGFIWDFIDQALLVHDPVSGQ

DVLRYGGDFDDRHSDYEFSGDGLMFADRTPKPAMQEVRYYYGLHK (G40 Domain b)

SEQ ID No. 6
MAYTNNLHVVYGEASLGVNGQDFAYLFSYERGGLESLKIKDKEWLYRTPTPTFWRATTDNDRGSGFNQKAAQWLGADMFTKCV

GIHVQVDDHRFDELPVAPINNQFSNQEFAHEVKVAFDYETLTTPATKVKIIYNINDFGHMTITMHYFGKKGLPPLPVIGMRFI

MPTKAKSFDYTGLSGETYPDRMAGAERGTFHIDGLPVTKYLVPQENGMHMQTNELVITRNSTQNNADKDGDFSLKITQTKQPF

NFSLLPYTAEELENATHIEELPLARRSVLVIAGAVRGVGGIDSWGSDVEEQYHIDPQEDHEFSFTLN

SEQ ID No. 7
MNTTDDQRKNGDPIVSPSIPTTAWLADPRVYAVHRLDAHSDHACWSRSPVDGESTDLRQSLDGEWRVRVETAPTGRFPDGTSD

GPDWESDVSPLFAAPGFDDSSFSRVQVPSHLETAGLLAPQYVNVQYPWDGHEDPKAPAIPEEGHVAVYRREFDADGEVAQAVR

```
                                                      -continued
EGRPVTLTFQGAATAIYVWLNGSFIGYAEDSFTPSEFDVEDAIKVDGNVLAVACYEYSSASWLEDQDFWRLHGLERSVELNAR PAAHVADLHADADWDLATSRGSLSLDVLIDGAANAATADFALRDKNGTIVWRTATKADGTLEAEAEIDDAAPWSAERPDLYEL SVTLLDADGAVLETARTRIGFREVAIEDGILKENGKRLVFRGVNRHEFDCRRGRAITEEDMLWDIRFMKRHNINAVRTSHYPN QSRWYELCDEYGIYLIDEINLETHGSWNSPGDIPVGTSVPGDDEAWLGACIDRLDSMILRDRNHPSVEVWSLGNESYAGEVLK AMSAHAHQLDPGRPVHYEGVNWNHAYDGISDFESRMYAKPAEIQDWLEHGDERGEASKPFVSCEYMHAMGNSCGGESEFIDLE RYERYSGGFIWDYIDQGLVQRLPDGSERESVGGEWGDRPEDYEFVGNGIVFADRTPSPKAQEVKQLYSPVKLAPDGHGVTIEN RNLFAGTDGYVFAARLLEDGHEIWHADYRFDVAAGDTQHHDIAFPDIDADGDTREVIYEVDLLLAEATAWAPAGYELAFGQLT GTLNPEQDITETSHDDDGRATRILSRWNAGIRRDDEEILLSRTQGGIVSWKRDDREMVIRRPELVTFRPLTDNDRGNHSGFDR AAWFAAGRYAIVTETKIHESDDGLVAEYQYELADPNHTPVSVTYHVNSDMRMQLTVEYPGNATDMASEPAFGIEWELPGEYDR LRYYGPGPEETYRDRKQGGKLGIWDATAKASMAPYLMVQETGSHEDVRWLEATDIQGEGLRVTQRGDRHFTASLLPWNEYTIE

AARRHEDLPKPRHNYLRLLAAQMGVGGDDSWGAPVHTAYQLPAGRPLTLDVNLELI

SEQ ID No. 8
MNTTDDQRKNGDPIVSPSIPTTAWLADPRVYAVHRLDAHSDHACWSRSPVDGESTDLRQSLDGEWRVRVETAPTGRFPDGTSD

GPDWESDVSPLFAAPGFDDSSFSRVQVPSHLETAGLLAPQYVNVQYPWDGHEDPKAPAIPEEGHVAVYRREFDADGEVAQAVR

EGRPVTLTFQGAATAIYVWLNGSFIGYAEDSFTPSEFDVSDAIKVDGNVLAVACYEYSSASWLEDQDFWRLHGLFRSVELNAR

PAAHVADLHADADWDLATSRGSLSLDVLIDGAANAATADFALWDKNGTIVWHIVTKADGTLEAEAEIDDAAPWSAERPDLYEL

SVTLLDADGAVLETARTRIGFREVAIEDGILKENGKRLVFRGVNRHEFDCRRGRAITEEDMLWDIRFMKRHNINAVRTSHYPN

QSRWYELCDEYGIYLIDEINLETHGSWNSPGDIPVGTSVPGDDEAWLGACIDRLDSMILRDRNHPSVEVWSLGNESYAGEVLK

AMSAHAHRLDPGRPVHYEGVNWNHAYDGISDFESRMYAKPAEIQDWLEHGDERGEASKPFVSCEYMHAMGNSCGGESEFIDLE

RYERYSGGFIWDYIDQGLVQRLPDGSERESVGGEWGDRPEDYEFVGNGIVFADRTPSPKAQEVKQLYSPVKLAPDGHGVTIEN

RNLFAGTDGYVFAARLLEDGHEIWHADYRFDVAAGDTQHHDIAFPDIDADGDTREVIYEVDLLLAEATAWAPAGYELAFGQLT

GTLNPEQDITETSHDDDGRATRTLSRWNAGIRRDDKEILLSRTQGGIVSWKRDDREMVIRRPELVTFRPLTDNDRGNHSGFDR

AAWFAAGRYAIVTEIKIHESDDGLVAEYQYELADPNHTPVSVTYHVNSDMRMQLTVEYPGNATDMASEPAFGIEWELPGEYDR

LRYYGPGPEETYRDRKQGGKLGIWDATAKASMAPYLMVQETGSHELVRWLEATDIQGEGLRVTQRGDRHFTASLLPWNEYMIE

AARRHEDLPEPRHNYLRLLAAQMGVGGDDSWGAPVHTAYQLPAGRPLTLDVNLELI

SEQ ID No. 9
MTNSMQGKAXTIMINLQSAQQFSQAWLTDPRVFAVNRLAAHSSHKFYDHSPQCGEAMDLKQSLDGQWRVQMLDLADLADNELA

EAAFAQPGYDAAGFSPIEVPSALETKGFLNEQYVNQQYPWSGHESPVAPDVPKHNHVALYREEFSLEPKAAAVLEANKEAADD

AAKRRVTLTFQGAATAIVVWLNGAFIGYAEDSFTPSEFDVTDVLRDGVNTLAVACFEFSSASWLEDQDFWRLHGIFRSVELEA

QPLVHVNDLRVLADYDHTIGEGSLDVVALLRNAGTAAAVAATVLDAAGNTVWHSKLTAGADAETLTVKANVGKVNPWSAEEPT

LYTLQVVATDAAGQVIEAALQRIGFRHFAIEDGLMKLNGKRIVFKCVDRHEFDARTGRTIAEADMIEDIESFKRLNINAVRTS

HYPNETRWYELCDEYGIYVLDETNLETHGSWEDPGDVFQPARAEPGSKDEWRAACVDRTASMVRRDYNHPSVVIWSLGNEAFG

GDVFYSMRDTVHENDPFRPVHYEGTFNDPEFSAATDIMSRMYAKPDEIVKLYLGEDGKKPYISCEYSHSMGNSTGGLHLYTEL

ERYPLYQGGFIWDYVDQALWQDCGNGTERLAYGGDFEDRPNDYEFSGDGVMFADRTPSPKAQEVKQLYANVKLVPDESGVTIT

NDNLFISTASSLFTARVLVDGAERWHANYRFDVPAGETVREPIAFPKVTDLVALSGSAEVTYEVDQREAEATDWAPAGYELTF

GQYVAAVSFDDGAADAVVAGDAEVAADGFNAGIHTDFGEVLLSKTQGGMVSFKRDGREMVIRRPNLTTFRALTDNDRGNGSGF

ERAQWMAAGRYARVIGTSVEETADGKGLKATYSYELADAKHTPVTVHYEVDAALRVHLTVEYPGEADAATLPAFGEEWELPKQ

YDRLRFYGLGPEETYADRLHGAKLGVFSRIAAEDCAPYLLPQEEGNHEQVRWAEITDEYGHGMRVTAAGGTRFATSLLPYSSL

MFEDALHQNELPKPRHTFLRLLAAQMGVGGDDTWGAPVHDEFQVPADQPLKLDVTLELI

SEQ ID No. 10
MTQRRSYRWPQPLAGQQARIWYGGDYNPDQWPEEVWDDDVRLMKKAGVNLVSVGIFSWAKIETSEGVYDFDWLDRIIDKLGEA

GIAVDLASATASPPMWLTQAHPEVLWKDYRGDVCQPGARQHWRPTSPVTREYALKLCRAMAEHYKGNPYVVAWHVSNEYGCHN
```

RFDYSEDAERAFRKWCEERYGTIDAVNDAWGEAFWAQRMNDFTEIVPPRFIGDGNFMNPGKLLDFKRFSSDALKAFYVAERDA

LAEICPDLPLTTNFMVSAAGSVLDYDDWGREVDFVSNDHYFIPGEAHLDELAFSASLVDGIARKDPWFLMEHSTSAVNWRPVN

YRKEPGQLVRDSLAHVAMGADAVCYFQWRQSKAGAEKFHSANVPHIGEDSAVFRDVCELGADLNTLADNGLLGTKLAKSKVAV

VFDYESEWATEHTATPTQKVHHVDEPLQWFRALADHGVTADVVPVSSNWDEYEVVVLPSVYILSEETTRRVRDYVVNGGRLIV

TYYTGLSDEXDHVWLGGYPGSIRDVVGVRVEEFMPMGDDFPGVPDCLGLSNGAVAHDIADVIGSVDGTATVLETFRDDPWTGM

DGAPAIVANTFGEGRSVYVGARLGRDGIAKSLPEIFESLGMAEEGENDSRVLRVEREGSDGSRFVFSFNRTHEAVQIPFEGKI

VVSSFAEVSGENVSIKPNGVIVTKQ

SEQ ID No. 11
MANSNRVEHASETWLTDATVFEVNRTPAHSNHKCFTHDPQSGEHSDLTQSLDGEWRVEIVQASDIDFNEEPFVAENFDDSSFC

RACVPGHLQMAGLLKNKYVNIQYPWDGHENPLEPNVPENNHVALYRRKFVVSKRLADTKESEGSVSIVFEGMATAIYVWVNGL

FAGYGEDGFTPNEFDITDLLHDGENVVAVACYEYSSASWLEDQDFWRLHGLFRSVELTAQPEVHVENMQLEADWDAESGTASL

DAALSVRNASDAATISATLKDSEGNVVWEASENADANTTFASGSLQGLEPWSAESPSLYELEVNVIDQAGNIVEAAVQKVGFR

RFRIENGIMTLNGKRIVFKGADRHEFDAKRGRSITEQDMIDDVIFCKRHNINAIRTSHYPNQERWYDLCDEYGIYLIDETNLE

THGSWCLPGDVVTAETAVPGSKAHWEGACVDRVNSMVRRDYNHPSVVIWSLGNESYTGDVFRAMYKHVHDIDPNRPVHYEGVT

KNRDYDDVTDIETRMYEHADVVEEYLKNDPQKPYISCEYMHAMGNSVGNLDEYIALERYPHYQGGFIWDFIDQAIYATQPDGS

TRLCYGGDFGDRPSDYEFSGNGLVFADRTPTPKAQEVKQLYSNVHIDVTDRSVSIKNDNLFISTGGYQFVLRILADGEPVWQS

ERRFDVPADSACTFDVEWPVDLYRANADELVLEVSQRLAEATDWAPAGYELAFGQTIVAGTKAAEDAALPADGIVTVGRWNAG

VQGSGREILLSRTQGGLVSYTFDGHEFVLRRPAITTFRALTDNDRGAGHGFERAQWMVAGRYARCVDNVIEQVDEDTLKAVYT

YELAEPQCTXVTVGYTADTTGRLNLHVEYPGESGELPTIPAFGEEWTLPVQYSNLRFFGAGPEETYQDRKHAKLGVWSEDAFK

DHAPYLMPQETGNHEEVRWAEITDENGHGLRVSRANGAAPFAVSLQPYSSFMIEEAQEQDELPAPKHMFLRVLAAQMGVGGDD

SWMSPVHSQYHITADQPISLDVNLELI

SEQ ID No. 12
MSNKLVKEKRVDQADLANLTDPEVYEVNTIPPHSDHESFQSQEELEEGASSLVQSLDGDWLIDYAENGQGPVNFYAEDFDDSN

FKSVKVPGNLELQGFGQPQYVNVQYPWDGSEEIFPPQIPSKNPLASYVRYFDLDEAFWDKEVSLKFDGAATAIYVWLNGHFVG

YGEDSFTPSZFMVTKFLKKENNRLAVALYKYSSASWLEDQDFWRMSGLFRSVTLQAKPRLHLEDLKLTASLTDNYQKGKLEVE

ANIAYRLPNASFKLEVRDSEGDLVAEKLGPIRSEQLEFTLADLPVAAWSAEKPNLYQVRLYLYQAGSELEVSRQEVGFRNFEL

KDGIMYLNGQRIVFKGANRHEFDSKLGRAITEEDMIWDIKTMKRSNINAVRCSHYPNQSLFYRLCDKYGLYVIDEANLESHGT

WEKVGGHEDPSFNVPGDDQHWLGASLSRVKNMMARDKNHASILEWSLGNESYAGTVFAQMADYVRKADPTRVQHYEGVEHNRK

FDDACQIESRMYAPAKVIEEYLINKPAKPFISVEYAHAMGNSVGDLAAYTALEKYPHYQGGFIWDWIDQGLEKDGHLLYGGDF

DDRPEDYEFCGNGLVFADRTESPKLANVKALYANLKLEVKDGQLFLKNDNLFTNSSSYYFLTSLLVDGKLTYQSRPLTFGLEP

GESGEFALPWPEVADEKGEVVYRVTAHLKEDLPWADEGFEVAEAEEVAQKLPEFKPEGRPDLVDSDYNLGLKGNNFQILFSKV

KGWPVSLKYAGREYLKRLPEFTFWRALTDNDRGAGYGYDLARWENAGKYARLKDISCEVKEDSVLVKTAFTLPVALKGDLTVI

YEVDGRGKIAVTADFPGAEEAGLLPAFGENLALPKELTDYRYYGLGPNESYPDRLEGNYLGIYQGAVKKNFSPYLRPQETGNR

SKVRWYQLFDEKGGLEFTANGADLNLSALPYSAAQIEAADHAFDLINNYTWVRALSAQMGVGGDDSWGQKVHPEFCLDAQKAR

QLRLVIQPLLLK

SEQ ID No. 13
MSNKLVKEKRVDQADLANLTDPEVYEVNTIPPHSDHESFQSQEELEEGKSSLVQSLDGNWLIDYAENGQGPINFYAEDFDDSN

FKSVKVPGNLELQGFGQPQYVNIQYPWDGSEEIFPPQVPSKNPLASYVRYFDLDEALWDKEVSLKFAGAATAIYVWLNGHFVG

YGEDSFTPSEFMVTKFLKKEGNRLAVALYKYSSASWLEDQDFWRLSGLTRSVTLEAKPLLHLEDLKLTASLTDNYQKGKLEVE

ANIAYRLPNASFKLEVRDSEGDLVAEKVGPIRSEKLGFSLADLPVAAWSAEKPNLYQVRLYLYQAGSELEVSRQEVGFRNFEL

KDGIMYLNGQRIVFKGVNRHEFDSKLGRAITEADMIWDIKTMKQSNINAVRCSHYPNQSLFYRLCDKYGLYVIDEANLESHGT

WEKVGHEDPSFNVPGDDQHWLGASLSRVKNMMARDKNHASILIWSLGNESYAGTVFAQMADYVRKADPIRVQHYEGVTHNRKE

-continued

DDATQIESRMYAPAKEIEEYLIKKPAKPFISVEYAHAMGNSVGDLAAYTALEKYPHYQGGFIWDWIDQGLEKDGHLLYGGDFD

DRPTDYEFCGDGLVFADRITSPKLANVKALYSNLKLEVKDGQLFIKNDNLFTNSSAYYFLASLLVDGKLIYQSQPLTFGLEPG

ESGTFVLPWPEVEDEKGEIVYQVTAHLKEDLPWADEGFTVAEAEEAVTXLPEFYPAGRPELVDSDFNEGLKGNGFRILFSKAK

GWPVSIKYAGREYLKRLPEFTFWRALTDNDRGAGYGYDLAKWENAGKYARLQDISYEIKENSALVKTTFTLPVALKGDLTITY

EVDSLGKIAVTANFPGAVENGLLPAFGLNFALPKELSDYRYYGLGPNESYADRLEGSYLGIYQGAVEKNFIPYLRPQEAGNRS

KVRYYQLFDEEGGLEFTANGADLNLSALPYSAAQIEAADHAFELTNNYTWVRALAAQMGVGGDDSWGQKVHPEFCEDAQEARQ

LKLVEQPLLLK

SEQ ID No. 14
MSNKLVKEKRVDQAELAWLTDPEVYEVNTIPPHFDHESFQSQEELEEGKSSLVQSLDGDWLIDYAENGQGPVNFYAEDFDDSN

FKSVKVPGNLELQGFGQPQYVNVQYPWDGSEEIFPPQIPSKNPLASYVRYFDLDEAFWDKEVSLKFDGAAIAIYVWLNGHFVG

YGEDSFTPSEFMVTKFLKKENNRLAVALYKYSSASWLEDQDFWRMSGLFRSVTLQAKPRLHLEDLKLTASLTDNYQKGKLEVE

ANIAYRLPNASFKLEVRDSEGDLVAEKLGPIRSEQLEFILADLPVAAWSAEKPNLYQVRLYLYQAGSLLEVSRQEVGFRNFEL

KDGIMYLNGQRIVFKGANRHEFDSKLGRAITEEDMIWDIKTMKRSNINAVRCSHYPNQSLFYRLCDKYGLYVIDEANLESHGT

WEKVGGHEDPSFNVPGDDQHWLGASLSRVKNMMARDKNHASILEWSLGNESYAGTVFAQMADYVRKADPTRVQHYEGVEHNRK

FDDATQIESRMYAPAKVIEEYLINKPAKPFISVEYAHAMGNSVGDLAAYTALEKYPHYQGGFIWDWIDQGLEKDGHLLYGGDF

DDRPTDYEFCGNGLVFADRIESPKLANVKALYANLKLEVKDGQLFLKNDNLFTNSSYYFLISLLVDGKLIYQSRPLIFGLEP

GESGTFALPWPEVADEKGFVVYRVTAHLKEDLPWADEGFTVAEAEEVAQKLPEFKPEGRPDLVDSDYNLGLKGNNFQILFSKV

KGWPVSLKYAGREYLKRLPEFIFWRALIDNDRGAGYGYDLARWENAGKYARLKDISCEVKEDSVLVKTAFILPVALKGDLTVT

YEVDGRGKIAVTADFPGAEEEAGLLPAFGENLALPKELTDYRYYGLGPNESYPDRLEGNYLGIYQGAVKKNFSPYLRPQETGNR

SKVRWYQLFDEKGGLEFIANGADLNLSALPYSAAQIEAADHAFELINNYTWVRALSAQMGVGGDDSWGQKVHPEFCLDAQKAR

QLRLVIQPLLLK

SEQ ID No. 15
MSNKLVKEKRVDQAELAWLTDPEVYEVNTIPPHSDHESFQSQEELEEGKSSLVQSLDGDWLIDYAENGQGPVNFYAEDFDDSN

FKSVKVPGNLELQGFGQPQYVNVQYPWDGSEEIFPPQIPSKNPLASYVRYFDLDEAFWDKEVSLKFDGAAIAIYVWLNGHFVG

YGEDSFTPSEFMVIKFLKKENNRLAVALYKYSSASWLEDQDFWRMSGLFRSVILQAKPRLHLEDLKLIASLIDNYQKGKLEVE

ANIAYRLPNASFKLEVRDSEGDLVAEKLGPIRSEQLEFILADLPVAAWSAEKPNLYQVRLYLYQAGSLLEVSRQEVGFRNFEL

KDGIMYLNGQRIVFKGANRHEFDSKLGRAIIEEDMIWDIKTMKRSNINAVRCSHYPNQSLFYRLCDKYGLYVIDEANLESHGT

WEKVGGHEDPSFNVPGDDQHWLGASLSRVKNMMARDKNHASILIWSLGNESYAGIVFAQMADYVRKADPIRVQHYEGVTHNRK

FDDATQIESRMYAPAKVIEEYLINKPAKPFISVEYAHAMGNSVGDLAAYTALEKYPHYQGGFIWDWIDQGLEKDGHLLYGGDF

DDRPTDYEFCGNGLVFADRIESPKLANVKALYANLKLEVKDGQLFLKNDNLFTNSSYYFLISLLVDGKLIYQSRPLIFGLEP

GESGTFALPWPEVADEKGEVVYRVTAHLKEDLPWADEGFTVAEAEEVAQKLPEFKPEGRPDLVDSDYNLGLKGNNFQILFSKV

KGWPVSLKYAGREYLKRLPEFIFWRALIDNDRGAGYGYDLARWENAGKYARLKDISCEVKEDSVLVKTAFILPVALKGDLTVT

YEVDGRGKIAVTADFPGAEEEAGLLPAFGENLALPKELTDYRYYGLGPNESYPDRLEGNYLGIYQGAVKKNFSPYLRPQETGNR

SKVRWYQLFDEKGGLEFTANGADLNLSALPYSAAQIEAADHAFELINNYTWVRALSAQMGVGGDDSWGQKVHPEFCLDAQKAR

QLRLVIQPLLLK

SEQ ID No. 16
MSNKLVKEKRVDQADLAWLIDPEVYEVNTIPPHSDHESFQSQEELEEGKSSLVQSLDGDWLIDYAENGQGPVNFYAEDFDDSN

FKSVKVPGNLELQGFGQPQYVNIQYPWDGSEEIFPPQVPSKNPLASYVRYFDLDEAFWDKEVSLKFAGAATAIYVWLNGHFVG

YGEDSFTPSEFMVTKFLKKENNRLAVALYKYSSASWLEDQDFWRLSGLFRSVTLQAKPLLHLEDLKLTASLTDNYQKGKLEVE

ANIAYRLPNASFKLEVRDSEGDLVAEKLGPIRSEQLEFILADLPVAAWSAEKPNLYQVRLYLYQAGSLLEVSRQEVGFRNFEL

KDGIMYLNGQRIVFKGVNRHEFDSKLGRAITEEDMIWDIKTMKRSNINAVRCSHYPNQSLFYRLCDKYGLYVIDEANLESHGT

WEKVGHEDPSFNVPCDDQHWLGASLSRVKNMMARDKNHASILIWSLGNESYAGIVFAQMADYVRKADPIRVQHYEGVTHNRKE

-continued

DDATQIESRMYAPAKEIEEYLIKKPAKPFISVEYAHAMGNSVGDLAAYTALEKYPHYQGGFIWDWIDQGLEKDGHELYGGGDF

DDRPCDYEFCGNGLVFADRTTSPKLANVKALYSNLKLEVKDGQLFLKNDNLFTNSSAYYFLTSLLVDGKLTYQSQPLTFGLEP

GESGEFVLPWPEVEDEKGEIVYQVTAHLKEDLPWADEGFEVAEAEEAVTKLPEFYPAGRPELVDSDFNLGLKGNGFRILFSKA

KGWPVSIKYAGREYLKRLPEFTFWRALTDNDRGAGYGYDLAKWENAGKYARLQDISYEIKENSVLVKIAFTLPVALKGDLTII

YEVDSLGKIAVTANFPGAVENGLLPAFGLNFALPKELSDYRYYGLGPNESYADRLEGSYLGIYQGAVEKNFTPYLRPQEAGNR

SKVRYYQLFDEESGLEFTANGADLNLSALPYSAAQIEAADHAFELSNNYTWVRALAAQMGVGGDDSWGQKVHPEFCLDAQEAR

QLKLVIQPLLLK

SEQ ID No. 17
MSNKLVKEKRVDQADLAWLTDPEVYEVNTIPPHSDHESFQSQEELEEGKSSLVQSLDGDWLIDYAENGQGPVNFYAEDFDDSN

FKSVKVPGNLELQGFGQPQYVNVQYPWDGSEEIFPPQIPSKNPLASYVRYFDLDEAFWDKEVSLKFDGAATAIYVWLNGHFVG

YGEDSFTPSEFMVIKFLKKENNRLAVALYKYSSASWLEDQDFWRMSGLFRSVTLQAKPRLHLEDLKLTASLTDNYQKGKLEVE

ANIAYRLPNASFKLEVRDSEGDLVAEKLGPIRSEQLEFTLADLPVAAWSAEKPNLYQVRLYLYQAGSELEVSRQEVGFRNFEL

KDGIMYLNGQRIVFKGVNRHEFDSKLGRAITEEDMIWDIKTIKRSNINAVRCSHYPNQSLFYRLCDKYGLYVIDEANLESHGT

WEKVGGHEDPSFNVPGDDQHWLGASLSRVKNMMARDKNHASILEWSLGNESYAGTVFAQMADYVRKADPTRVQHYEGVCHNRK

FDDACQIESRMYAPAKVIEEYLINKPAKPFISVEYAHAMGNSVGDLAAYTALEKYPHYQGGFIWDWIDQGLEKDGHLLYGGDF

DDRPEDYEFCGNGLVFADRTESPKLANVKALYANLKLEVKDGQLFLKNDNLFTNSSYYFLTSLLVDGKLTYQSRPLTFGLEP

GESGEFALPWPEVADEKGEVVYRVTAHLKEDLPWADEGFEVAEAEEVAQKLPEFKPEGRPDLVDSDYNLGLKGNNFQILFSKV

KGWPVSLKYAGREYLKRLPEFTFWRALTDNDRGAGYGYDLARWENAGKYARLKDISCEVKEDSVLVKTAFTLPVAEKGDLTVT

YEVDGRGKIAVTADFPGAEEEAGLLPAFGENLALPKELIDYRYYGLGPNESYPDRLEGNYLGIYQGAVKKNFSPYLRPQETGNR

SKVRWYQLFDEKGGLEFTANGADLNLSALPYSAAQIEAADHAFDLINNYTWVRALSAQMGVGGDDSWGQKVHPEFCLDAQKAR

QLRLVIQPLLLK

SEQ ID No. 18
MSNKLVKEKRVDQADLANLTDPEVYEVNTIPPHSDHESFQSQEELEEGASSLVQSLDGDWLIDYAENGQGPVNFYAEDFDDSN

FKSVKVPGNLELQGFGQPQYVNVQYPWDGSEEIFPPQIPSKNPLASYVRYFDLDEAFWDKEVSLKFDGAATAIYVWLNGHFVG

YGEDSFTPSEFMVTKFLKKENNRLAVALYKYSSASWLEDQDFWRMSGLFRSVTLQAKPRLHLEDLKLTASLTDNYQKGKLEVE

ANIAYRLPNASFKLEVRDSEGDLVAEKLGPIGSEQLEFTLADLPVAAWSAEKPNLYQVRLYLYQAGSELEVSRQEVGFRNFEL

KDGIMYLNGQRIVFKGVNRHEFDSKLGRAITEEDMIWDIKTIKRSNINAVRCSHYPNQSLFYRLCDKYGLYVIDEANLESHGT

WEKVGGHEDPSFNVPGDDQHWLGASLSRVKNMMARDKNHASILEWSLGNESYAGTVFAQMADYVRKADPTRVQHYEGVEHNRK

FDDACQIESRMYAPAKVIEEYLINKPAKPFISVEYAHAMGNSVGDLAAYTALEKYPHYQGGFIWDWIDQGLEKDGHLLYGGDF

DDRPCDYEFCGNGLVFADRTESPKLANVKALYANLKLEVKDGQLFLKNDNLFTNSSYYFLTSLLVDGKLTYQSRPLTFGLEP

GESGEFALPWPEVADEKGEVVYRVTAHLKEDLPWADEGFEVAEAEEVAQKLPEFKPEGRPDLVDSDYNLGLKGNNFQILFSKV

KGWPVSLKYAGREYLKRLPEFTFWRALTDNDRGAGYGYDLARWENAGKYARLKDISCEVKEDSVLVKTAFTLPVALKGDLTVI

YEVDGRGKIAVTADFPGAEEEAGLLPAFGENLALPKELTDYRYYGLGPNESYPDRLEGNYLGIYQGAVKKNFSPYLRPQETGNR

SKVRWYQLFDEKGGLEFTANGADLNLSALPYSAAQIEAADHAFELINNYTWVRALSAQMGVGGDDSWGQKVHPEFCLDAQKAR

QLRLVIQPLLLK

SEQ ID No. 19
MSNKLVKEKRVDQADLAWLTDPEVYEVNTIPPHSDHESFQSQEELEEGKSSLVQSLDGNWLIDYAENGQGPINFYAEDFDDSN

FKSVKVPGNLELQGFGQPQYVNIQYPWDGSEEIFPPQVPSKNPLASYVRYFDLDEALWDKEVSLKFAGAATAIYVWLNGHFVG

YGEDSFTPSEFMVIKFLKKEGNRLAVALYKYSSASWLEDQDFWRLSGLFRSVILEAKPLLHLEDLKLTASLTDNYQKGKLEVE

ANIAYRLPNASFKLEVRDSEGDLVAEKVGPIRSEKLDFSLADLPVAAWSAEKPNLYQVRLYLYQAGSLLEVSRQEVGFRNFEL

KDGIMYLNGQRIVFKGVNRHEFDSKLGRAIIEADMIWDIKTMKQSNINAVRCSHYPNQSLFYRLCDKYGLYVIDEANLESHGT

WEKVGHEDPSFNVPGDDQHWLGASLSRVKNMMARDKNHASILIWSLGNESYAGIVFAQMADYVRKADPIRVQHYEGVTHNRKF

-continued

DDAIQIESRMYAPAKEIEEYLIKKPAKPFISVEYAHAMGNSVGDLAAYTALEKYPHYQGGFIWDWIDQGLEKDGHLLYGGDFD

DRPTDYEFCGDGLVFADRTTSPKLANVKALYSNLKLEVKDGQLFIKNDNLFTNSSAYYFLTSLLVDGKLTYQSQPLTFGLEPG

ESGIFALPWPEVEDEKGEIVYQVIAHLKEDLPWADEGFIVAEAEEAVTKLPEFYPAGRPELVDSDFNLGLKGNGFRILFSKAK

GWPVSIKYAGREYLKRLPEFTFWRALIDNDRGAGYGYDLAKWENAGKYARLQDISYEIKENSALVKIAFILPVALKGDLTIIY

EVDSLGKIAVTANFPGAVENGLLPAFGLNFALPKELSDYRYYGLGPNESYADRLEGSYLGIYQGMVEKNFIPYLRPQEAGNRS

KVRYYQLFDEEGGLEFTANGADLNLSALPYSAAQIEAADHAFELTNNYTWVRALAAQMGVGGDDSWGQKVHPEFCLDAQEARQ

LKLVEQPLLLK (G145 Domain a)

SEQ ID No. 20
MQANTNWLDNPEVFRVNQLPAHSDHPFFRDYREWQKQHSSYQQSLNGKWKFHFSANPMDRPQDFYQRDFDSSNFDSIPVPSEi

ELSNYTQNQYINVLFPWEGKIFRRPAYALDPNDHEEGSFSKGADNIVGSYLKRFDLSSALIGKDVHIKFEGVEQAMYVWLNGH

FVGYAEDSFTPSEFDLTPYIQDKDNLLAVEVFKHSTASWLEDQDMFRFSGIFRSVELLGIPATHLMDMDLKPRVADNYQDGIF

NLKLHFIGKKAGSFHLLVKDIKGHTLLEKNEDIKENVQINNEKFENVHLWNNHDPYLYQLLIEVYDEQQNLLELIPFQFGFRR

IEISPEKVVLLNGKRLIINGVNRHEWDAKRGRSITMSDMTTDINTFKENNINAVRTCHYPNQIPWYYLCDQNGIYVMAENNLE

SHGTWQKMGEIEPSDNVPGSIPQWKEAVIDRARNNYETFKNHTSILFWSIGNESYAGDNIIAMNEFYKSHDDTRLVHYEGVVH

RPELKDKISDVESCMYLPPKKVEEYLQNDPPKPFMEGEYMHDMGNSDGGMGSYIKLLDKYPQYFGGFIWDFIDQALLVHDEIS

GHDVLRYGGDFDDRHSDYEFSGDGLMFADRIPKPAMQEVRYYYGLHK (G145 Domain b)

SEQ ID No. 21
MDYTNNQLHIIYGDATFGVNGKDFQYIFSYERGGLESLKVHGKEWLYRVPTPTFWRAITDNDRGSGFNLKAAQWLGADMFTKC

TDIHLKVDRHDFAELPIAPFNNKFSNHEYAKSAEISFTYQTLTEPATNAKIIYNIDDVGHIKVTMRYYGKKGLPPLPVEGIRL

TMPTAATGFDYEGLSGETYPDRMAGAKEGKEHIDGLPVTEYLVPQENGMHMQTKKLTINRETTQNNVDRINEKFSESIQQAEK

PFNFSCLPYTAEELENATHIEELPLVRRTVLVIAGAVRGVGGIDSWGTDVESAYHINPELDEEFSFIEN

SEQ ID No. 22
MTDVSHVDRASQAWLTDPTVFEVNRTPAHSSHKWYARDPQSGQWSDLKQSLDGEWRVEVVQAADINLEEEPATAESFDDSSFE

RIQVPGHLQTAGLMNHKYVNVQYPWDGHENPLEPNIPENNHVALYRRKFTVSAPVANAKQAGGSVSIVFEGMATAIYVWVNGA

FVGYGEDGFTPNEFDITELLHDGENVVAVACYEYSSASWLEDQDFWRLHGLFRSVELAARPEVHIENTQIEADWDPEAGTASL

DAALEVLNAADAATVRATLKDADGNTVWQTTGDAEAQTAESSGPLQGIAPWSAESPTLYELDVDVIDQAGDVIECTSQKVGFR

RFRIEDGILTINGKRIVFKGADRHEFDAEQGRAITEQDMEDDVVFCKRHNINSIRTSEYPNQERWYEECDEYGIYEIDEANLE

AHGSWSLPGDVLTEDTIVPGSKREWEGACVDRVNSMMRRDYNHPSVLIWSLGNESYVGDVFRAMYKHVHDIDPNRPVHYEGVT

HNRDYDDVTDIETRMYSHADEIEKYLKDDPKKPYLSCEYMHAMGNSVGNMDEYTALERYPKYQGGFIWDFIDQAIYATQPDGT

RSLRYGGDFGDRPSDYEFSGDGLLFANRKPSPKAQEVKQLYSNVHIDVTKDSVSVKNDNLFTATGDYVFVLSVLADGKPVWQS

TRRFDVPAGETRTFLVANPVAAYRADARELVLQVSQRLAKATDWAESGYELAFGQTVVPADATATPDTKPADGTITVGRWNAG

VRGAGREVLLSRTQGGMVSYTFAGNEFVERRPAITTFRPLTDNDRGAGHGFERVQWLGAGRYARCVDNVLEQIDDSTLKGTYT

YELAEAQRTXVTVSYTAHIDGRVNLHVEYPGEQGDLPTIPAFGEEWTLPVQYTNLRFFGTGPAETYLDRKHAKLGVWSENAFA

DHAPYLMPQETGNHEDVRWAEITDDHGHGMRVSRADGAAPFAVSLLPYSSFMLEEAQEQDELPKPKHMFLRVLAAQKGVGGDD

SWMSPVHPQYHIPADKPISLDVDLELI (G224 Domain a)

SEQ ID No. 23
MDADEKWLDEPETFRVNQLPAHSDHYYYGNYDEWRHNNSRFAQNLDGQWQFNFAENLRERENDFYKMDYDSSSFGTIEVPSEI

ELNNYAQNNYINTLIPWEGKIYRRPAYIESPDDAQEGSFSDGDDNTIGEYLKHFDLPSLRGKQVRIRFDGVERAMYVWLNGH

FIGYAEDSFTPSEFDLTPYIQDEGNVLAVEVFKHSTASWEEDQDMFRFSGIFRSVNLLAQPLVHVEDENIRPIVTDNYQDGIF

NVELQLHGEXTGNVNVRVIDNDGNTLVNETEPVDSTVKVQDQFLENVHLWDNHDPYLYQLLIEIRDDEGNLVELVPYRFGFRR

TEINKDHVVLLNGQRLIINGVNRHEWDARRGRAITMDDMESDIHTFKENNINAVRTCEYPDQIPWYYECDDNGIYMMAENNLE

SHATWQKMGAIEPSYNVPGSVPQWRDVVVDRARTNYETFKNHPSILFWSLGNESYAGDNIVKMNEFYKKEDDSRLVHYEGVCH
TPEYRDRISDVESWMYLPPKEVEEYLKNNPDKPFMECEYMHDMGNSDGGMGSYISLLDKYPQYFGGFIWDFIDQALLVKDPVS
GQEVMRYGGDFDDRHSDYEFSGDGLMFADRTPKPAMQEVRYYYGLHK (G224 Domain b)

SEQ ID No. 24

MAYTNKLRVIYGDAILGLSGDGFHYIFSYERGGLESLKLNGKEWLYREPMPTFWRATTDNDRGSGFNIRSAQWLAADTFHKCV
GIDLEVDNQHFAELPIAPITNEFSDPVSAESVKIKYTFAELTVPAIQVTVIYEVNGQGEIKVTMHYYGHEDLPGLPVVGMRFI
MPTVATGFDYQGLSGETYPDRMAGATEGTFEVDGLPVTKYLVPQENGMHMATHALTITRDSTQNNADHSREPFSLTVKQDAQP
FAFSCLPYTAEELENATHIEELPLARRTVLVVAGAVRGVGGIDSWGADVEEQYHIPADRDVEFSFVLNAK

SEQ ID No. 25

MSNKLVKEKRVDQADLANLTDPEVYEVNTIPPHSDHESFQSQEELEEGASSLVQSLDGNWLIDYAENGQGPINFYAEDFDDSN
FKSVKVPGNLELQGFGQPQYVNIQYPWDGSEEIFPPQVPSKIPLASYVRYFDLDEALWDKEVSLKFAGAATAIYVWLNGHFVG
YGEDSFTPSEFMVTKFLKKEGNRLAVALYKYSSASWLEDQDFWRLSGLFRSVTLEAKPLLHLEDLKLTASLTDNYQKGKLEVE
ANIAYRLPNASFKLEVRDSEGDLVAEKVGPIRSEKLDFSLADLPVAAWSAEKPNLYQVRLYLYQAGSELEVSRQEVGFRNFEL
KDGIMYLNGQRIVFKGVNRHEFDSKLGRAITEADMIWDIKTMKQSNINAVRCSHYPNQSLFYRLCDKYGLYVIDEANLESHGT
WEKVGHEDPSFNVPGDDQHWLGASLSRVKNMMARDKNHASILIWSLGNESYAGTVFAQMADYVRKADPIRVQHYEGVTHNRKF
DDATQIESRMYAPAKEIEEYLIKKPAKPFISVEYAHAMGNSVGDLAAYTALEKYPHYQGGFIWDWIDQGLEKDGHLLYGGDFD
DRPTDYEFCGDGLVFADRITSPKLANVKALYSNLKLEVKDGQLFIKNDNLFTNSSAYYFLTSLLVDGKLTYQSQPLTFGLEPG
ESGTFALPWPEVEDEKGEIVYQVTAHLKEDLPWADEGFTVAEAEEAVTXLPEFYPAGRPELVDSDFNEGLKGNGFRILFSKAK
GWPVSIKYAGREYLKRLPEFTFWRALTDNDRGAGYGYDLAKWENAGKYARLQDISYEIKENSALVKTTFTLPVALKGDLIITY
EVDSLGKIAVTANFPGAVENGLLPAFGLNFALPKELSDYRYYGLGPNESYADRLEGSYLGIYQGMVEKNFTPYLRPQEAGNRS
KVRYYQLFDEEGGLEFTANGADLNLSALPYSAAQIEAADHAFELTNNYTWVRALAAQMGVGGDDSWGQKVHPEFCEDAQEARQ
LKLVEQPLLLK (G2S2 Domain a)

SEQ ID No. 26

MQANENWLDNPEVFRVNQLPAHSDHPFFRDYREWQKQHSSYQQSLNGKWKFHFSANPMDRPQDFYQRDFDSSNFDSIPVPSEI
ELSNYTQNQYINVLFPWEGKIFRRPAYAEDPNDHEEGSFSKGADNTVGSYLKRFDLSSALIGKDVHIKFEGVEQAMYVWLNGH
FVGYAEDSFTPSEFDLTPYIQEKDNLLAVEVFKHSTASWLEDQDMFRFSGIFRSVELLGIPATHLMDMDLKPRVADNYQDGIF
NLKLHFIGKKAGSFHLLVKDIKGHTLLEKNEDIKENVQINNEKFENVHLWNNHDPYLYQLLIEVYDEQQNLLELIPFQFGFRR
TEISPEKVVLLNGKRLIINGVNRHEWDAKRGRSITMSDMETDINTFKENNINAVRTCEYPNQIPWYYECDQNGIYVMAENNLE
SHGTWQKMGEIEPSDNVPGSIPQWKEAVIDRARNNYETFKNHTSILFWSLGNESYAGDNIIAMNEFYKSEDDTRLVHYEGVVH
RPELKDKISDVESCMYLPPKKVEEYLQNDPPKPFMECEYMHDMGNSNGGMDSYIKLLDKYPQYFGGFIWDFIDQALLVHDEIS
GHDVLRYGGDFDDRHSDYEFSGDGLMFADRKPKPAMQEVRYYYGLHK (G2S2 Domain b)

SEQ ID No. 27

MDYTNNQLHIIYGDATFGVNGKDFQYIFSYERGGLESLKVHGKEWLYRVPTPTFWRATTDNDRGSGFNLKAAQWLGADMFTKC
TDIHLKVDRHDFAELPIAPFNNKFSNHEYAKSAEISFTYQTLTEPATNAKIIYNIDDGGHIKVTMRYYGKKGLPPEPVEGIRL
TMPTAATGFDYEGLSGETYPDRMAGAKEGKFHIDGLPVTEYLVPQENGMHMQTKKLIINRETTQNNVDRTNEKFSESIQQAEK
PFNFSCLPYTAEELENATHIEELPLVRRTVLVIAGAVRGVGGIDSWGTDVESAYHINPDLDEEFSFIEN (G334 Domain a)

SEQ ID No. 28

MKANEKWLDDPEVFRINQLPAHSDHPFYKDYREWQKHSSSFKQSLNGAWQFHFSKDPQSRPIDFYKLSFDSSSFDTIPVPSEI
ELNGYAQNQYTNILYPWESKIYRKPAYTLGRGIKDGDFSQGKDNTVGSYLKHFDLNPALAGEDIHIQFEGVERAMYVYLNGHF
EGYAEDSETPSEFDLTPYIQAKDNILAVEVEKHSTASWLEDQDMFRESGIFRSVELLALPRIHLMDLDIKPTVVNDYHDGVEN
AKLHFMGKTSGNVHVLIEDIDGKTLLNKKLPLKSTVEIENETFANVHLWDNHDPYLYQLIIEVHDQDGKLVELIPYQFGFRKI

-continued

EITKDHVVLLNGKRLIINGVNREEWDAKRGRSITLADMKQDIACFKHNNINAVRTCHYPNQIPWYYLCDQNGIYMMAENNLES
HGTWQKLGQVEATSNVPGSIPEWREVVVDRARSNYETFKNHTAELFWSLGNESYAGSNIAAMNKLYKDHDSSRLTHYEGVFHA
PEFKKEISDLESCMYLPPKEAEEYLQNPKKPLVECEYMHDMGNSDGGIGSYIKLIDKYPQYMGGFIWDFIDQALLVHDPVSGQ
DVLRYGGDFDDRHSDYEFSGDGLMFADRTPKPAMQEVRYYYGLHK (G334 Domain b)

SEQ ID No. 29
MAYTNNLHVVYGEASLGVNGQDFAYLFSYERGVLESLKIKDKEWLYRTPTPTFWRATTDNDRGSGFNQKAAQWLGADMFTKCV
GIHVQVDDHQFDELPIAPINNQFSNQEFAHEVKVAFDYEELTTPAIKVXIIYNINDAGHMTITMHYFGKKGLPPLPVIGMRFI
MPTKAKSFDYTGLSGETYPDRMAGAERGTFEEDGLPVTKYLVPQENGMHMQTNELVITRNSTQNNADKDGDFSLKITQEKQPF
NFSLLPYTAZELENATHIEELPLARRSVEVIAGAVRGVGGIDSWGSDVEEQYHIDPEQDHEFSFILN

SEQ ID No 30
MNMTKIQTYLNDPKIVSVNTVDAHSDHKYFESLEEFSEGEMKLRQSLNGKWKIHYAQNTNQVLKDFYKTEFDETDLNFINVPG
MNMTKIQTYLNDPKIVSVNTVDAHSDHKYFESEEEFSEGEMKLRQSLNGKWKIHYAQNTNQVLKDFYKIEFDETDENFENVPG
HLELQGFGSPQYVNIQYPWDGKEFLRPPQVPQESNAVASYVKHFTLNDALKDKKVFISFQGVATSIFVWVNGNFVGYSEDSFT
PSEFEISDYLVEGDNKLAVAVYRYSIASWLEDQDFWRLYGIFRDVYLYAIPKVHVQDLFVKGDYDYQTKAGQLDIDLKEVGDY
EDKKIKYVLSDYEGIVTEGDASVNGDGELSVSLENLKIKPWSAESPKLYDLILHVLDDDQVVEVVPVKVGFRRFEIKDKLMLL
NGKREVFKGVNRHEFNARIGRCITEEDMEWDEKVMKQHNENAVRTSHYPNQTRWYELCDEYGLYVIDEANLETHGTWQKLGLC
EPSWNIPASEPEWLPACLDRANNMFQRDKNEASVIIWSCGNESYAGKDIADMADYFRSVDNIRPVHYEGVAWCREFDYITDIE
SRMYAKPADIEEYLITGKLVDLSSVSDKHFASGNLTNKPQKPYTSCEYMHTMGNSGGGLQLYTDLEKYPEYQGGFIWDFIDQA
TYKTLPNGSEFLSYGGDWHDRPSDYEFCGNGIVFADRTLTPKLQTVKHLYSNIKIAVDEKSVIIKNDNLFEDLSAYTFLARVY
EDGRKVSESEYHFDVKPGEEATFPVNFVVEASNSEQIYEVACVLREATKWAPKGHEIVRGQYVVEKISTETPVKAPINVVEGD
FNIGIQGQNFSILLSRAQNTLVSAKYNGVEFIEKGPKLSFTRAYTDNDRGAGYPFEMAGWKVAGNYSKVTDTQIQIEDDSVKV
TYVHELPGLSDVEVKVTYQVDYKGRIFVTANYDGKAGLPNFPEFGLEFAIGSQFINLSYYGYGAEESYRDKLPGAYLGRYEIS
VEKIFAPYLMPQESGNHYGIREFIVSDDNHNGEKFIALNKAFEFSALRNSIEQIENARHQYELQESDAIWIKVLAAQMGVGGD
DSWGAPVHDEFLLSSADSYQLSFMIEPLN

SEQ ID No 31
MNNKLAQVKRVDQADLAWLIDPEIYEVNTIPPHSDHESFQSLEELEEGKSSLVQSLDGDWLIDYAENGEGPANFYEENFDDSS
FKSVKVPGNLELQGFGQPQYVNVQYPWDGSDEIFPPMIPSKNPVASYVRYFDLEEAFWDKEVSLKFAGAAIAIYVWLNGHFVG
YGEDSFTPSEFMVTKFLKKEGNRLAVALYKYSSASWLEDQDFWRMSGLFRSVTLEAKPLLHLQDLKLTASLTNDYQKGSLQVE
ADIDYRLPNSSFKLELRDSAGELVAEKVGPIRSEKLDFSLADLPVAAWSAEEPNLYQVRL3LYQQGSELEVSRQEVGFRNFEL
KDGIMYLNGKRIVFKGVNRHEFDSKLGRAITEADMIWDIKIMKQSNINAVRCSHYPNQSIFYHLCDKYGLYVIDEANLESHGT
WEKVGGHEDPSFNVPGDDQRWLGASLSRVKNMMARDKNHASILEWSLGNESYAGKVFAQMADYVRQADPTRVQHYEGVEHNRK
FDDATQIESRMYAPAKEIEEYLIKKPAKPFVSCEYAHAMGNSVGDLAAYTALEKYPHYQGGFIWDWIDQGLEKEGHLLYGGDF
DDRPSDYEFCGDGLVFADRITSPKLANVKALYSNLKLELKDGQLFLKNDNLFTNSSAYYFLTSLLVDGKLIYQSQPLIFALEP
GESGEFALPWPEVEDEKGEIVYQVTAHLKEDLPWADEGFEVAEAEEAVTKLPEFYPAGRPELVDSDYNLGIKGNGFRILFSKA
KGWPVSIKYAGREYLKRLPEFTFWRALTDNDRGAGYGYDLAKWENAGKYARLQDISYEIKENSVLVKTAFTLPVALKGDLTIT
YEVDSLGKIAVTANFPGAVENGLLPAFGLNFALPKELSDYRYYGLGPNESYADRLEGSYLGIYQGAVEKNFTPYLRPQEVGNR
SKVRYYQLFDEEGGLEFTANGANLNLSAEPYSAAQIEAADHAFELINNYTWVRALAAQMGVGGDDSWGQKVHPEFCLDAQEAR
QLKLVIQPLFTE

SEQ ID NO: 32
MADTAELAIVHATTASASWLTDPTVFAANRKPAHSSHRYVIGETSEPKQSLDGEWKVRIEQARNVDVESAPFAAVDFEDGDFG
AIEVPGHLQMAGYLKNKYVNIQYPWDGHEDPQAPNIPENNHVAIYRRRFALDAQLARTLENDGTVSLTFHGAATAIYVWLDGT
FVGYGEDGFTPSEFDVTEALRNGNGNAADSPEAEHTLTVACYEYSSASWLEDQDFWRLHGLFRTVELAAQPHTHVETVQLEAD

-continued

YTAADTAGTADTAELNAALTLRNPADAMTIESTLRDGDGNVVWESTQACNGEIALNSGKMTNIAPWSAESPTLYTLTVRVVGH

DGAIIETVTQKIGFRTFRIENGIMTLNGKRIVFKGADRHEFDAKRGRAITREDMLSDVVFCKRHNINAIRTSHYPNQEYWYDL

CDEYGLYLIDETNMETHGTWVANNVERPEDGIPGSRPEWEDACVDRINSMMRRDYNHPSVLIWSLGNESSAGEVFRAMYRHAH

TIDPNRPVHYEGSVHMREFEDVTDIESRMYAHADEIERYLNDGSPAHTDGPKKPYISCEYMHAMGNSCGNMDEYTALERYPMY

QGGFIWDFIDQAIETKLPDGTTRMCYGGDFGDRPSDYEFSGDGLLFADRTPSPKAQEVKQLYANVKIAVSVDEARITNDNLFV

STGDYRFVLRILADGKPVWSTTRRFDVAAGESASFEVDWPVDDYRSNAEELVLEVSQQLGNACDWAPAGYELAFGQCVVAGAK

TTADAVDAAGAPADGTVTLGRWNAGVRGQGREALFSRTQGGMVSYTFGEREFVLRRPSITTFRPLTDNDRGAGHAFERAAWAV

AGKYARCVDCAIANRGENAVEATYTYELAIPQRTKVTVRYVADTAGLVSLDVEYPGEKNGDLPTIPAFGIEWALPVEYANLRF

YGAGPEETYADRRHAKLGVWSTTAGDDCAPYLLPQETGNHEDVRWAEITDDSGHGVRVKRGAGAKPFAMSLLPYSSTMLEEAL

HQDELPKPRHMFLRLLAAQMGVGGDDSWMSPVHEQYQLPADQPLSLNVQLKLF

SEQ ID NO: 33
MANETRIEHASETWLADSTVFEVNRVPAHSDHKCYAHDSQTNEWSDLRQSLDGEWRVEVVQASDIEFNEEPFVRENFDDSAFE

RIQVPGHLQMAGLMNNKYVNIQYPWDGHENPAEPNIPENNHVALYRKTFTMANRLADTKNAGGTVSIVFHGMATAIYVWVNGM

FVGYGEDGFTPNEFDITEMLHDGENVVAVACYEYSSASWLEDODFWRLHGLFRSVELAAQPHVHIENMQIESDWDPESGSASL

DAALTVRNAADAATISATLKDSDGNVVWETANCADPDTSISTGSLNGIRPWSAEDPVLYEFEVTVIDHAGNIAEVAVQKVGFR

RFRIEDGIMTINGKRIVFKGADRHEFDPKRGRAITEQDMIDDVVFCKRHNLNAIRTSHYPNQERWYELCDEYGIYLIDETNLE

THGSWCLPGDVLTEETAVPGSKAHWEGACVDRVNSMVRRDYNHPSVLIWSLGNESYTGDVFRAMYKRVHDIDPNRPVHYEGVT

HNRDYNDVTDIETRMYAHADAIEEYLKNDPQKPYISCEYMHAMGNSCGNMDEYTALERYPKYQGGFIWDFIDQAIYATQPDGT

TSLRYGGDFGDRPSDYEFSGNGLVFADRKPTPKAQEVKQLYSNVHIDVAEDSVTIKNDNLFTSTGEYTFVLRVLADGEPVWQS

ERRFDVPAGSTEKLDVDWPLDLYRDGASELVLEVSQRLAKATNWAVAGYELAFGQTVVAGSKKASAPVKPVDGIVTVGRWNVG

VQGSGREVLLSRTQGGLVSYTFNNREFVLRRPAVTTFRALTDNDRGAGHGFERAQWLGAGRYARCIGNEIEQIDENTVKASYT

YELATPQRTKVTVSYTADTTGRVNLHVEYPGEPGDLPTIPAFGIEWTLPVQYSNLRFFGAGPEETYQDRKHAKLGVWSTDAFK

DHAPYLMPQETGNHEDVRWAEITDEKGHGLRISRAEGAEPFAMSLQPYSSFMLEEAQHQDELPAPKHMFLRVLAEQMGVGGDD

SWMSPVHPQYHIPADQPISLDVDLDLI (Reference enzyme)

SEQ ID NO: 34
MVEDATRSDSTTQMSSTPEVVYSSAVDSKQNRTSDFDANWKFMLSDSVQAQDPAFDDSAWQQVDLPHDYSITQKYSQSNEAES

AYLPGGTGWYRKSFTIDRDLAGKRIAINFDGVYMNATVWFNGVKLGTHPYGYSPFSFDLTGNAKFGGENTIVVKVENRLPSSR

WYSGSGIYRDVTLTVTDGVHVGNNGVAIKTPSLATQNGGNVTMNLTTKVANDTEAAANITLKQTVFPKGGKTDAAIGTVTTAS

KSIAAGASADVTSTITAASPKLWSIKNPNLYTVRTEVLNGDTVLDTYDTEYGFRWTGFDATSGFSLNGEKVKLKGVSMHHDQG

SLGAVANRRAIERQVEILQKMGVNSIRTTHNPAAKALIDVCNEKGVLVVEEVFDMWNRSKNGNTEDYGKWFGQTIAGDNAVLG

GDKDETWAKFDLTSTINRDRNAPSVIMWSLGNEMMEGISGSVSDFPATSAKLVAWTKAADSTRPMTYGDNKIKANWNESNTMG

DNLTANGGVVGTNYSDGANYDKIRTTHPSWAIYGSETASAINSRGIYNRTTGGAQSSDKQLTSYDNSAVGWGAVASSAWYDVV

QRDFVAGTYVWTGFDYLGEPTPWNGTGSGAVGSWPSPKNSYFGIVDTAGFPKDTYYFYQSQWNDDVHTLHILPAWNENVVAKG

SGNKVPVVVYTDAAKVKLYFTPKGSTEKRLIGEKSFTKKTTAAGYTYQVYEGTDKDSTAHKNMYLTWNVPWAEGTISAEAYDE

NNRLIPEGSTEGNASVTTTGKAAKLKADADRKTITADGKDLSYIEVDVTDANGHIVPDAANRVTFDVKGAGKLVGVDNGSSPD

HDSYQADNRKAFSGKVLAIVQSTKEAGEITVTAKADGLQSSTVKIATTAVPGTSTEKTVRSFYYSRNYYVKTGNKPILPSDVE

VRYSDGTSDRQNVTWDAVSDDQIAKAGSFSVAGTVAGQKISVRVTMIDEIGALLNYSASTPVGTPAVLPGSRPAVLPDGTVTS

ANFAVHWTKPADTVYNTAGTVKVPGTATVFGKEFKVTATIRVQRSQVTIGSSVSGNALRLTQNIPADKQSDTLDAIKDGSTTV

DANTGGGANPSAWTNWAYSKAGHNTAEITFEYATEQQLGQIVMYFFRDSNAVRFPDAGKTKIQISADGKNWTDLAATETIAAQ

ESSDRVKPYTYDFAPVGATFVKVTVTNADTTTPSGVVCAGLTEIELKTATSKFVTNTSAALSSLTVNGTKVSDSVLAAGSYNT

PAIIADVKAEGEGNASVTVLPAHDNVIRVITESEDHVTRKTFTINLGTEQEFPADSDERD (Reference enzyme)

SEQ ID No: 35

MSCLIPENLRNPKKVHENRLPTRAYYYDQDIFESLNGPWAFALFDAPLDAPDAKNLDWETAKKWSTISVPSHWELQEDWKYGK

PIYTNVQYPIPIDIPNPPTVNPTGVYARTFELDSKSIESFEHRLRFEGVDNCYELYVNGQYVGFNKGSRNGAEFDIQKYVSEG

ENLVVVKVFKWSDSTYIEDQDQWWLSGIYRDVSLLKLPKKAHIEDVRVTTTFVDSQYQDAELSVKVDVQGSSYDHINFTLYEP

EDGSKVYDASSLLNEENGNTTFSTKEFISFSTKKNEETAFKINVKAPEHWTAENPTLYKYQLDLIGSDGSVIQSIKHHVGFRQ

VELKDGNITVNGKDILFRGVNRHDHHPRFGRAVPLDFVVRDLILMKKFNINAVRNSHYPNHPKVYDLFDKLGFWVIDEADLET

HGVQEPFNRHTNLEAEYPDTKNKLYDVNAHYLSDNPEYEVAYLDRASQLVLRDVNHPSIIIWSLGNEACYGRNHKAMYKLIKQ

LDPTRLVHYEGDLNALSADIFSFMYPTFEIMERWRKNHTDENGKFEKPLILCEYGHAMGNGPGSLKEYQELFYKEKFYQGGFI

WEWANHGIEFEDVSTADGKLHKAYAYGGDFKEEVHDGVFIMDGLCNSEHNPTPGLVEYKKVIEPVHIKIAHGSVTITNKHDFI

TTDHLLFIDKDTGKTIDVPSLKPEESVTIPSDTTYVVAVLKDDAGVLKAGHEIAWGQAELPLKVPDFVTETAEKAAKINDGKR

YVSVESSGLHFILDKLLGKIESLKVKGKEISSKFEGSSITFWRPPTNNDEPRDFKNWKKYNIDLMKQNIHGVSVEKGSNGSLA

VVTVNSRISPVVFYYGFETVQKYTIFANKINLNTSMKLTGEYQPPDFPRVGYEFWLGDSYESFEWLGRGPGESYPDKKESQRF

GLYDSKDVEEFVYDYPQENGNHTDTHFLNIKFEGAGKLSIFQKEKPFNFKISDEYGVDEAAHACDVKRYGRHYLRLDHAIHGV

GSEACGPAVLDQYRLKAQDFNFEFDLAFE

EXAMPLES

General Material and Methods

Molecular Cloning and Genetic Techniques

Techniques for restriction enzyme digestions, ligation, transformation and other standard molecular biology manipulations were based on methods described in the literature (Maniatis et al. "Molecular cloning: a laboratory manual, 2nd edition" Cold Spring Harbor Laboratory Press, Cold Spring Harbor, NY, 1989; Sambrook and Russell "Molecular Cloning: A Laboratory Manual, 3rd edition" Cold Spring Harbor Laboratory Press, Cold Spring Harbor, NY 2001; Miller "Experiment in molecular genetics" Cold Spring Harbor Laboratory Press, 1972); or as suggested by the manufacturer. The PCR was carried out in a DNA thermal cycler obtained from (Bio-Rad, USA). DNA sequencing was performed by LGC, Berlin, Germany. Proteins were analyzed by polyacrylamide gel electrophoresis (PAGE) under the denaturation conditions using sodium dodecyl sulphate on gels containing 10% SDS (Mini-PROTEAN® TGX Stain-Free™ gel, Biorad, USA). Protein concentrations were determined using BCA method by following the protocol supplied with the kit.

Bacterial Strains, Plasmid and Growth Conditions

*Escherichia coli* strain TOP10 (Invitrogen) was used for the cloning and isolation of plasmids. The beta-galactosidase deficient *E. coli* strain BW25113 (Δ(araD-araB)567, ΔlacZ4787(::rrnB-3), λ-, rph-1, Δ(rhaD-rhaB)568, hsdR514) (Datsenko K A, Wanner B L; 2000, Proc Natl Acad Sci U.S.A. 97: 6640-6645) was used in combination with the pBAD/His vector (obtained from Invitrogen™ Life Technologies Corporation Europe BV) for recombinant protein production.

Growth Media for Protein Expression

2xPY medium containing (16 g/L BD BBL™ Phyton™ Peptone, 10 g/L Yeast Extract, 5 g/L NaCl) was used for the recombinant protein production. The growth medium was supplemented with ampicillin (100 µg/ml) to maintain the plasmid. Protein production was initiated by adding 0.05% of arabinose in to the culture medium.

Example 1: Construction of the Expression Vector for the Production of Lactases The genomic DNA of the lactic acid bacteria or bifidobacteria was extracted using commercial genomic extraction kit by following the supplied protocol (DNeasy, Qaigen, Germany). The lactase gene was amplified by PCR using two synthetic primers, using the purified genomic DNA source as biomass, and the PCR reagents were supplied in the Phusion U Hot start DNA polymerase (Thermo Scientific, USA) kit. The lactase gene was cloned into the start codon of the expression vector pBAD/His using the USER cloning method (Nour-Eldin HH, Geu-Flores F, Halkier BA, Plant Secondary Metabolism Engineering, Methods in Molecular Biology, 643; 2010), resulting in the expression construct. With the USER cloning method long, complementary overhangs in both PCR product and destination vector were generated. These overhangs can anneal to each other to form a stable hybridization product which was used to transform into *E. coli* without ligation. For the generation of overhangs in the PCR product, a single deoxyuradine residue is included in the upstream region of each primer to amplify target DNA. The lactase gene was amplified using the forward primer (5'-ATTAAC-CAUGCGACGCAACTTCGAATGGCC-3', SEQ ID NO:36) and reverse primer (ATCTTCTCUTTACCGCCT-TACCACGAGCACG, SEQ ID NO:37) containing a uridine at 9th position (as shown in bold), followed by with the lactase gene sequence. In parallel, the vector DNA was PCR amplified using the forward (5'-AGAGAAGAUT-TTCAGCCTGATACAGATTAAATC-3', SEQ ID NO:38) and reverse primer (5'-ATGGTTAAUTCCTCCTGT-TAGCCCAAAAAACGG-3', SEQ ID NO:39) pair containing single deoxyuracil residue at 9th positions (as highlighted in bold) followed by vector DNA sequence. The PCR products were purified using the commercial PCR purification kit (Qiagen, Denmark). The purified PCR products (lactase gene and the vector DNA) were mixed in equimolar amount and incubated with a commercial USER enzyme mix (New England Biolabs, USA) by following the supplied protocol. These enzymes remove the uracil residue and also the short fragment upstream of the uridine, thereby creating complementary overhang in the PCR products. These complementary overhangs anneal with each other resulting in the pBAD-lactase expression vector. Aliquots of the ligation mixture were transformed into chemically competent E. coli TOP 10 cells. Transformants were selected at 37° C. on LB-Amp plates (LB; Luria-Bertani, Amp; 100 µg/ml ampicillin). The following day, colony PCR was carried out using a small biomass from the overnight grown transformant using the vector primers (primer 1: 5'-CGGCGT-CACACTTTGCTATGCC-3', SEQ ID NO:40, and primer 2: 5'-CCGCGCTACTGCCGCCAGGC-3', SEQ ID NO:41). The positive clones from the colony PCR were cultured in 5 mL LB-Amp medium and plasmid DNA was isolated from the cells. The cloned lactase gene was sequenced to verify that no additional mutations had been introduced during the amplification of the gene. The plasmid DNA was transformed in to the expression host E. coli strain BW25113.

Example 2: Expression of Lactases in E. coli Expression Host

The lactase enzyme was produced in E. coli BW25113 using the pBAD expression system. Freshly transformed E. coli BW25113 cells carrying the plasmid DNA were collected from a Lb-Amp plate using a sterile loop and used to inoculate 5 mL of Lb-Amp medium. The overnight grown culture (200 µL) was used to inoculate 50 mL 2× PY medium (containing 100 µg/mL ampicillin) in a 250 mL flask in a shaker (Innova® 42). The culture was grown at 37° C. at 220 rpm until the OD600 reached between 0.6-0.8. The lactase expression was initiated by adding 0.05% arabinose into the culture medium and the cells were cultured for additional 16-20 hours at 18° C. at 180 rpm. Cells were harvested by centrifugation (5000 rpm, 10 min at 4° C.) and were stored at −20° C. until further use.

Example 3: Protein Purification Using Immobilized Metal Affinity Chromatography Cells from 50 mL culture was thawed on ice and the cells were lysed using 10 mL mixture of lysis buffer (BugBuster® (Novagen) containing 2 mg/mL Lysozyme (Sigma Aldrich), 1 unit Benzonase (Sigma Aldrich), and 1×Complete Protease inhibitor cocktail (EDTA-free, Roche)) by incubating the cells at room temperature for 30 min. After 30 min, the cell debris was removed by centrifugation at 16000 rpm for 20 min at 4° C. The obtained supernatant was filtered through 0.45 µm pore diameter filter. A gravity flow Ni-Sepharose (GE Healthcare) column was prepared with 1 mL slurry by washing out the ethanol and water. The column was then equilibrated with washing buffer (50 mM of $NaH_2PO_4$, pH 8.0 containing 300 mM of NaCl and 20 mM of Imidazole). The cell-free extract was applied to the column and the non-bound proteins were eluted from the column. The column was washed with 20 mL of washing buffer and the retained proteins were eluted with 3.5 mL of elution buffer (50 mM of $NaH_2PO_4$, pH 8.0 containing 300 mM of NaCl and 250 mM of imidazole). The collected fractions were analyzed by SDS-PAGE on gels containing 10% acrylamide and those contained the purified lactase enzymes combined together. The buffer was exchanged against the storage buffer (50 mM $KH_2PO_4$ buffer pH 7.0 containing 10 mM NaCl, 1 mM $MgCl_2$), using a prepacked PD-10 desalting G-25 gel filtration column (GE Healthcare). The purified enzymes were stored at 4° C. until further use.

Example 4: Protein Purification Using Gel Filtration Chromatography

Cells from 50 mL culture was thawed on ice and the cells were lysed using 10 mL mixture of lysis buffer (BugBuster® (Novagen) containing 2 mg/ml lysozyme, 1 unit Benzonase (Sigma Aldrich), and 1×Complete Protease inhibitor cocktail (EDTA-free, Roche)) by incubating the cells at room temperature (25° C.) for 30 min. After 30 min, the cell debris was removed by centrifugation at 16000 rpm for 20 min at 4° C. The obtained supernatant was filtered through 0.45 µm pore diameter filter. The clear cell-free extract was concentrated by filtering through a 30000 Dalton filter (Vivaspin 20, GE Healthcare) by following the supplied protocol. A gravity flow Sephadex G50 superfine (Pharmacia Chemicals, Sweden) column was prepared with 1 g of column material (prepared by boiling in 100 mL water for 1 hour, cooled to room temperature). A column was prepared by applying 20 mL of the cooled slurry on a 30 mL filtration column. The column was washed with MilliQ water and equilibrated with wash buffer B (50 mM of $NaH_2PO_4$ buffer, pH 7.0). 500 µL of the concentrated supernatant was applied on the column and allowed the supernatant to enter in the column bed. The wash buffer (50 mM of $NaH_2PO_4$ buffer, pH 7.0) was applied on top of the column and the eluent fractions were collected individually. The collected fractions were analyzed on SDS-PAGE gel (containing 10% acrylamide). The protein fractions were combined together and buffer was exchanged against the storage buffer (50 mM $KH_2PO_4$ buffer pH 7.0 containing 10 mM NaCl, 1 mM $MgCl_2$) with the desalting column as described in earlier section. The purified enzymes were stored at 4° C. until further use.

Example 5: Protein Concentration Measurement Using BCA Assay

The concentration of purified lactases was determined using Pierce™ BCA protein assay kit (Thermo Fisher Scientific, Germany) by following the protocol supplied with the kit.

Example 6: Activity Determination Using Purified Enzymes on Lactose as Substrate at pH 6.7 at 37° C.

To measure the beta-galactosidase activity, the purified lactases were diluted to 40× in buffer A (50 mM $NaH_2PO_4$ buffer pH 6.7 containing 100 µM of $MgSO_4$). In a separate reaction, the diluted enzyme was incubated with lactose solution prepared in buffer B (140 mM of lactose prepared in 100 mM sodium-citrate buffer of pH 6.7, containing 100 µM of $MgSO_4$). The reaction mixture was prepared by mixing 13 µL of diluted enzyme and 37 µL of lactose solution in a PCR tube. The reaction mixture was incubated in a DNA thermal cycler with the following incubation parameters (reaction time; 10 min at 37° C., enzyme inactivation; 10 min at 95° C., cooling; 4° C.). The reaction mixtures were stored at −20° C. until further use. To determine the amount of glucose formed during the reaction, 10 µL of the reaction mixture was transferred to one well of standard microtiter plate (Thermo Fischer Scientific, Denmark) containing 80 µL of buffer C (100 mM of $NaH_2PO_4$ buffer, pH 7.0, containing glucose oxidase; 0.6 g/L (Sigma Aldrich), 2,2'-azino-bis(3-ethylbenzothiazoline-6-sulfonic acid diammonium salt); ABTS: 1.0 g/L (Sigma Aldrich), horseradish peroxidase; 0.02 g/L (Sigma Adrich)) and incubated at 30° C. for 40 min. After 40 min, the absorbance was determined at 610 nm using FLUOStar Omega UV-plate reader (BMG Labtech, Germany). The absorbance values between 0.1 and 1.5 were used for calculations, if the A610 nm value>1.5, the reaction mixture was diluted up to 10× with buffer A. With each purified enzyme, the reactions were carried out in triplicate and the mean value of the triplicate measurement was used for calculation. The protein purification performed with the E. coli cells transformed with the empty pBAD/His was used for normalization. Using a known concentration of glucose (0-2.5 mM), a standard curve was drawn and the slope of the curve was used to calculate the glucose formed during the reaction. The maximum absorbance value for each lactase was used to determine μM of glucose formed per sec, described as 1 Unit of Activity with Lactose at pH 6.7 at 37° C. (UAL-1). The specific activity at pH 6.7 at 37° C. is defined as μM of glucose formed per second per μM of enzyme (μM of glucose/sec/μM of enzyme) and determined by dividing UAL-1 by the protein concentration in μM, described as SUAL-1. The specific activity of SEQ ID NO:34 and SEQ ID NO:35 were determined under the similar conditions. The high specific activity at pH 6.7 is highly desired for robustness for the enzyme in fresh and fermented milk applications. The detail results of the specific activity of enzymes at pH 6.7 at 37° C. are described in FIG. 1.

Additionally the activity was described as μmole of glucose formed per minute per milligram of enzyme added. The results are shown in FIG. 14.

Example 7: Activity Determination Using Purified Enzymes in the Presence of Galactose at pH 6.7 at 37° C.

The purified lactases were diluted to 40× in buffer A (50 mM NaH$_2$PO$_4$ buffer pH 6.7 containing 100 μM of MgSO$_4$). In separate reactions, the diluted enzymes were incubated with buffer D (140 mM of lactose and 140 mM of galactose prepared in 100 mM sodium-citrate buffer of pH 6.7, containing 100 μM of MgSO$_4$). The reaction mixture consists of 13 μL of the diluted enzyme and 37 μL of buffer D in a PCR tube. The reaction mixture was incubated in thermal cycler with the following incubation parameters (reaction time: 10 min at 37° C., enzyme inactivation: 10 min at 95° C., cooling: 4° C.). The reaction mixtures were stored at −20° C. until further use. To determine the amount of glucose formed during the reaction, 10 μL of the reaction mixture was transferred to one well of standard microtiter plate (Thermo Fischer Scientific, Denmark) containing 80 μL of buffer C (100 mM of NaH$_2$PO$_4$ buffer, pH 7.0, containing glucose oxidase; 0.6 g/L (Sigma Aldrich), 2,2'-azino-bis(3-ethylbenzothiazoline-6-sulfonic acid diammonium salt); ABTS: 1.0 g/L (Sigma Aldrich), horseradish peroxidase; 0.02 g/L (Sigma Adrich)) and incubated at 30° C. for 40 min. After 40 min, the absorbance was determined at 610 nm using FLUOStar Omega UV-plate reader (BMG Labtech, Germany). The absorbance values between 0.1 and 1.5 were used for calculations, if the A610 nm value>1.5, the reaction mixture was diluted up to 10× with buffer A. With each purified enzyme, the reactions were carried out in triplicate and the mean value of the triplicate measurement was used for calculation. The protein purification performed with the E. coli cells transformed with the empty pBAD/His was used for normalization. Using a known concentration of glucose (0-2.5 mM), a standard curve was drawn and the slope of the curve was used to calculate the absorbance corresponding to 1 μM of glucose formed during the reaction. The maximum absorbance value for each lactase was used to determine μM of glucose formed per sec, described as 1 Unit of Activity with Galactose at pH 6.7 at 37° C. (UAG). The specific activity at pH 6.7 at 37° C. in presence of galactose is defined as μM of glucose formed per second per μM of enzyme (μM of glucose/sec/μM of enzyme) and determined by dividing UAG by the protein concentration in μM, described as SUAG.

The percentage inhibition of enzymes with galactose is calculated by using the formula % inhibition=100*(A−B)/A Where A is specific activity in of enzymes with lactose at pH 6.7 at 37° C. (SUAL) as described in the example 6, and B stand for the specific activity of enzymes in presence of galactose at pH 6.7 at 37° C. (SUAG) as described in the example 7. The detail results of the % galactose inhibition are described the FIG. 2 and FIG. 14. The lower galactose inhibition is highly relevant for the applications where very low lactose concentration is desired. Additionally the activity was described as μmole of glucose formed per minute per milligram of enzyme added. The results are shown in FIG. 14.

Note: relatively high standard deviations in galactose inhibition measurement are due to trace amounts of glucose impurities in purchased galactose.

Example 8: Activity Determination Using Purified Enzymes on Lactose as Substrate at pH 6.7 at 4° C.

The purified lactases were diluted up to 40× in buffer A (50 mM NaH$_2$PO$_4$ buffer pH 6.7 containing 100 μM of MgSO$_4$). In a separate reaction, the diluted enzyme was incubated with lactose solution prepared in buffer B (140 mM of lactose prepared in 100 mM sodium-citrate buffer of pH 6.7, containing 100 μM of MgSO$_4$). The reaction mixture was prepared by mixing 13 μL of diluted purified enzyme and 37 μL of lactose solution in a PCR tube. The reaction mixture was incubated in a DNA thermal cycler using the following incubating parameters (reaction time; 60 min at 4° C., enzyme inactivation; 10 min at 95° C., storage; 4° C.). The reaction mixtures were stored at −20° C. freezer until further use. The amount of glucose formed during the reaction was determined by following the protocol described in example 6. The maximum absorbance value for each lactase was used to determine μM of glucose formed per sec, described as 1 Unit of Activity with Lactose at pH 6.7 at 4° C. (UAL-2). The specific activity at pH 6.7 at 4° C. is defined as μM of glucose formed per second per μM of enzyme (μM of glucose/sec/μM of enzyme), and is determined by dividing UAL-2 by the protein concentration in μM, described as SUAL-2. The high specific activity at pH 6.7 at 4° C. is highly desired for the lactose hydrolysis for fresh/pasteurized milk applications. The detail results of the specific activity of enzymes at pH 6.7 at 4° C. are described in the FIG. 3. Additionally the activity was described as μmole of glucose formed per minute per milligram of enzyme added. The results are shown in FIG. 14.

Example 9: Activity Determination Using Purified Enzymes on Lactose as Substrate at pH 6.7 at 43° C.

The purified lactases were diluted to 40× in buffer A (50 mM NaH$_2$PO$_4$ buffer pH 6.7 containing 100 μM of MgSO$_4$). In a separate reaction, the diluted enzyme was incubated with lactose solution prepared in buffer B (140 mM of lactose prepared in 100 mM sodium-citrate buffer of pH 6.7, containing 100 µM of $MgSO_4$). The reaction mixture was prepared by mixing 13 µL of diluted purified enzyme and 37 µL of lactose solution in a PCR tube. The reaction mixture was incubated in a DNA thermal cycler using the following incubating parameters (reaction time; 10 min at 43° C., enzyme inactivation; 10 min at 95° C., storage; 4° C.). The reaction mixtures were stored at −20° C. freezer until further use. The amount of the glucose formed during the reaction was determined by following the protocol described in example 6. The maximum absorbance value for each lactase was used to determine µM of glucose formed per sec, described as 1 Unit of Activity with Lactose at pH 6.7 at 43° C. (UAL-3). The specific activity at pH 6.7 at 43° C. is defined as µM of glucose formed per second per µM of enzyme (µM of glucose/sec/µM of enzyme), and is determined by dividing UAL-3 by the protein concentration in µM, described as SUAL-3. The high specific activity at pH 6.7 at 43° C. is highly desired for the lactose hydrolysis for the fermented milk applications. The detail results of the specific activity of enzymes at pH 6.7 at 43° C. are described in FIG. 4. Additionally the activity was described as µmole of glucose formed per minute per milligram of enzyme added. The results are shown in FIG. 14.

Example 10: Activity Determination Using Purified Enzymes on Lactose as Substrate at pH 5.5 at 4° C.

The purified lactases were diluted up to 40× in buffer A (50 mM $NaH_2PO_4$ buffer pH 6.7 containing 100 µM of $MgSO_4$). In a separate reaction, the diluted enzyme was incubated with lactose solution prepared in buffer E (140 mM of lactose prepared in 100 mM sodium-citrate buffer of pH 5.5, containing 100 µM of $MgSO_4$). The reaction mixture was prepared by mixing 13 µL of diluted purified enzyme and 37 µL of lactose solution in a PCR tube. The reaction mixture was incubated in a DNA thermal cycler using the following incubating parameters (reaction time; 60 min at 4° C., enzyme inactivation; 10 min at 95° C., storage; 4° C.). The substrate solution was prepared in a buffer of pH 5.5 and enzyme solution had a pH of 6.7. To initiate the reaction, 13 µL of enzyme was added to 37 µL of substrate solution. This mixing of these two buffers eventually increases the reaction pH from 5.5 to 5.7. The reaction mixtures were stored at −20° C. freezer until further use. To determine the amount of glucose formed during the reaction, 10 µL of the reaction mixture was transferred to one well of standard microtiter plate containing 80 µL of buffer C and incubated at 30° C. for 40 min. After 40 min, the absorbance was determined at 610 nm using FLUOStar Omega UV-plate reader (BMG Labtech, Germany). The absorbance value between 0.1 and 1.5 were used for calculations, if the A610 nm value>1.5, the reaction mixture was diluted up to 5× with buffer A. With each purified enzyme, the reactions were carried out in triplicate and the mean value of the triplicate measurement was used for calculations. The maximum absorbance value for each lactase was used to determine µM of glucose formed per sec, described as 1 Unit of Activity with Lactose at pH 5.5 at 4° C. (UAL-4). The specific activity at pH 5.5 at 4° C. is defined as µM of glucose formed per second per µM of enzyme (µM glucose/sec/µM of enzyme), and is determined by dividing UAL-4 by the protein concentration in µM, described as SUAL-4. The high specific activity at pH 5.5 at 4° C. is relevant for the lactose hydrolysis in the fermented milk applications. The detail results of the specific activity of enzymes at pH 5.5 at 4° C. are described in the FIG. 5. Additionally the activity was described as µmole of glucose formed per minute per milligram of enzyme added. The results are shown in FIG. 15.

Example 11: Activity Determination Using Purified Enzymes on Lactose as Substrate at pH 5.5 at 37° C.

The purified lactases were diluted up to 40× in buffer A (50 mM $NaH_2PO_4$ buffer pH 6.7 containing 100 µM of $MgSO_4$). In a separate reaction, the diluted enzyme was incubated with lactose solution prepared in buffer E (140 mM of lactose prepared in 100 mM sodium-citrate buffer of pH 5.5, containing 100 µM of $MgSO_4$). The reaction mixture was prepared by mixing 13 µL of diluted purified enzyme and 37 µL of lactose solution in a PCR tube. The substrate solution was prepared in a buffer of pH 5.5 and enzyme solution had a pH of 6.7. To initiate the reaction, 13 µL of enzyme was added to 37 µL of substrate solution. This mixing of these two buffers eventually increases the reaction pH from 5.5 to 5.7. The reaction mixture was incubated in a DNA thermal cycler using the following incubating parameters (reaction time; 10 min at 37° C., enzyme inactivation; 10 min at 95° C., storage; 4° C.). The reaction mixtures were stored at −20° C. until further use. The amount of glucose formed during the reaction was determined by following the protocol as described in the example 10. The maximum absorbance value for each lactase was used to determine µM of glucose formed per sec, described as 1 Unit of Activity with Lactose at pH 5.5 at 37° C. (UAL-5). The specific activity at pH 5.5 at 37° C. is defined as µM of glucose formed per second per µM of enzyme (µM of glucose/sec/µM of enzyme), and is determined by dividing UAL-5 by the protein concentration in µM, described as SUAL-5. The high specific activity at pH 5.5 at 37° C. is relevant for the lactose hydrolysis in the fermented milk applications and sweet whey lactose hydrolysis. The detail results of the specific activity of enzymes at pH 5.5 at 37° C. are described in the FIG. 6. Additionally the activity was described as µmole of glucose formed per minute per milligram of enzyme added. The results are shown in FIG. 15.

Example 12: Activity Determination Using Purified Enzymes on Lactose as Substrate at pH 5.5 at 43° C.

The purified lactases were diluted up to 40× in buffer A (50 mM $NaH_2PO_4$ buffer pH 6.7 containing 100 µM of $MgSO_4$). In a separate reaction, the diluted enzyme was incubated with lactose solution prepared in buffer E (140 mM of lactose prepared in 100 mM sodium-citrate buffer of pH 5.5, containing 100 µM of $MgSO_4$). The reaction mixture was prepared by mixing 13 µL of diluted purified enzyme and 37 µL of lactose solution in a PCR tube. The substrate solution was prepared in a buffer of pH 5.5 and enzyme solution had a pH of 6.7. To initiate the reaction, 13 µL of enzyme was added to 37 µL of substrate solution. This mixing of these two buffers eventually increases the reaction pH from 5.5 to 5.7.

The reaction mixture was incubated in a DNA thermal cycler using the following incubating parameters (reaction time; 10 min at 43° C., enzyme inactivation; 10 min at 95° C., storage; 4° C.). The reaction mixtures were stored at −20° C. until further use. The amount of glucose formed during the reaction was determined by following the protocol described in the example 10. The maximum absorbance value for each lactase was used to determine µM of glucose formed per sec, described as 1 Unit of Activity with Lactose at pH 5.5 at 43° C. (UAL-6). The specific activity at pH 5.5 at 43° C. is defined as µM of glucose formed per second per µM of enzyme (µM of glucose/sec/µM of enzyme), and is determined by dividing UAL-6 by the protein concentration in µM, described as SUAL-6. The high specific activity at pH 5.5 at 43° C. is relevant for the lactose hydrolysis in the fermented milk applications and sweet whey lactose hydrolysis. The detail results of the specific activity of enzymes at pH 5.5 at 43° C. are described in the FIG. 7. Additionally the activity was described as µmole of glucose formed per minute per milligram of enzyme added. The results are shown in FIG. 15.

Example 13: Activity Determination Using Purified Enzymes on Lactose as Substrate at pH 4.5 at 4° C.

The purified lactases were diluted up to 40x in buffer A (50 mM $NaH_2PO_4$ buffer pH 6.7 containing 100 µM of $MgSO_4$). In a separate reaction, the diluted enzyme was incubated with lactose solution prepared in buffer F (140 mM of lactose prepared in 100 mM sodium-citrate buffer of pH 4.5, containing 100 µM of $MgSO_4$). The reaction mixture was prepared by mixing 13 µL of diluted purified enzyme and 37 µL of lactose solution in a PCR tube. The substrate solution was prepared in a buffer of pH 4.5 and enzyme solution had a pH of 6.7. To initiate the reaction, 13 µL of enzyme was added to 37 µL of substrate solution. This mixing of these two buffers eventually increases the reaction pH from 4.5 to 4.7.

The reaction mixture was incubated in a DNA thermal cycler using the following incubating parameters (reaction time; 60 min at 4° C., enzyme inactivation; 10 min at 95° C., storage; 4° C.). To determine the amount of glucose formed during the reaction, 10 µL of the reaction mixture was transferred to one well of standard microtiter plate containing 80 µL of buffer C (as described in example 6) and incubated at 30° C. for 40 min. After 40 min, the absorbance was determined at 610 nm using FLUOStar Omega UV-plate reader. The absorbance value between 0.1 and 1.5 were used for calculations, if the A610 nm value>1.5, the reaction mixture was diluted up to 5x with buffer A. With each purified enzyme, the reactions were carried out in triplicate and the mean value of the triplicate measurement was used for calculation. The maximum absorbance value for each lactase was used to determine µM of glucose formed per sec, described as 1 Unit of Activity with Lactose at pH 4.5 at 4° C. (UAL-7). The specific activity at pH 4.5 at 4° C. is defined as µM of glucose formed per second per µM of enzyme (µM of glucose/sec/µM of enzyme), and is determined by dividing UAL-7 by the protein concentration in µM, described as SUAL-7. The high specific activity at pH 4.5 at 4° C. is relevant for the lactose hydrolysis in the fermented milk applications. The detail results of the specific activity of enzymes at pH 4.5 at 4° C. are described in the FIG. 8. Additionally the activity was described as µmole of glucose formed per minute per milligram of enzyme added. The results are shown in FIG. 16.

Example 14: Activity Determination Using Purified Enzymes on Lactose as Substrate at pH 4.5 at 37° C.

The purified lactases were diluted up to 40x in buffer A (50 mM $NaH_2PO_4$ buffer pH 6.7 containing 100 µM of $MgSO_4$). In a separate reaction, the diluted enzyme was incubated with lactose solution prepared in buffer F (140 mM of lactose prepared in 100 mM sodium-citrate buffer of pH 4.5, containing 100 µM of $MgSO_4$). The reaction mixture was prepared by mixing 13 µL of diluted purified enzyme and 37 µL of lactose solution in a PCR tube. The substrate solution was prepared in a buffer of pH 4.5 and enzyme solution had a pH of 6.7. To initiate the reaction, 13 µL of enzyme was added to 37 µL of substrate solution. This mixing of these two buffers eventually increases the reaction pH from 4.5 to 4.7.

The reaction mixture was incubated in a DNA thermal cycler using the following incubating parameters (reaction time; 10 min at 37° C., enzyme inactivation; 10 min at 95° C., storage; 4° C.). The reaction mixtures were stored at −20° C. until further use. The amount of glucose formed during the reaction was determined by following the protocol described in the example 13. The maximum absorbance value for each lactase was used to determine µM of glucose formed per sec, described as 1 Unit of Activity with Lactose at pH 4.5 at 37° C. (UAL-8). The specific activity at pH 4.5 at 37° C. is defined as µM of glucose formed per second per µM of enzyme (µM of glucose/sec/µM of enzyme), and is determined by dividing UAL-8 by the protein concentration in µM, described as SUAL-8. The high specific activity at pH 4.5 at 37° C. is relevant for the lactose hydrolysis in the fermented milk applications and acidic whey lactose hydrolysis. The detail results of the specific activity of enzymes at pH 4.5 at 37° C. are described in the FIG. 9. Additionally the activity was described as µmole of glucose formed per minute per milligram of enzyme added. The results are shown in FIG. 16.

Example 15: Activity Determination Using Purified Enzymes on Lactose as Substrate at pH 4.5 at 43° C.

The purified lactases were diluted up to 40x in buffer A (50 mM $NaH_2PO_4$ buffer pH 6.7 containing 100 µM of $MgSO_4$). In a separate reaction, the diluted enzyme was incubated with lactose solution prepared in buffer F (140 mM of lactose prepared in 100 mM sodium-citrate buffer of pH 4.5, containing 100 µM of $MgSO_4$). The reaction mixture was prepared by mixing 13 µL of diluted purified enzyme and 37 µL of lactose solution in a PCR tube. The substrate solution was prepared in a buffer of pH 4.5 and enzyme solution had a pH of 6.7. To initiate the reaction, 13 µL of enzyme was added to 37 µL of substrate solution. This mixing of these two buffers eventually increases the reaction pH from 4.5 to 4.7. The reaction mixture was incubated in a DNA thermal cycler using the following incubating parameters (reaction time; 10 min at 43° C., enzyme inactivation; 10 min at 95° C., storage; 4° C.). The reaction mixtures were stored at −20° C. until further use. The amount of glucose formed during the reaction was determined by following the protocol described in the example 13. The maximum absorbance value for each lactase was used to determine µM of glucose formed per sec, described as 1 Unit of Activity with Lactose at pH 4.5 at 43° C. (UAL-9). The specific activity at pH 4.5 at 43° C. is defined as µM of glucose formed per second per µM of enzyme (µM of glucose/sec/µM of enzyme), and is determined by dividing UAL-9 by the protein concentration in µM, described as SUAL-9. The high specific activity at pH 4.5 at 43° C. is relevant for the lactose hydrolysis in the fermented milk applications and acidic whey lactose hydrolysis. The detail results of the specific activity of enzymes at pH 4.5 at 43° C. are described in the FIG. 10. Additionally the activity was described as µmole of glucose formed per minute per milligram of enzyme added. The results are shown in FIG. 16.

Example 16: Activity Determination in BLU Units

The commercially available NOLA™ Fit enzyme (Chr-Hansen, Denmark) was diluted in a range from 0.5 BLU/mL to 2.5 BLU/mL in buffer G (50 mM $NaH_2PO_4$ buffer pH 7.0 containing 100 µM of $MgSO_4$, 0.045% Brij, Sigma Aldrich). The diluted enzyme was incubated with lactose solution prepared in buffer H (105 mM of lactose prepared in 100 mM sodium-citrate buffer of pH 6.7, containing 100 µM of $MgSO_4$). The reaction mixture was prepared by mixing 13 µL of diluted purified enzyme and 37 µL of lactose solution in a PCR tube. The reaction mixture was incubated in a DNA thermal cycler using the following incubating parameters (reaction time; 10 min at 37° C., enzyme inactivation; 10 min at 95° C., storage; 4° C.). The amount of glucose conversion was determined by transferring 10 µL of the reaction mixture in a single well of standard microtiter plate containing 80 µL of buffer C and incubated at 30° C. for 40 min. After 40 min, the absorbance was determined at 610 nm using FLUOStar Omega UV-plate reader (BMG Labtech, Germany). The measured absorbance values were used to draw a standard curve against BLU/mL. The maximum slope of the curve was used to determine the activity of new enzymes in BLU/mL.

Example 17: Activity Determination of New Lactases in BLU/mL Using Lactose as Substrate The purified lactases were diluted up to 50× in buffer A (50 mM $NaH_2PO_4$ buffer pH 6.7 containing 100 µM of $MgSO_4$). In a separate reaction, the diluted enzyme was incubated with lactose solution prepared in buffer H (105 mM of lactose prepared in 100 mM sodium-citrate buffer of pH 6.7, containing 100 µM of $MgSO_4$). The reaction mixture was prepared by mixing 13 µL of diluted purified enzyme and 37 µL of lactose solution in a PCR tube. The reaction mixture was incubated in a DNA thermal cycler using the following incubating parameters (reaction time; 10 min at 37° C., enzyme inactivation; 10 min at 95° C., storage; 4° C.). After the reaction, 10 µL of the reaction mixture was transferred to one well of standard microtiter plate containing 80 µL of buffer C (as described in example 6) and incubated at 30° C. for 40 min. After 40 min, the absorbance was determined at 610 nm using FLUOStar Omega UV-plate reader. The absorbance value between 0.1 and 1.5 were used for calculations, if the A610 nm value>1.5, the reaction mixture was diluted up to 5× with buffer A. The maximum absorbance values were used to calculate the enzyme activity in BLU/mL, using standard curve described in example 16.

Example 18: Percentage Residual Lactose Measurement in Fresh Milk at Cold Temperature 2 mL of commercial pasteurized milk (1.5% Fat pasteurized milk, Arla Food) was mixed with 10-125 µL of enzyme (equivalent to 10 BLU/mL) as determined in the example 17, in 10 mL glass tube. The samples were incubated under constant conditions for 24 hours at 4° C. After the incubation, the reaction was stopped by heat inactivation at 95° C. for 7 min, followed by storage at −20° C. until further use. The amount of remaining lactose in the milk was analyzed using an HPLC assay. Samples for analysis were treated with 1.8 mL protein precipitation solution (0.083 M PCA and 2 mM Na-EDTA) and 2 mL of MQW prior to centrifugation at 2800 rpm for 30 min at 4° C. An aliquot of the supernatant was diluted a total of 200-fold using a Janus dilution robot (PerkinElmer, Waltham, MaA, USA). The diluted samples were analyzed on a Dionex ICS-5000 system (Thermo Fischer Scientific, Waltham (MA), USA) using 4×250 mm CarboPac SA20 analytical column (Thermo Fischer Scientific, Waltham, MA, USA) and a pulsed amperometric detector. The detector was set to a simple three-step potential waveform, selective for detection of carbohydrates. The eluent was set to 1 mM KOH and was continuously regenerated through a trap column (CR-TC, Thermo Fischer Scientific, Waltham (MA), USA). The flow rate of the eluent was 1.2 mL/min and the analysis time was 10 min per injection. The lactose in each sample was quantified using a three-point external calibration curve prepared by adding known amounts of lactose monohydrate (Sigma-Aldrich, St. Louis, MO, USA) to MQW. Concentrations were calculated based on the chromatographic peak heights. The measured percentage residual lactose in fresh milk is shown in FIG. 11.

Example 19: Activity Determination in UHT Milk at Room Temperature 2 mL of UHT milk (1.5% Fat UHT milk, Arla Food) was mixed with 2-25 µL of enzyme (equivalent to 2 BLU/mL) as determined in example 17, in 10 mL glass tube. The samples were incubated under constant conditions for 24 hours at 25° C. After the incubation, the reaction was stopped by heat inactivation at 95° C. for 7 min, followed by storage at −20° C. until further use. The amount of residual lactose in UHT milk was analyzed using HPLC by following the protocol as described in example 18. The percentage of residual lactose in fresh milk after hydrolysis is listed in the FIG. 12.

Example 20: Enzyme Performance at High Temperature in Buffer

The purified enzyme was diluted to 5 BLU/mL in buffer A (50 mM $NaH_2PO_4$ buffer pH 6.7 containing 100 µM of $MgSO_4$). In a separate reaction, 13 µL of the diluted enzyme was incubated in a DNA thermal cycler with lactose solution (105 mM lactose prepared in 100 mM sodium-citrate buffer of pH 6.7, containing 100 µM of $MgSO_4$). The reaction mixture was prepared by mixing 13 µL of enzyme and 37 µL of lactose solution in a PCR tube. The reaction mixture was incubated in a DNA thermal cycler using the following incubating parameters (reaction time; 10 min at 37° C., enzyme inactivation; 10 min at 95° C., storage; 4° C.). After the reaction, 10 µL of the reaction mixture was transferred to one well of standard microtiter plate containing 80 µL of buffer C (as described in example 6) and incubated at 30° C. for 40 min. After 40 min, the absorbance was determined at 610 nm using FLUOStar Omega UV-plate reader. The absorbance value between 0.1 and 1.5 were used for calculations, if the A610 nm value>1.5, the reaction mixture was diluted up to 5× with buffer A. The measured absorbance was called Abs37° C., and considered as reference value for calculations.

To measure the impact of heat treatment on enzyme activity, in a separate reaction, 13 µL of the diluted enzyme (5 BLU/mL) was incubated in a DNA thermal cycler using the following incubating parameter (at 72° C. for 15 sec or 74° C. for 15 sec or 76° C. for 6 sec or 78° C. for 6 sec or 80° C. for 4 sec or 85° C. for 5 sec or 90° C. for 5 sec or 95°

C. for 5 sec, followed by storage at 4° C.). The activity of the heat treated enzyme was determined by incubation with the lactose solution (105 mM lactose prepared in 100 mM sodium-citrate buffer of pH 6.7, containing 100 μM of MgSO$_4$), as described above. The measured absorbance at different temperature (for example at 72° C., 74° C., 76° C., 78° C., 80° C., 85° C., 90° C. or 95° C.) was called as Abs72° C., Abs74° C., Abs76° C., Abs78° C., Abs80° C., Abs85° C., Abs90° C., Abs95° C.

The percentage residual activity at high temperature was determined using the formula, % residual activity=(Abs72° C./Abs37° C.)*100

The percentages residual activities of different enzymes at different temperature are described in FIG. 13.

Example 21: Percentage Residual Lactose after the High Heat Treatment

The effect of heat treatment on the enzyme performance in pasteurized milk was determined by incubating a fixed amount of enzyme in the milk followed by a heat treatment. In separate reactions, 50 μL of the pasteurized milk was mixed with 10 BLU/mL of purified enzyme (as determined in example 17), in a PCR tube. The milk sample was incubated at 72° C. for 15 or 76° C. for 10 sec or 85° C. for 5 sec and 90° C. for 5 sec, followed by incubation at 5° C. for 24 h. After 24 h at 5° C., the reaction was stopped by heating the reaction at 95° C. for 7 min, followed by storage at −20° C. The residual lactose was measured by using the LactoSens® assay kit (Chr. Hansen, Denmark), by following the supplied protocol. The measured residual lactose was determined in g/L was determined at different temperature. The detection limit of the LactoSens® kit is between 0.2 g/L to 10 g/L. The results are described in the table 2.

TABLE 2

The percentage residual lactose in the pasteurized milk treated with a fixed amount of the purified enzyme followed by incubation at different temperature (72° C. for 15 sec, 76° C. for 10 sec, 85° C. for 5 sec and 90° C. for 5 sec followed by incubation at 4 C. for 24 h), determined using LactoSens ® assay kit. The LactoSens ® kit detection limits are in range of 0.2 g/L to 10 g/L of lactose. Here ND; not determined.

| G-number | Residual lactose at 4° C. (g/L) | Residual lactose at 72° C. (g/L) | Residual lactose at 76° C. (g/L) | Residual lactose at 85° C. (g/L) | Residual lactose at 90° C. (/L) |
|---|---|---|---|---|---|
| G4 | <0.2 | >10.0 | ND | ND | ND |
| G11 | <0.2 | >10.0 | ND | ND | ND |
| G16 | <0.2 | >10.0 | ND | ND | ND |
| G33 | <0.2 | 4.7 | ND | ND | ND |
| G35 | <0.2 | >10.0 | >10.0 | ND | ND |
| G40 | <0.2 | <0.2 | <0.2 | >10.0 | ND |
| G44 | 0.9 | >10.0 | ND | ND | ND |
| G57 | <0.2 | >10.0 | ND | ND | ND |
| G62 | 8.4 | >10.0 | >10.0 | >10.0 | ND |
| G66 | 0.35 | >10.0 | ND | ND | ND |
| G83 | 0.3 | 2.1 | 6.0 | >10.0 | ND |
| G84 | 0.25 | 0.65 | 0.5 | 7.6 | >10 |
| G95 | 0.3 | 6.0 | 8.6 | >10 | ND |
| G100 | 0.4 | 2.4 | 2.6 | >10.0 | ND |
| G104 | 0.35 | 0.45 | 0.5 | 0.45 | >10 |
| G108 | 0.35 | 1.3 | 1.55 | ND | ND |
| G109 | 0.35 | 1.45 | 3.4 | >10.0 | ND |
| G118 | 0.45 | 0.95 | 0.8 | >10.0 | >10 |
| G158 | <0.2 | 3.9 | >10.0 | ND | ND |
| G256 | 0.3 | 1.0 | 0.75 | 3.4 | >10 |
| G282 | <0.2 | <0.2 | <0.2 | <0.2 | >10 |
| G335 | <0.2 | 0.35 | 8.0 | >10.0 | ND |
| G600 | <0.2 | >10.0 | >10.0 | >10.0 | ND |
| G500 | <0.2 | >10.0 | ND | ND | ND |

The invention claimed is:

1. A dairy product comprising a milk-based substrate and a peptide exhibiting beta-galactosidase enzyme activity, wherein the amino acid sequence of the peptide is selected from SEQ ID NO: 9, 10, 11, and 16, enzymatically active fragments thereof, and amino acid sequences having not more than 22 amino acid substitutions, additions or deletions relative to the amino acid sequence selected from SEQ ID NO: 9, 10, 11, and 16, and enzymatically active fragments thereof.

2. A method for producing a dairy product according to claim 1, comprising:
adding the peptide exhibiting beta-galactosidase activity to a milk-based substrate comprising lactose; and
treating said milk-based substrate with said peptide.

3. The method according to claim 2, wherein said treating takes place at a pH within a range of 3-10.

4. The method according to claim 2, wherein all or a part of said treating takes place at a temperature of not more than 25° C.

5. The method according to claim 2, wherein all or a part of said treating takes place at a temperature of at least 25° C.

6. The method according to claim 2, wherein the galactose inhibition of said peptide or dimeric peptide is less than 60%.

7. The method according to claim 2, wherein said dairy product is a fermented milk product and said adding is performed during or prior to fermentation.

8. The method according to claim 7, which method does not require addition of a further enzyme after fermentation.

9. The method according to claim 2, wherein said dairy product is a fermented milk product and said adding is performed immediately following fermentation.

10. The method according to claim 2, wherein said dairy product is fresh milk and said adding is performed prior to, in conjunction with, or immediately following a step of pasteurization.

11. The method according to claim 2, wherein said dairy product is ultra-heat treatment (UHT) milk and said adding is performed prior to, in conjunction with, or immediately following a step of ultra-heat treatment.

12. The method according to claim 2, wherein said treating is started at a temperature of between 40° C. and 100° C.

13. The dairy product according to claim 1, wherein the amino acid sequence of the peptide is selected from SEQ ID NO: 9, 10, 11, and 16, and amino acid sequences having not more than 22 amino acid substitutions, additions, or deletions relative to the amino acid sequence selected from SEQ ID NO: 9, 10, 11, and 16.

14. The dairy product according to claim 1, wherein the peptide has the amino acid sequence of SEQ ID NO:9.

15. The dairy product according to claim 1, wherein the peptide has the amino acid sequence of SEQ ID NO:10.

16. The dairy product according to claim 1, wherein the peptide has the amino acid sequence of SEQ ID NO:11.

17. The dairy product according to claim 1, wherein the peptide has the amino acid sequence of SEQ ID NO: 16.

18. The dairy product according to claim 1, wherein dairy product is selected from lactose-free milk, low-lactose milk, yogurt, cheese, fermented milk products, dietary supplements, and probiotic dietary products.

* * * * *

SEQUENCE LISTING

```
Sequence total quantity: 41
SEQ ID NO: 1            moltype = AA  length = 1049
FEATURE                 Location/Qualifiers
source                  1..1049
                        mol_type = protein
                        organism = Bifidobacterium adolescentis
SEQUENCE: 1
MADTAELAIV HATTASASWL TDPTVFAANR KPAHSSHRYV IGETSEPKQS LDGEWKVRIE  60
QARNVDVESA PFAAVDFEDG DFGAIEVPGH LQMAGYLKNK YVNIQYPWDG HEDPQAPNIP 120
ENNHVAIYRR RFALDAQLAR TLENDGTVSL TFHGAATAIY VWLDGTFVGY GEDGFTPSEF 180
DVTEALRNGN GNAADSPEAE HTLTVACYEY SSASWLEDQD FWRLHGLFRT VELAAQPHTH 240
VETVQLEADY TAADTAGTAD TAELNAALTL RNSADAMTIE STLRDGDGNV VWESTQACNG 300
EIALNSGKMT NIAPWSAESP TLYTLTVRVV GHDGAIIETV TQKIGFRTFR IENGIMTLNG 360
KRIVFKGADR HEFDAKRGRA ITREDMLSDV VFCKRHNINA IRTSHYPNQE YWYDLCDEYG 420
LYLIDETNME THGTWVANNV ERPEDGIPGS RPEWEGACVD RINSMMRRDY NHPSVLIWSL 480
GNESSAGEVF RAMYRHAHTI DPNRPVHYEG SVHMREFEDV TDIESRMYAH ADEIERYLND 540
GSPAHTDGPK KPYISCEYMH AMGNSCGNMD EYTALERYPM YQGGFIWDFI DQAIETKLPD 600
GTTRMCYGGD FGDRPSDYEF SGDGLLFADR TPSPKAQEVK QLYANVKIVV SVDEARITND 660
NLFVSTGDYR FVLRILADGK PVWSTTRRFD VAAGESASFE VDWPVDDYRS NAEELVLEVS 720
QQLGNACDWA PAGYELAFGQ CVVAGAKTTA DAVDAAGAPA DGTVTLGRWN AGVRGQGREA 780
LFSRTQGGMV SYTFGEREFV LRRPSITTFR PLTDNDRGAG HAFERAAWAV AGKYARCVDC 840
AIANRGENAV EATYTYELAI PQRTKVTVRY VADTAGLVSL DVEYPGEKNG DLPTIPAFGI 900
EWALPVEYAN LRFYGAGPEE TYADRRHAKL GVWSTTAGDD CAPYLLPQET GNHEDVRWAE 960
ITDDSGHGVR VKRGAGAKPF AMSLLPYSST MLEEALHQDE LPKPRHMFLR LLAAQMGVGG 1020
DDSWMSPVHE QYQLPADQPL SLNVQLKLF                                  1049

SEQ ID NO: 2            moltype = AA  length = 625
FEATURE                 Location/Qualifiers
source                  1..625
                        mol_type = protein
                        organism = Lactobacillus sakei
SEQUENCE: 2
MQPNIQWLDT PAVFRVGQLP AHSDHRYYAT LAEMAQQQSS FEQSLNGTWQ FHYSVNAASR  60
PKSFYELAFD AQDFEPITVP QHIELAGYEQ LHYINTMYPW EGHYYRRPAF STSDDKQHLG 120
```

```
MFSEADYNPV GSYLHHFDLT PALRNQRVII RFEGVEQAMY VWLNGQFIGY AEDSFTPSEF    180
DLTPYLKETD NCLAVEVHKR SSAAFIEDQD FFRFFGIFRD VKLLAKPRTH LEDLWVIPEY    240
DVVQQTGQVK LRLQFSGDEN RVHLRIRDQH QIILTADLTS AAQVNGLYKM PELVQAWSNQ    300
TPNLYTLELE VVDQAGETIE ISQQPFGFRK IEIKDKVMLL NGKRLVINGV NRHEWHPETG    360
RTITAEDEAW DIACMQRNHI NAVRTSHYPD RLSFYNGCDQ AGIYMMAETN LESHGSWQKM    420
GAVEPSWNVP GSYDEWEAAT LDRARTNFET FKNHVSILFW SLGNESYAGS VLEKMNAYYK    480
QQDPTRLVHY EGVFRAPEYK ATISDVESRM YATPAEIKAY LDNAPQKPFI LCEYMHDMGN    540
SLGGMQSYID LLSQYDMYQG GFIWDFIDQA LLVTDPVTGQ RELRYGGDFD DRPSDYEFSG    600
DGLVFATRDE KPAMQEVRYY YGEHK                                         625

SEQ ID NO: 3           moltype = AA  length = 330
FEATURE                Location/Qualifiers
source                 1..330
                       mol_type = protein
                       organism = Lactobacillus sakei
SEQUENCE: 3
MKNQQCRRLD TIMANTNKRL AVIFGDVTLG LKGPDFHYLF SYQTGGPESL RIQGKEWLYR     60
SPKPTFWRAT TDNDRGNQFP LKSGMWLAAD QFIACQSITV AIDGQTIPLP IAPENNRYSG    120
QETAQEVTVT YTYQTITTPQ TTVEVSYTIQ ASGKIRVAVT YHGQAGLPSL PVFGLRFVMP    180
TPATRFIYQG LSGETYPDRM AGGMAGEYEV TGLPVTPYLV PQDCGVHMAT DWVTIYRQAV    240
LDNRLREPVE TGLKFKMVDQ PFAFSCLPYT AEELENATHH SELPAPHRTV LSLLGAVRGV    300
GGIDSWGSDV EAAYQIDATQ DHHLEFEISF                                    330

SEQ ID NO: 4           moltype = AA  length = 1049
FEATURE                Location/Qualifiers
source                 1..1049
                       mol_type = protein
                       organism = Bifidobacterium adolescentis
SEQUENCE: 4
MADTAELAIV HATTASASWL TDPTVFAANR KPAHSSHRYV IGETSEPKQS LDGEWKVRIE     60
QARNVDVESA PFAAVDFEDG DFGAIEVPGH LQMAGYLKNK YVNIQYPWDG HEDPQAPNIP    120
ENNHVAIYRR RFALDAQLAR TLENDGTVSL TFHGAATAIY VWLDGTFVGY GEDGFTPSEF    180
DVTEALRNGN GNAADSPEAE HTLTVACYEY SSASWLEDQD FWRLHGLFRT VELAAQPHTH    240
VETVQLEADY TAADTAGTAD TAELNAALTL RNPADAMTIE STLRDGDGNV VWESTQACNG    300
EIALNSGKMT NIAPWSAESP TLYTLTVRVV GHDGAIIETV TQKIGFRTFR IENGIMTLNG    360
KRIVFKGADR HEFDAKRGRA ITREDMLSDV VFCKRHNINA IRTSHYPNQE YWYDLCDEYG    420
LYLIDETNME THGTWVANNV ERPEDGIPGS RPEWEGACVD RINSMMRRDY NHPSVLIWSL    480
GNESSAGEVF RAMYRHAHTI DPNRPVHYEG SVHMREFEDV TDIESRMYAH ADEIERYLND    540
GSPAHTDGPK KPYISCEYMH AMGNSCGNMD EYTALERYPM YQGGFIWDFI DQAIETKLPD    600
GTTRMCYGGD FGDRPSDYEF SGDGLLFADR TPSPKAQEVK QLYANVKIAV SVDEARITND    660
NLFVSTGDYR FVLRILADGK PVWSTTRRFD VAAGESASFE VDWPVDDYRS NAEELVLEVS    720
QQLGNACDWA PAGYELAFGQ CVVAGAKTTA DAVDAAGAPA DGTVTLGRWN AGVRGQGREA    780
LFSRTQGGMV SYTFGEREFV LRRPSITTFR PLTDNDRGAG HAFERAAWAV AGKYARCVDC    840
AIANRGENAV EATYTYELAI PQRTKVTVRY VADTAGLVSL DVEYPGEKNG DLPTIPAFGI    900
EWALPVEYAN LRFYGAGPEE TYADRRHAKL GVWSTTAGDD CAPYLLPQET GNHEDVRWAE    960
ITDDSGHGVR VKRGAGAKPF AMSLLPYSST MLEEALHQDE LPKPRHMFLR LLAAQMGVGG   1020
DDSWMSPVHE QYQLPADQPL SLNVQLKLF                                    1049

SEQ ID NO: 5           moltype = AA  length = 626
FEATURE                Location/Qualifiers
source                 1..626
                       mol_type = protein
                       organism = Lactobacillus amylovorus
SEQUENCE: 5
MKANIKWLDD PEVFRINQLP AHSDHPFYKD YREWQNHSSS FKQSLNGAWQ FHFSKDPQSR     60
PIDFYKRSFD SSSFDTIPVP SEIELNGYAQ NQYTNILYPW ESKIYRKPAY TLGRGIKDGD    120
FSQGKDNTVG SYLKHFDLNP ALAGHDIHIQ FEGVERAMYV YLNGHFIGYA EDSFTPSEFD    180
LTPYIQAKDN ILAVEVFKHS TASWLEDQDM FRFSGIFRSV ELLALPRTHL MDLDIKPTVV    240
NDYHDGVFNA KLHFMGKTSG NVHVLIEDID GKTLLNKKLP LKSTVEIENE TFANVHLWDN    300
HDPYLYQLII EVHDQDGKLV ELIPYQFGFR KIEITKDHVV LLNGKRLIIN GVNRHEWDAK    360
RGRSITLADM KQDIATFKHN NINAVRTCHY PNQIPWYYLC DQNGIYMMAE NNLESHGTWQ    420
KLGQVEATSN VPGSIPEWRE VVVDRARSNY ETFKNHTAIL FWSLGNESYA GSNIAAMNKL    480
YKDHDSSRLT HYEGVFHAPE FKKEISDLES CMYLPPKEAE EYLQNPKKPL VECEYMHDMG    540
TPDGGMGSYI KLIDKYPQYM GGFIWDFIDQ ALLVHDPVSG QDVLRYGGDF DDRHSDYEFS    600
GDGLMFADRT PKPAMQEVRY YYGLHK                                        626

SEQ ID NO: 6           moltype = AA  length = 316
FEATURE                Location/Qualifiers
source                 1..316
                       mol_type = protein
                       organism = Lactobacillus amylovorus
SEQUENCE: 6
MAYTNNLHVV YGEASLGVNG QDFAYLFSYE RGGLESLKIK DKEWLYRTPT PTFWRATTDN     60
DRGSGFNQKA AQWLGADMFT KCVGIHVQVD DHRFDELPVA PINNQFSNQE FAHEVKVAFD    120
YETLTTPATK VKIIYNINDF GHMTITMHYF GKKGLPPLPV IGMRFIMPTK AKSFDYTGLS    180
GETYPDRMAG AERGTFHIDG LPVTKYLVPQ ENGMHMQTNE LVITRNSTQN NADKDGDFSL    240
KITQTKQPFN FSLLPYTAEE LENATHIEEL PLARRSVLVI AGAVRGVGGI DSWGSDVEEQ    300
YHIDPEQDHE FSFTLN                                                   316
```

| SEQ ID NO: 7 | moltype = AA length = 1052 |
| --- | --- |
| FEATURE | Location/Qualifiers |
| source | 1..1052 |
| | mol_type = protein |
| | organism = Bifidobacterium bifidum |

SEQUENCE: 7

```
MNTTDDQRKN GDPIVSPSIP TTAWLADPRV YAVHRLDAHS DHACWSRSPV DGESTDLRQS    60
LDGEWRVRVE TAPTGRFPDG TSDGPDWISD VSPLFAAPGF DDSSFSRVQV PSHLETAGLL   120
APQYVNVQYP WDGHEDPKAP AIPEHGHVAV YRREFDADGE VAQAVREGRP VTLTFQGAAT   180
AIYVWLNGSF IGYAEDSFTP SEFDVTDAIK VDGNVLAVAC YEYSSASWLE DQDFWRLHGL   240
FRSVELNARP AAHVADLHAD ADWDLATSRG SLSLDVLIDG AANAATADFA LRDKNGTIVW   300
RTATKADGTL HAEAEIDDAA PWSAERPDLY ELSVTLLDAD GKVLETARTR IGFRHVAIED   360
GILKLNGKRL VFRGVNRHEF DCRRGRAITE EDMLWDIRFM KRHNINAVRT SHYPNQSRWY   420
ELCDEYGIYL IDETNLETHG SWNSPGDIPV GTSVPGDDEA WLGACIDRLD SMILRDRNHP   480
SVLVWSLGNE SYAGEVLKAM SAHAHQLDPG RPVHYEGVNW NHAYDGISDF ESRMYAKPAE   540
IQDWLEHGDE RGEASKPFVS CEYMHAMGNS CGGLSEFIDL ERYERYSGGF IWDYIDQGLV   600
QRLPDGSERL SVGGEWGDRP TDYEFVGNGI VFADRTPSPK AQEVKQLYSP VKLAPDGHGV   660
TIENRNLFAG TDGYVFAARL LEDGHEIWHA DYRFDVAAGD TQHHDIAFPD IDADGDTREV   720
TYEVDLLLAE ATAWAPAGYE LAFGQLTGTL NPEQDITETS HDDDGRATRT LSRWNAGIRR   780
DDEEILLSRT QGGIVSWKRD DREMVIRRPE LVTFRPLTDN DRGNHSGFDR AAWFAAGRYA   840
IVTETKIHES DDGLVAEYQY ELADPNHTPV SVTYHVNSDM RMQLTVEYPG NATDMASLPA   900
FGIEWELPGE YDRLRYYGPG PEETYRDRKQ GGKLGIWDAT AKASMAPYLM VQETGSHEDV   960
RWLEATDIQG HGLRVTQRGD RHFTASLLPW NTYTIEAARR HEDLPKPRHN YLRLLAAQMG  1020
VGGDDSWGAP VHTAYQLPAG RPLTDVNLE LI                                 1052
```

| SEQ ID NO: 8 | moltype = AA length = 1052 |
| --- | --- |
| FEATURE | Location/Qualifiers |
| source | 1..1052 |
| | mol_type = protein |
| | organism = Bifidobacterium bifidum |

SEQUENCE: 8

```
MNTTDDQRKN GDPIVSPSIP TTAWLADPRV YAVHRLDAHS DHACWSRSPV DGESTDLRQS    60
LDGEWRVRVE TAPTGRFPDG TSDGPDWISD VSPLFAAPGF DDSSFSRVQV PSHLETAGLL   120
APQYVNVQYP WDGHEDPKAP AIPEHGHVAV YRREFDADGE VAQAVREGRP VTLTFQGAAT   180
AIYVWLNGSF IGYAEDSFTP SEFDVTDAIK VDGNVLAVAC YEYSSASWLE DQDFWRLHGL   240
FRSVELNARP AAHVADLHAD ADWDLATSRG SLSLDVLIDG AANAATADFA LWDKNGTIVW   300
HIVTKADGTL HAEAEIDDAA PWSAERPDLY ELSVTLLDAD GKVLETARTR IGFRHVAIED   360
GILKLNGKRL VFRGVNRHEF DCRRGRAITE EDMLWDIRFM KRHNINAVRT SHYPNQSRWY   420
ELCDEYGIYL IDETNLETHG SWNSPGDIPV GTSVPGDDEA WLGACIDRLD SMILRDRNHP   480
SVLVWSLGNE SYAGEVLKAM SAHAHRLDPG RPVHYEGVNW NHAYDGISDF ESRMYAKPAE   540
IQDWLEHGDE RGEASKPFVS CEYMHAMGNS CGGLSEFIDL ERYERYSGGF IWDYIDQGLV   600
QRLPDGSERL SVGGEWGDRP TDYEFVGNGI VFADRTPSPK AQEVKQLYSP VKLAPDGHGV   660
TIENRNLFAG TDGYVFAARL LEDGHEIWHA DYRFDVAAGD TQHHDIAFPD IDADGDTREV   720
TYEVDLLLAE ATAWAPAGYE LAFGQLTGTL NPEQDITETS HDDDGRATRT LSRWNAGIRR   780
DDKEILLSRT QGGIVSWKRD DREMVIRRPE LVTFRPLTDN DRGNHSGFDR AAWFAAGRYA   840
IVTETKIHES DDGLVAEYQY ELADPNHTPV SVTYHVNSDM RMQLTVEYPG NATDMASLPA   900
FGIEWELPGE YDRLRYYGPG PEETYRDRKQ GGKLGIWDAT AKASMAPYLM VQETGSHEDV   960
RWLEATDIQG HGLRVTQRGD RHFTASLLPW NTYMIEAARR HEDLPEPRHN YLRLLAAQMG  1020
VGGDDSWGAP VHTAYQLPAG RPLTDVNLE LI                                 1052
```

| SEQ ID NO: 9 | moltype = AA length = 1055 |
| --- | --- |
| FEATURE | Location/Qualifiers |
| source | 1..1055 |
| | mol_type = protein |
| | organism = Bifidobacterium breve |

SEQUENCE: 9

```
MTNSMQGKAK TIMTNLQSAQ QFSQAWLTDP RVFAVNRLAA HSSHKFYDHS PQCGEAMDLK    60
QSLDGQWRVQ MLDLADLADN ELAEAAFAQP GYDAAGFSPI EVPSALETKG FLNHQYVNQQ   120
YPWSGHESPV APDVPKHNHV ALYRHEFSLE PKAAAVLEAN KTAADDAAKR RVTLTFQGAA   180
TAIVWLNGA FIGYAEDSFT PSEFDVTDVL RDGVNTLAVA CFEFSSASWL EDQDFWRLHG   240
IFRSVELEAQ PLVHVNDLRV LADYDHTTGE GSLDVVALLR NAGTAAAVAA TVLDAAGNTV   300
WHSKLTAGAD AETLTVKANV GKVNPWSAEE PTLYTLQVVA TDAAGQVIEA ALQRIGFRHF   360
AIEDGLMKLN GKRIVFKGVD RHEFDARTGR TIAEADMIED IHSFKRLNIN AVRTSHYPNE   420
TRWYELCDEY GIYVLDETNL ETHGSWTDPG DVFQPARAIP GSKDEWRAAC VDRTASMVRR   480
DYNHPSVVIW SLGNEAFGGD VFYSMRDFVH ENDPFRPVHY EGTFNDPEFS AATDIMSRMY   540
AKPDEIVKLY LGEDGKKPYI SCEYSHSMGN STGGLHLYTE LERYPLYQGG FIWDYVDQAL   600
WQDCGNGTER LAYGGDFEDR PNDYEFSGDG VMFADRTPSP KAQEVKQLYA NVKLVPDESG   660
VTITNDNLFI STASSLFTAR VLVDGAERWH ANYRFDVAAG ETVREPIAFP KVTDLVALSG   720
SAEVTYEVDQ RLAEATDWAP AGYELTFGQY VAAVSFDDGA ADAVVAGDAE VAADGFNAGI   780
HTDFGEVLLS KTQGGMVSFK RDGREMVIRR PNLTTFRALT DNDRGNGSGF ERAQWMAAGR   840
YARVTGTSVE ETADGKGLKA TYSYELADAK HTPVTVHYEV DAALRVHLTV EYPGEADAAT   900
LPAFGLEWIL PKQYDRLRFY GLGPEETYAD RLHGAKLGVF SRTAAEDCAP YLLPQETGNH   960
EQVRWAEITD EYGHGMRVTA AGGTRFATSL LPYSSLMFED ALHQNELPKP RHTFLRLLAA  1020
QMGVGGDDTW GAPVHDEFQV PADQPLKLDV TLELI                            1055
```

| SEQ ID NO: 10 | moltype = AA length = 689 |
| --- | --- |
| FEATURE | Location/Qualifiers |
| source | 1..689 |
| | mol_type = protein |

```
                            organism = Bifidobacterium catenulatum
SEQUENCE: 10
MTQRRSYRWP QPLAGQQARI WYGGDYNPDQ WPEEVWDDDV RLMKKAGVNL VSVGIFSWAK    60
IETSEGVYDF DWLDRIIDKL GEAGIAVDLA SATASPPMWL TQAHPEVLWK DYRGDVCQPG   120
ARQHWRPTSP VFREYALKLC RAMAEHYKGN PYVVAWHVSN EYGCHNRFDY SEDAERAFRK   180
WCEERYGTID AVNDAWGTAF WAQRMNDFTE IVPPRFIGDG NFMNPGKLLD FKRFSSDALK   240
AFYVAERDAL AEITPDLPLT TNFMVSAAGS VLDYDDWGRE VDFVSNDHYF IPGEAHLDEL   300
AFSASLVDGI ARKDPWFLME HSTSAVNWRP VNYRKEPGQL VRDSLAHVAM GADAVCYFQW   360
RQSKAGAEKF HSAMVPHTGE DSAVFRDVCE LGADLNTLAD NGLLGTKLAK SKVAVVFDYE   420
SEWATEHTAT PTQKVHHVDE PLQWFRALAD HGVTADVVPV SSNWDEYEVV VLPSVYILSE   480
ETTRRVRDYV VNGGRLIVTY YTGLSDEKDH VWLGGYPGSI RDVVGVRVEE FMPMGDDFPG   540
VPDCLGLSNG AVAHDIADVI GSVDGTATVL ETFRDDPWTG MDGAPAIVAN TFGEGRSVYV   600
GARLGRDGIA KSLPEIFESL GMAETGENDS RVLRVEREGS DGSRFVFSFN RTHEAVQIPF   660
EGKIVVSSFA EVSGENVSIK PNGVIVTKQ                                    689

SEQ ID NO: 11              moltype = AA   length = 1023
FEATURE                    Location/Qualifiers
source                     1..1023
                           mol_type = protein
                           organism = Bifidobacterium catenulatum
SEQUENCE: 11
MANSNRVEHA SETWLTDATV FEVNRTPAHS NHKCFTHDPQ SGEHSDLTQS LDGEWRVEIV    60
QASDIDFNEE PFVAENFDDS SFCRAQVPGH LQMAGLLKNK YVNIQYPWDG HENPLEPNVP   120
ENNHVALYRR KFVVSKRLAD TKESEGSVSI VFHGMATAIY VWVNGLFAGY GEDGFTPNEF   180
DITDLLHDGE NVVAVACYEY SSASWLEDQD FWRLHGLFRS VELTAQPHVH VENMQLEADW   240
DAESGTASLD AALSVRNASD AATISATLKD SEGNVVWEAS TNADANTTFA SGSLQGLEPW   300
SAESPSLYEL EVNVIDQAGN IVEAAVQKVG FRRFRIENGI MTLNGKRIVF KGADRHEFDA   360
KRGRSITEQD MIDDVIFCKR HNINAIRTSH YPNQERWYDL CDEYGIYLID ETNLETHGSW   420
CLPGDVVTAE TAVPGSKAHW EGACVDRVNS MVRRDYNHPS VVIWSLGNES YTGDVFRAMY   480
KHVHDIDPNR PVHYEGVTKN RDYDDVTDIE TRMYEHADVV EEYLKNDPQK PYISCEYMHA   540
MGNSVGNLDE YTALERYPHY QGGFIWDFID QAIYATQPDG STRLCYGGDF GDRPSDYEFS   600
GNGLVFADRT PTPKAQEVKQ LYSNVHIDVT DRSVSIKNDN LFISTGGYQF VLRILADGEP   660
VWQSERRFDV PADSACTFDV EWPVDLYRAN ADELVLEVSQ RLAEATDWAP AGYELAFGQT   720
IVAGTKAAED AALPADGIVT VGRWNAGVQG SGREILLSRT QGGLVSYTFD GHEFVLRRPA   780
ITTFRALTDN DRGAGHGFER AQWMVAGRYA RCVDNVIEQV DEDTLKAVYT YELATPQCTK   840
VTVGYTADTT GRLNLHVEYP GESGELPTIP AFGIEWTLPV QYSNLRFFGA GPEETYQDRK   900
HAKLGVWSTD AFKDHAPYLM PQETGNHEEV RWAEITDENG HGLRVSRANG AAPFAVSLQP   960
YSSFMIEEAQ HQDELPAPKH MFLRVLAAQM GVGGDDSWMS PVHSQYHITA DQPISLDVNL  1020
ELI                                                                1023

SEQ ID NO: 12              moltype = AA   length = 1008
FEATURE                    Location/Qualifiers
source                     1..1008
                           mol_type = protein
                           organism = Lactobacillus delbrueckii
                           note = subspecies bulgaricus
SEQUENCE: 12
MSNKLVKEKR VDQADLAWLT DPEVYEVNTI PPHSDHESFQ SQEELEEGKS SLVQSLDGDW    60
LIDYAENGQG PVNFYAEDFD DSNFKSVKVP GNLELQGFGQ PQYVNVQYPW DGSEEIFPPQ   120
IPSKNPLASY VRYFDLDEAF WDKEVSLKFD GAATAIYVWL NGHFVGYGED SFTPSEFMVT   180
KFLKKENNRL AVALYKYSSA SWLEDQDFWR MSGLFRSVTL QAKPRLHLED LKLTASLTDN   240
YQKGKLEVEA NIAYRLPNAS FKLEVRDSEG DLVAEKLGPI RSEQLEFTLA DLPVAAWSAE   300
KPNLYQVRLY LYQAGSLLEV SRQEVGFRNF ELKDGIMYLN GQRIVFKGAN RHEFDSKLGR   360
AITEEDMIWD IKTMKRSNIN AVRCSHYPNQ SLFYRLCDKY GLYVIDEANL ESHGTWEKVG   420
GHEDPSFNVP GDDQHWLGAS LSRVKNMMAR DKNHASILIW SLGNESYAGT VFAQMADYVR   480
KADPTRVQHY EGVTHNRKFD DATQIESRMY APAKVIEEYL TNKPAKPFIS VEYAHAMGNS   540
VGDLAAYTAL EKYPHYQGGF IWDWIDQGLE KDGHLLYGGD FDDRPTDYEF CGNGLVFADR   600
TESPKLANVK ALYANLKLEV KDGQLFLKND NLFTNSSSYY FLTSLLVDGK LTYQSRPLTF   660
GLEPGESGTF ALPWPEVADE KGEVVYRVTA HLKEDLPWAP GTFVAEAEE VAQKLPEFKP   720
EGRPDLVDSD YNLGLKGNNF QILFSKVKGW PVSLKYAGRE YLKRLPEFTF WRALTDNDRG   780
AGYGYDLARW ENAGKYARLK DISCEVKEDS VLVKTAFTLP VALKGDLTVT YEVDGRGKIA   840
VTADFPGAEE AGLLPAFGLN LALPKELTDY RYYGLGPNES YPDRLEGNYL GIYQGAVKKN   900
FSPYLRPQET GNRSKVRWYQ LFDEKGGLEF TANGADLNLS ALPYSAAQIE AADHAFDLTN   960
NYTWVRALSA QMGVGGDDSW GQKVHPEFCL DAQKARQLRL VIQPLLLK              1008

SEQ ID NO: 13              moltype = AA   length = 1007
FEATURE                    Location/Qualifiers
source                     1..1007
                           mol_type = protein
                           organism = Lactobacillus delbrueckii
                           note = subspecies lactis
SEQUENCE: 13
MSNKLVKEKR VDQADLAWLT DPEVYEVNTI PPHSDHESFQ SQEELEEGKS SLVQSLDGNW    60
LIDYAENGQG PINFYAEDFD DSNFKSVKVP GNLELQGFGQ PQYVNIQYPW DGSEEIFPPQ   120
VPSKNPLASY VRYFDLDEAL WDKEVSLKFA GAATAIYVWL NGHFVGYGED SFTPSEFMVT   180
KFLKKEGNRL AVALYKYSSA SWLEDQDFWR LSGLFRSVTL EAKPLLHLED LKLTASLTDN   240
YQKGKLEVEA NIAYRLPNAS FKLEVRDSEG DLVAEKVGPI RSEKLGFSLA DLPVAAWSAE   300
KPNLYQVRLY LYQAGSLLEV SRQEVGFRNF ELKDGIMYLN GQRIVFKGVN RHEFDSKLGR   360
AITEADMIWD IKTMKQSNIN AVRCSHYPNQ SLFYRLCDKY GLYVIDEANL ESHGTWEKVG   420
```

```
HEDPSFNVPG DDQHWLGASL SRVKNMMARD KNHASILIWS LGNESYAGTV FAQMADYVRK    480
ADPTRVQHYE GVTHNRKFDD ATQIESRMYA PAKEIEEYLT KKPAKPFISV EYAHAMGNSV    540
GDLAAYTALE KYPHYQGGFI WDWIDQGLEK DGHLLYGGDF DDRPTDYEFC GDGLVFADRT    600
TSPKLANVKA LYSNLKLEVK DGQLFIKNDN LFTNSSAYYF LASLLVDGKL TYQSQPLTFG    660
LEPGESGTFV LPWPEVEDEK GEIVYQVTAH LKEDLPWADE GFTVAEAEEA VTKLPEFYPA    720
GRPELVDSDF NLGLKGNGFR ILFSKAKGWP VSIKYAGREY LKRLPEFTFW RALTDNDRGA    780
GYGYDLAKWE NAGKYARLQD ISYEIKENSA LVKTTFTLPV ALKGDLTITY EVDSLGKIAV    840
TANFPGAVEN GLLPAFGLNF ALPKELSDYR YYGLGPNESY ADRLEGSYLG IYQGAVEKNF    900
TPYLRPQEAG NRSKVRYYQL FDEEGGLEFT ANGADLNLSA LPYSAAQIEA ADHAFELTNN    960
YTWVRALAAQ MGVGGDDSWG QKVHPEFCLD AQEARQLKLV IQPLLLK                 1007

SEQ ID NO: 14           moltype = AA  length = 1008
FEATURE                 Location/Qualifiers
source                  1..1008
                        mol_type = protein
                        organism = Lactobacillus delbrueckii
                        note = subspecies bulgaricus
SEQUENCE: 14
MSNKLVKEKR VDQADLAWLT DPEVYEVNTI PPHFDHESFQ SQEELEEGKS SLVQSLDGDW     60
LIDYAENGQG PVNFYAEDFD DSNFKSVKVP GNLELQGFGQ PQYVNVQYPW DGSEEIFPPQ    120
IPSKNPLASY VRYFDLDEAF WDKEVSLKFD GAATAIYVWL NGHFVGYGED SFTPSEFMVT    180
KFLKKENNRL AVALYKYSSA SWLEDQDFWR MSGLFRSVTL QAKPRLHLED LKLTASLTDN    240
YQKGKLEVEA NIAYRLPNAS FKLEVRDSEG DLVAEKLGPI RSEQLEFTLA DLPVAAWSAE    300
KPNLYQVRLY LYQAGSLLEV SRQEVGFRNF ELKDGIMYLN GQRIVFKGAN RHEFDSKLGR    360
AITEEDMIWD IKTMKRSNIN AVRCSHYPNQ SLFYRLCDKY GLYVIDEANL ESHGTWEKVG    420
GHEDPSFNVP GDDQHWLGAS LSRVKNMMAR DKNHASILIW SLGNESYAGT VFAQMADYVR    480
KADPTRVQHY EGVTHNRKFD DATQIESRMY APAKVIEEYL TNKPAKPFIS VEYAHAMGNS    540
VGDLAAYTAL EKYPHYQGGF IWDWIDQGLE KDGHLLYGGD FDDRPTDYEF CGNGLVFADR    600
TESPKLANVK ALYANLKLEV KDGQLFLKND NLFTNSSSYY FLTSLLVDGK LTYQSRPLTF    660
GLEPGESGTF ALPWPEVADE KGEVVYRVTA HLKEDLPWAD EGFTVAEAEA VAQKLPEFKP    720
EGRPDLVDSD YNLGLKGNNF QILFSKVKGW PVSLKYAGRE YLKRLPEFTF WRALTDNDRG    780
AGYGYDLARW ENAGKYARLK DISCEVKEDS VLVKTAFTLP VALKGDLTVT YEVDGRGKIA    840
VTADFPGAEE AGLLPAFGLN LALPKELTDY RYYGLGPNES YPDRLEGNYL GIYQGAVKKN    900
FSPYLRPQET GNRSKVRWYQ LFDEKGGLEF TANGADLNLS ALPYSAAQIE AADHAFELTN    960
NYTWVRALSA QMGVGGDDSW GQKVHPEFCL DAQKARQLRL VIQPLLLK                1008

SEQ ID NO: 15           moltype = AA  length = 1008
FEATURE                 Location/Qualifiers
source                  1..1008
                        mol_type = protein
                        organism = Lactobacillus delbrueckii
                        note = subspecies bulgaricus
SEQUENCE: 15
MSNKLVKEKR VDQADLAWLT DPEVYEVNTI PPHSDHESFQ SQEELEEGKS SLVQSLDGDW     60
LIDYAENGQG PVNFYAEDFD DSNFKSVKVP GNLELQGFGQ PQYVNVQYPW DGSEEIFPPQ    120
IPSKNPLASY VRYFDLDEAF WDKEVSLKFD GAATAIYVWL NGHFVGYGED SFTPSEFMVT    180
KFLKKENNRL AVALYKYSSA SWLEDQDFWR MSGLFRSVTL QAKPRLHLED LKLTASLTDN    240
YQKGKLEVEA NIAYRLPNAS FKLEVRDSEG DLVAEKLGPI RSEQLEFTLA DLPVAAWSAE    300
KPNLYQVRLY LYQAGSLLEV SRQEVGFRNF ELKDGIMYLN GQRIVFKGAN RHEFDSKLGR    360
AITEEDMIWD IKTMKRSNIN AVRCSHYPNQ SLFYRLCDKY GLYVIDEANL ESHGTWEKVG    420
GHEDPSFNVP GDDQHWLGAS LSRVKNMMAR DKNHASILIW SLGNESYAGT VFAQMADYVR    480
KADPTRVQHY EGVTHNRKFD DATQIESRMY APAKVIEEYL TNKPAKPFIS VEYAHAMGNS    540
VGDLAAYTAL EKYPHYQGGF IWDWIDQGLE KDGHLLYGGD FDDRPTDYEF CGNGLVFADR    600
TESPKLANVK ALYANLKLEV KDGQLFLKND NLFTNSSSYY FLTSLLVDGK LTYQSRPLTF    660
GLEPGESGTF ALPWPEVADE KGEVVYRVTA HLKEDLPWAD EGFTVAEAEA VAQKLPEFKP    720
EGRPDLVDSD YNLGLKGNNF QILFSKVKGW PVSLKYAGRE YLKRLPEFTF WRALTDNDRG    780
AGYGYDLARW ENAGKYARLK DISCEVKEDS VLVKTAFTLP VALKGDLTVT YEVDGRGKIA    840
VTADFPGAEE AGLLPAFGLN LALPKELTDY RYYGLGPNES YPDRLEGNYL GIYQGAVKKN    900
FSPYLRPQET GNRSKVRWYQ LFDEKGGLEF TANGADLNLS ALPYSAAQIE AADHAFELTN    960
NYTWVRALSA QMGVGGDDSW GQKVHPEFCL DAQKARQLRL VIQPLLLK                1008

SEQ ID NO: 16           moltype = AA  length = 1008
FEATURE                 Location/Qualifiers
source                  1..1008
                        mol_type = protein
                        organism = Lactobacillus delbrueckii
                        note = subspecies lactis
SEQUENCE: 16
MSNKLVKEKR VDQADLAWLT DPEVYEVNTI PPHSDHESFQ SQEELEEGKS SLVQSLDGDW     60
LIDYAENGQG PVNFYAEDFD DSNFKSVKVP GNLELQGFGQ PQYVNIQYPW DGSEEIFPPQ    120
VPSKNPLASY VRYFDLDEAF WDKEVSLKFA GAATAIYVWL NGHFVGYGED SFTPSEFMVT    180
KFLKKENNRL AVALYKYSSA SWLEDQDFWR LSGLFRSVTL QAKPLLHLED LKLTASLTDN    240
YQKGKLEVEA NIAYRLPNAS FKLEVRDSEG DLVAEKLGPI RSEQLEFTLA DLPVAAWSAE    300
KPNLYQVRLY LYQAGSLLEV SRQEVGFRNF ELKDGIMYLN GQRIVFKGVN RHEFDSKLGR    360
AITEEDMIWD IKTMKRSNIN AVRCSHYPNQ SLFYRLCDKY GLYVIDEANL ESHGTWEKVG    420
HEDPSFNVPG DDQHWLGASL SRVKNMMARD KNHASILIWS LGNESYAGTV FAQMADYVRK    480
ADPTRVQHYE GVTHNRKFDD ATQIESRMYA PAKEIEEYLT KKPAKPFISV EYAHAMGNSV    540
GDLAAYTALE KYPHYQGGFI WDWIDQGLEK DGHLLYGGGD FDDRPTDYEF CGNGLVFADR    600
TTSPKLANVK ALYSNLKLEV KDGQLFLKND NLFTNSSAYY FLTSLLVDGK LTYQSQPLTF    660
```

```
GLEPGESGTF VLPWPEVEDE KGEIVYQVTA HLKEDLPWAD EGFTVAEAEE AVTKLPEFYP   720
AGRPELVDSD FNLGLKGNGF RILFSKAKGW PVSIKYAGRE YLKRLPEFTF WRALTDNDRG   780
AGYGYDLAKW ENAGKYARLQ DISYEIKENS VLVKTAFTLP VALKGDLTIT YEVDSLGKIA   840
VTANFPGAVE NGLLPAFGLN FALPKELSDY RYYGLGPNES YADRLEGSYL GIYQGAVEKN   900
FTPYLRPQEA GNRSKVRYYQ LFDEESGLEF TANGADLNLS ALPYSAAQIE AADHAFELSN   960
NYTWVRALAA QMGVGGDDSW GQKVHPEFCL DAQEARQLKL VIQPLLLK                1008

SEQ ID NO: 17            moltype = AA  length = 1008
FEATURE                  Location/Qualifiers
source                   1..1008
                         mol_type = protein
                         organism = Lactobacillus delbrueckii
                         note = subspecies bulgaricus
SEQUENCE: 17
MSNKLVKEKR VDQADLAWLT DPEVYEVNTI PPHSDHESFQ SQEELEEGKS SLVQSLDGDW    60
LIDYAENGQG PVNFYAEDFD DSNFKSVKVP GNLELQGFGQ PQYVNVQYPW DGSEEIFPPQ   120
IPSKNPLASY VRYFDLDEAF WDKEVSLKFD GAATAIYVWL NGHFVGYGED SFTPSEFMVT   180
KFLKKENNRL AVALYKYSSA SWLEDQDFWR MSGLFRSVTL QAKPRLHLED LKLTASLTDN   240
YQKGKLEVEA NIAYRLPNAS FKLEVRDSEG DLVAEKLGPI RSEQLEFTLA DLPVAAWSAE   300
KPNLYQVRLY LYQAGSLLEV SRQEVGFRNF ELKDGIMYLN GQRIVFKGVN RHEFDSKLGR   360
AITEEDMIWD IKTIKRSNIN AVRCSHYPNQ SLFYRLCDKY GLYVIDEANL ESHGTWEKVG   420
GHEDPSFNVP GDDQHWLGAS LSRVKNMMAR DKNHASILIW SLGNESYAGT VFAQMADYVR   480
KADPTRVQHY EGVTHNRKFD DATQIESRMY APAKVIEEYL TNKPAKPFIS VEYAHAMGNS   540
VGDLAAYTAL EKYPHYQGGF IWDWIDQGLE KDGHLLYGGD FDDRPTDYEF CGNGLVFADR   600
TESPKLANVK ALYANLKLEV KDGQLFLKND NLFTNSSSYY FLTSLLVDGK LTYQSRPLTF   660
GLEPGESGTF ALPWPEVADE KGEVVYRVTA HLKEDLPWAD EGFTVAEAEE VAQKLPEFKP   720
EGRPDLVDSD YNLGLKGNNF QILFSKVKGW PVSLKYAGRE YLKRLPEFTF WRALTDNDRG   780
AGYGYDLARW ENAGKYARLK DISCEVKEDS VLVKTAFTLP VALKGDLTVT YEVDGRGKIA   840
VTADFPGAEE AGLLPAFGLN LALPKELTDY RYYGLGPNES YPDRLEGNYL GIYQGAVKKN   900
FSPYLRPQET GNRSKVRWYQ LFDEKGGLEF TANGADLNLS ALPYSAAQIE AADHAFELTN   960
NYTWVRALSA QMGVGGDDSW GQKVHPEFCL DAQKARQLRL VIQPLLLK                1008

SEQ ID NO: 18            moltype = AA  length = 1008
FEATURE                  Location/Qualifiers
source                   1..1008
                         mol_type = protein
                         organism = Lactobacillus delbrueckii
                         note = subspecies bulgaricus
SEQUENCE: 18
MSNKLVKEKR VDQADLAWLT DPEVYEVNTI PPHSDHESFQ SQEELEEGKS SLVQSLDGDW    60
LIDYAENGQG PVNFYAEDFD DSNFKSVKVP GNLELQGFGQ PQYVNVQYPW DGSEEIFPPQ   120
IPSKNPLASY VRYFDLDEAF WDKEVSLKFD GAATAIYVWL NGHFVGYGED SFTPSEFMVT   180
KFLKKENNRL AVALYKYSSA SWLEDQDFWR MSGLFRSVTL QAKPRLHLED LKLTASLTDN   240
YQKGKLEVEA NIAYRLPNAS FKLEVRDSEG DLVAEKLGPI GSEQLEFTLA DLPVAAWSAE   300
KPNLYQVRLY LYQAGSLLEV SRQEVGFRNF ELKDGIMYLN GQRIVFKGVN RHEFDSKLGR   360
AITEEDMIWD IKTIKRSNIN AVRCSHYPNQ SLFYRLCDKY GLYVIDEANL ESHGTWEKVG   420
GHEDPSFNVP GDDQHWLGAS LSRVKNMMAR DKNHASILIW SLGNESYAGT VFAQMADYVR   480
KADPTRVQHY EGVTHNRKFD DATQIESRMY APAKVIEEYL TNKPAKPFIS VEYAHAMGNS   540
VGDLAAYTAL EKYPHYQGGF IWDWIDQGLE KDGHLLYGGD FDDRPTDYEF CGNGLVFADR   600
TESPKLANVK ALYANLKLEV KDGQLFLKND NLFTNSSSYY FLTSLLVDGK LTYQSRPLTF   660
GLEPGESGTF ALPWPEVADE KGEVVYRVTA HLKEDLPWAD EGFTVAEAEE VAQKLPEFKP   720
EGRPDLVDSD YNLGLKGNNF QILFSKVKGW PVSLKYAGRE YLKRLPEFTF WRALTDNDRG   780
AGYGYDLARW ENAGKYARLK DISCEVKEDS VLVKTAFTLP VALKGDLTVT YEVDGRGKIA   840
VTADFPGAEE AGLLPAFGLN LALPKELTDY RYYGLGPNES YPDRLEGNYL GIYQGAVKKN   900
FSPYLRPQET GNRSKVRWYQ LFDEKGGLEF TANGADLNLS ALPYSAAQIE AADHAFELTN   960
NYTWVRALSA QMGVGGDDSW GQKVHPEFCL DAQKARQLRL VIQPLLLK                1008

SEQ ID NO: 19            moltype = AA  length = 1007
FEATURE                  Location/Qualifiers
source                   1..1007
                         mol_type = protein
                         organism = Lactobacillus delbrueckii
                         note = subspecies lactis
SEQUENCE: 19
MSNKLVKEKR VDQADLAWLT DPEVYEVNTI PPHSDHESFQ SQEELEEGKS SLVQSLDGNW    60
LIDYAENGQG PINFYAEDFD DSNFKSVKVP GNLELQGFGQ PQYVNIQYPW DGSEEIFPPQ   120
VPSKNPLASY VRYFDLDEAL WDKEVSLKFA GAATAIYVWL NGHFVGYGED SFTPSEFMVT   180
KFLKKEGNRL AVALYKYSSA SWLEDQDFWR LSGLFRSVTL EAKPLLHLED LKLTASLTDN   240
YQKGKLEVEA NIAYRLPNAS FKLEVRDSEG DLVAEKVGPI RSEKLDFSLA DLPVAAWSAE   300
KPNLYQVRLY LYQAGSLLEV SRQEVGFRNF ELKDGIMYLN GQRIVFKGVN RHEFDSKLGR   360
AITEADMIWD IKTMKQSNIN AVRCSHYPNQ SLFYRLCDKY GLYVIDEANL ESHGTWEKVG   420
HEDPSFNVPG DDQHWLGASL SRVKNMMARD KNHASILIWS LGNESYAGTV FAQMADYVRK   480
ADPTRVQHYE GVTHNRKFDD ATQIESRMYA PAKEIEEYLT KKPAKPFISV EYAHAMGNSV   540
GDLAAYTALE KYPHYQGGFI WDWIDQGLEK DGHLLYGGDF DDRPTDYEFC GDGLVFADRT   600
TSPKLANVKA LYSNLKLEVK DGQLFIKNDL LFTNSSAYYF LTSLLVDGKL TYQSQPLTFG   660
LEPGESGTFA LPWPEVEDEK GEIVYQVTAH LKEDLPWADE GFTVAEAEEA VTKLPEFYPA   720
GRPELVDSDF NLGLKGNGFR ILFSKAKGWP VSIKYAGREY LKRLPEFTFW RALTDNDRGA   780
GYGYDLAKWE NAGKYARLQD ISYEIKENSA LVKTAFTLPV ALKGDLTITY EVDSLGKIAV   840
TANFPGAVEN GLLPAFGLNF ALPKELSDYR YYGLGPNESY ADRLEGSYLG IYQGMVEKNF   900
```

```
TPYLRPQEAG NRSKVRYYQL FDEEGGLEFT ANGADLNLSA LPYSAAQIEA ADHAFELTNN    960
YTWVRALAAQ MGVGGDDSWG QKVHPEFCLD AQEARQLKLV IQPLLLK                 1007

SEQ ID NO: 20              moltype = AA  length = 628
FEATURE                    Location/Qualifiers
source                     1..628
                           mol_type = protein
                           organism = Lactobacillus helveticus
SEQUENCE: 20
MQANINWLDN PEVFRVNQLP AHSDHPFFRD YREWQKQHSS YQQSLNGKWK FHFSANPMDR     60
PQDFYQRDFD SSNFDSIPVP SEIELSNYTQ NQYINVLFPW EGKIFRRPAY ALDPNDHEEG    120
SFSKGADNTV GSYLKRFDLS SALIGKDVHI KFEGVEQAMY VWLNGHFVGY AEDSFTPSEF    180
DLTPYIQDKD NLLAVEVFKH STASWLEDQD MFRFSGIFRS VELLGIPATH LMDMDLKPRV    240
ADNYQDGIFN LKLHFIGKKA GSFHLLVKDI KGHTLLEKNE DIKENVQINN EKFENVHLWN    300
NHDPYLYQLL IEVYDEQQNL LELIPFQFGF RRIEISPEKV VLLNGKRLII NGVNRHEWDA    360
KRGRSITMSD MTTDINTFKE NNINAVRTCH YPNQIPWYYL CDQNGIYVMA ENNLESHGTW    420
QKMGEIEPSD NVPGSIPQWK EAVIDRARNN YETFKNHTSI LFWSLGNESY AGDNIIAMNE    480
FYKSHDDTRL VHYEGVVHRE ELKDKISDVE SCMYLPPKKV EEYLQNDPPK PFMEDCEYMHD   540
MGNSDGGMGS YIKLLDKYPQ YFGGFIWDFI DQALLVHDEI SGHDVLRYGG DFDDRHSDYE    600
FSGDGLMFAD RTPKPAMQEV RYYYGLHK                                      628

SEQ ID NO: 21              moltype = AA  length = 318
FEATURE                    Location/Qualifiers
source                     1..318
                           mol_type = protein
                           organism = Lactobacillus helveticus
SEQUENCE: 21
MDYTNNQLHI IYGDATFGVN GKDFQYIFSY ERGGLESLKV HGKEWLYRVP TPTFWRATTD     60
NDRGSGFNLK AAQWLGADMF TKCTDIHLKV DRHDFAELPI APFNNKFSNH EYAKSAEISF    120
TYQTLTTPAT NAKIIYNIDD VGHIKVTMRY YGKKGLPPLP VIGIRLIMPT AATGFDYEGL    180
SGETYPDRMA GAKEGKFHID GLPVTEYLVP QENGMHMQTK KLTINRETTQ NNVDRTNEKF    240
SLSIQQAEKP FNFSCLPYTA EELENATHIE ELPLVRRTVL VIAGAVRGVG GIDSWGTDVE    300
SAYHINPELD HEFSFILN                                                 318

SEQ ID NO: 22              moltype = AA  length = 1023
FEATURE                    Location/Qualifiers
source                     1..1023
                           mol_type = protein
                           organism = Bifidobacterium longum
SEQUENCE: 22
MTDVTHVDRA SQAWLTDPTV FEVNRTPAHS SHKWYARDPQ SGQWSDLKQS LDGEWRVEVV     60
QAADINLEEE PATAESFDDS SFERIQVPGH LQTAGLMNHK YVNVQYPWDG HENPLEPNIP    120
ENNHVALYRR KFTVSAPVAN AKQAGGSVSI VFHGMATAIY VWVNGAFVGY GEDGFTPNEF    180
DITELLHDGE NVVAVACYEY SSASWLEDQD FWRLHGLFRS VELAARPHVH IENTQIEADW    240
DPEAGTASLD AALTVLNAAD AATVRATLKD ADGNTVWQTT GDAEAQTAIS SGPLQGIAPW    300
SAESPTLYEL DVDVIDQAGD VIECTSQKVG FRRFRIEDGI LTINGKRIVF KGADRHEFDA    360
EQGRAITEQD MIDDRVVFCKR HNINISRTSH YPNQERWYEL CDEYGIYLID EANLEAHGSW    420
SLPGDVLTED TIVPGSKREW EGACVDRVNS MMRRRDYNHPS VLIWSLGNES YVGDVFRAMY    480
KHVHDIDPNR PVHYEGVTHN RDYDDVTDIE TRMYSHADEI EKYLKDDPKK PYLSCEYMHA    540
MGNSVGNMDE YTALERYPKY QGGFIWDFID QAIYATQPDG TRSLRYGGDF GDRPSDYEFS    600
GDGLLFANRK PSPKAQEVKQ LYSNVHIDVT KDSVSVKNDL LFTATGDYVF VLSVLADGKP    660
VWQSTRRFDV PAGETRTFDV AWPVAAYRAD ARELVLQVSQ RLAKATDWAE SGYELAFGQT    720
VVPADATATP DTKPADGTIT VGRWNAGVRG AGREVLLSRT QGGMVSYTFA GNEFVLRRPA    780
ITTFRPLTDN DRGAGHGFER VQWLGAGRYA RCVDNVLEQI DDSTLKGTYT YELATAQRTK    840
VTVSYTAHTD GRVNLHVEYP GEQGDLPTIP AFGIEWTLPV QYTNLRFFGT GPAETYLDRK    900
HAKLGVWSTN AFADAHAPYLM PQETGNHEDV RWAEITDDHG HGMRVSRADG AAPFAVSLLP    960
YSSFMLEEAQ HQDELPKPKH MFLRVLAAQM GVGGDDSWMS PVHPQYHIPA DKPISLDVDL   1020
ELI                                                                 1023

SEQ ID NO: 23              moltype = AA  length = 628
FEATURE                    Location/Qualifiers
source                     1..628
                           mol_type = protein
                           organism = Lactobacillus reuteri
SEQUENCE: 23
MDADIKWLDE PETFRVNQLP AHSDHYYYGN YDEWRHNNSR FAQNLDGQWQ FNFAENLRER     60
ENDFYKMDYD SSSFGTIEVP SEIELNNYAQ NNYINTLIPW EGKIYRRPAY TLSPDDAQEG    120
SFSDGDDNTI GEYLKHFDLD PSLRGKQVRI RFDGVERAMY VWLNGHFIGY AEDSFTPSEF    180
DLTPYIQDEG NVLAVEVFKH STASWIEDQD MFRFSGIFRS VNLLAQPLVH VEDLNIRPIV    240
TDNYQDGIFN VELQLHGEKT GNVNVRVIDN DGNTLVNETH PVDSTVKVQD QFLENVHLWD    300
NHDPYLYQLL IEIRDDEGNL VELVPYRFGF RRIEINKDHV VLLNGQRLII NGVNRHEWDA    360
RRGRAITMDD MTSDIHTFKE NNINAVRTCH YPDQIPWYYL CDDNGIYMMA ENNLESHATW    420
QKMGAIEPSY NVPGSVPQWR DVVVDRARTN YETFKNHPSI LFWSLGNESY AGDNIVKMNE    480
FYKKHDDSRL VHYEGVCHTP EYRDRISDVE SWMYLPPKEV EEYLKNNPDK PFMECEYMHD    540
MGNSDGGMGS YISLLDKYPQ YFGGFIWDFI DQALLVKDPV SGQEVMRYGG DFDDRHSDYE    600
FSGDGLMFAD RTPKPAMQEV RYYYGLHK                                      628

SEQ ID NO: 24              moltype = AA  length = 319
FEATURE                    Location/Qualifiers
```

```
source                      1..319
                            mol_type = protein
                            organism = Lactobacillus reuteri
SEQUENCE: 24
MAYTNKLRVI YGDATLGLSG DGFHYIFSYE RGGLESLKLN GKEWLYREPM PTFWRATTDN    60
DRGSGFNIRS AQWLAADTFH KCVGIDLTVD NQHFAELPIA PITNEFSDPV SAESVKIKYT   120
FATLTVPATQ VTVIYEVNGQ GEIKVTMHYY GHEDLPGLPV VGMRFIMPTV ATGFDYQGLS   180
GETYPDRMAG ATEGTFHVDG LPVTKYLVPQ ENGMHMATHA LTITRDSTQN NADHSREPFS   240
LTVKQDAQPF AFSCLPYTAE ELENATHIEE LPLARRTVLV VAGAVRGVGG IDSWGADVEE   300
QYHIPADRDV EFSFVLNAK                                                319

SEQ ID NO: 25               moltype = AA  length = 1007
FEATURE                     Location/Qualifiers
source                      1..1007
                            mol_type = protein
                            organism = Lactobacillus delbrueckii
                            note = subspecies lactis
SEQUENCE: 25
MSNKLVKEKR VDQADLAWLT DPEVYEVNTI PPHSDHESFQ SQEELEEGKS SLVQSLDGNW    60
LIDYAENGQG PINFYAEDFD DSNFKSVKVP GNLELQGFGQ PQYVNIQYPW DGSEEIFPPQ   120
VPSKIPLASY VRYFDLDEAL WDKEVSLKFA GAATAIYVWL NGHFVGYGED SFTPSEFMVT   180
KFLKKEGNRL AVALYKYSSA SWLEDQDFWR LSGLFRSVTL EAKPLLHLED LKLTASLTDN   240
YQKGKLEVEA NIAYRLPNAS FKLEVRDSEG DLVAEKVGPI RSEKLDFSLA DLPVAAWSAE   300
KPNLYQVRLY LYQAGSLLEV SRQEVGFRNF ELKDGIMYLN GQRIVFKGVN RHEFDSKLGR   360
AITEADMIWD IKTMKQSNIN AVRCSHYPNQ SLFYRLCDKY GLYVIDEANL ESHGTWEKVG   420
HEDPSFNVPG DDQHWLGASL SRVKNMMARD KNHASILIWS LGNESYAGTV FAQMADYVRK   480
ADPTRVQHYE GVTHNRKFDD ATQIESRMYA PAKEIEEYLT KKPAKPFISV EYAHAMGNSV   540
GDLAAYTALE KYPHYQGGFI WDWIDQGLEK DGHLLYGGDF DDRPTDYEFC GDGLVFADRT   600
TSPKLANVKA LYSNLKLEVK DGQLFIKNDN LFTNSSAYYF LTSLLVDGKL TYQSQPLTFG   660
LEPGESGTFA LPWPEVEDEK GEIVYQVTAH LKEDLPWADE GFTVAEAEEA VTKLPEFYPA   720
GRPELVDSDF NLGLKGNGFR ILFSKAKGWP VSIKYAGREY LKRLPEFTFW RALTDNDRGA   780
GYGYDLAKWE NAGKYARLQD ISYEIKENSA LVKTTFTLPV ALKGDLTITY EVDSLGKIAV   840
TANFPGAVEN GLLPAFGLNF ALPKELSDYR YYGLGPNESY ADRLEGSYLG IYQGMVEKNF   900
TPYLRPQEAG NRSKVRYYQL FDEEGGLEFT ANGADLNLSA LPYSAAQIEA ADHAFELTNN   960
YTWVRALAAQ MGVGGDDSWG QKVHPEFCLD AQEARQLKLV IQPLLLK                1007

SEQ ID NO: 26               moltype = AA  length = 628
FEATURE                     Location/Qualifiers
source                      1..628
                            mol_type = protein
                            organism = Lactobacillus helveticus
SEQUENCE: 26
MQANINWLDN PEVFRVNQLP AHSDHPFFRD YREWQKQHSS YQQSLNGKWK FHFSANPMDR    60
PQDFYQRDFD SSNFDSIPVP SEIELSNYTQ NQYINVLFPW EGKIFRRPAY ALDPNDHEEG   120
SFSKGADNTV GSYLKRFDLS SALIGKDVHI KFEGVEQAMY VWLNGHFVGY AEDSFTPSEF   180
DLTPYIQEKD NLLAVEVFKH STASWLEDQD MFRFSGIFRS VELLGIPATH LMDMDLKPRV   240
ADNYQDGIFN LKLHFIGKKA GSFHLLVKDI KGHTLLEKNE DIKENVQINN EKFENVHLWN   300
NHDPYLYQLL IEVYDEQQNL LELIPFQFGF RRIEISPEKV VLLNGKRLII NGVNRHEWDA   360
KRGRSITMSD MTTDINTFKE NNINAVRTCH YPNQIPWYYL CDQNGIYVMA ENNLESHGTW   420
QKMGEIEPSD NVPGSIPQWK EAVIDRARNN YETFKNHTSI LFWSLGNESY AGDNIIAMNE   480
FYKSHDDTRL VHYEGVVHRP ELKDKISDVE SCMYLPPKKV EEYLQNDPPK PFMECEYMHD   540
MGNSNGGMDS YIKLLDKYPQ YFGGFIWDFI DQALLVHDEI SGHDVLRYGG DFDDRHSDYE   600
FSGDGLMFAD RKPKPAMQEV RYYYGLHK                                      628

SEQ ID NO: 27               moltype = AA  length = 318
FEATURE                     Location/Qualifiers
source                      1..318
                            mol_type = protein
                            organism = Lactobacillus helveticus
SEQUENCE: 27
MDYTNNQLHI IYGDATFGVN GKDFQYIFSY ERGGLESLKV HGKEWLYRVP TPTFWRATTD    60
NDRGSGFNLK AAQWLGADMF TKCTDIHLKV DRHDFAELPI APFNNKFSNH EYAKSAEISF   120
TYQTLTTPAT NAKIIYNIDD GGHIKVTMRY YGKKGLPPLP VIGIRLIMPT AATGFDYEGL   180
SGETYPDRMA GAKEGKFHID GLPVTEYLVP QENGMHMQTK KLTINRETTQ NNVDRTNEKF   240
SLSIQQAEKP FNFSCLPYTA EELENATHIE ELPLVRRTVL VIAGAVRGVG GIDSWGTDVE   300
SAYHINPDLD HEFSFILN                                                 318

SEQ ID NO: 28               moltype = AA  length = 626
FEATURE                     Location/Qualifiers
source                      1..626
                            mol_type = protein
                            organism = Lactobacillus crispatus
SEQUENCE: 28
MKANIKWLDD PEVFRINQLP AHSDHPFYKD YREWQKHSSS FKQSLNGAWQ FHFSKDPQSR    60
PIDFYKLSFD SSSFDTIPVP SEIELNGYAQ NQYTNILYPW ESKIYRKPAY TLGRGIKDGD   120
FSQGKDNTVG SYLKHFDLNP ALAGHDIHIQ FEGVERAMYV YLNGHFIGYA EDSFTPSEFD   180
LTPYIQAKDN ILAVEVFKHS TASWLEDQDM FRFSGIFRSV ELLALPRTHL MDLDIKPTVV   240
NDYHDGVFNA KLHFMGKTSG NVHVLIEDID GKTLLNKKLP LKSTVEIENE TFANVHLWDN   300
HDPYLYQLII EVYDQDGKLV ELIPYQFGFR KIEITKDHVV LLNGKRLIIN GVNRHEWDAK   360
```

```
RGRSITLADM KQDIATFKHN NINAVRTCHY PNQIPWYYLC DQNGIYMMAE NNLESHGTWQ      420
KLGQVEATSN VPGSIPEWRE VVVDRARSNY ETFKNHTAIL FWSLGNESYA GSNIAAMNKL      480
YKDHDSSRLT HYEGVFHAPE FKKEISDLES CMYLPPKEAE EYLQNPKKPL VECEYMHDMG      540
NSDGGIGSYI KLIDKYPQYM GGFIWDFIDQ ALLVHDPVSG QDVLRYGGDF DDRHSDYEFS      600
GDGLMFADRT PKPAMQEVRY YYGLHK                                           626

SEQ ID NO: 29           moltype = AA   length = 316
FEATURE                 Location/Qualifiers
source                  1..316
                        mol_type = protein
                        organism = Lactobacillus crispatus
SEQUENCE: 29
MAYTNNLHVV YGEASLGVNG QDFAYLFSYE RGVLESLKIK DKEWLYRTPT PTFWRATTDN       60
DRGSGFNQKA AQWLGADMFT KCVGIHVQVD DHQFDELPIA PINNQFSNQE FAHEVKVAFD      120
YETLTTPATK VKIIYNINDA GHMTITMHYF GKKGLPPLPV IGMRFIMPTK AKSFDYTGLS      180
GETYPDRMAG AERGTFHIDG LPVTKYLVPQ ENGMHMQTNE LVITRNSTQN NADKDGDFSL      240
KITQTKQPFN FSLLPYTAEE LENATHIEEL PLARRSVLVI AGAVRGVGGI DSWGSDVEEQ      300
YHIDPEQDHE FSFTLN                                                     316

SEQ ID NO: 30           moltype = AA   length = 1025
FEATURE                 Location/Qualifiers
source                  1..1025
                        mol_type = protein
                        organism = Streptococcus thermophilus
SEQUENCE: 30
MNMTKIQTYL NDPKIVSVNT VDAHSDHKYF ESLEEFSEGE MKLRQSLNGK WKIHYAQNTN       60
QVLKDFYKTE FDETDLNFIN VPGHLELQGF GSPQYVNTQY PWDGKEFLRP PQVPQESNAV      120
ASYVKHFTLN DALKDKKVFI SFQGVATSIF VWVNGNFVGY SEDSFTPSEF EISDYLVEGD      180
NKLAVAVYRY STASWLEDQD FWRLYGIFRD VYLYAIPKVH VQDLFVKGDY DYQTKAGQLD      240
IDLKTVGDYE DKKIKYVLSD YEGIVTEGDA SVNGDGELSV SLENLKIKPW SAESPKLYDL      300
ILHVLDDDQV VEVVPVKVGF RRFEIKDKLM LLNGKRIVFK GVNRHEFNAR TGRCITEEDM      360
LWDIKVMKQH NINAVRTSHY PNQTRWYELC DEYGLYVIDE ANLETHGTWQ KLGLCEPSWN      420
IPASEPEWLP ACLDRANNMF QRDKNHASVI IWSCGNESYA GKDIADMADY FRSVDNTRPV      480
HYEGVAWCRE FDYITDIESR MYAKPADIEE YLTTGKLDKL SSVSDKHFAS GNLTNKPQKY      540
YISCEYMHTM GNSGGGLQLY TDLEKYPEYQ GGFIWDFIDQ AIYKTLPNGS EFLSYGGDWH      600
DRPSDYEFCG NGIVFADRTL TPKLQTVKHL YSNIKIAVDE KSVTIKNDNL FEDLSAYTFL      660
ARVYEDGRKV SESEYHFDVK PGEEATFPVN FVVEASNSEQ IYEVACVLRE ATKWAPKGHE      720
IVRGGYVVEK ISTETPVKAP LNVVEGDFNI GIQGQNFSIL LSRAQNTLVS AKYNGVEFIE      780
KGPKLSFTRA YTDNDRGAGY PFEMAGWKVA GNYSKVTDTQ IQIEDDSVKV TYVHELPGLS      840
DVEVKVTYQV DYKGRIFVTA NYDGKAGLPN FPEFGLEFAI GSQFTNLSYY GYGAEESYRD      900
KLPGAYLGRY ETSVEKTFAP YLMPQESGNH YGTREFTVSD DNHNGLKFTA LNKAFEFSAL      960
RNSTEQIENA RHQYELQESD ATWIKVLAAQ MGVGGDDSWG APVHDEFLLS SADSYQLSFM     1020
IEPLN                                                                1025

SEQ ID NO: 31           moltype = AA   length = 1008
FEATURE                 Location/Qualifiers
source                  1..1008
                        mol_type = protein
                        organism = Lactobacillus delbrueckii
                        note = subspecies indicus
SEQUENCE: 31
MNNKLAQVKR VDQADLAWLT DPEIYEVNTI PPHSDHESFQ SLEELEEGKS SLVQSLDGDW       60
LIDYAENGEG PANFYEENFD DSSFKSVKVP GNLELQGFGQ PQYVNVQYPW DGSDEIFPPM      120
IPSKNPVASY VRYFDLEEAF WDKEVSLKFA GAATAIYVWL NGHFVGYGED SFTPSEFMVT      180
KFLLKKEGNRL AVALYKYSSA SWLEDQDFWR MSGLFRSVTL EAKPLLHLQD LKLTASLTND      240
YQKGSLQVEA DIDYRLPNSS FKLELRDSAG ELVAEKVGPI RSEKLDFSLA DLPVAAWSAE      300
EPNLYQVRLS LYQQGSLLEV SRQEVGFRNF ELKDGIMYLN GKRIVFKGVN RHEFDSKLGR      360
AITEADMIWD IKTMKQSNIN AVRCSHYPNQ SIFYHLCDKY GLYVIDEANL ESHGTWEKVG      420
GHEDPSFNVP GDDQRWLGAS LSRVKNMMAR DKNHASILIW DKGNESYAGK VFAQMADYVR      480
QADPTRVQHY EGVTHNRKFD DATQIESRMY APAKEIEEYL TKKPAKPFVS CEYAHAMGNS      540
VGDLAAYTAL EKYPHYQGGF IWDWIDQGLE KEGHLLYGGD FDDRPSDYEF CGDGLVFADR      600
TTSPKLANVK ALYSNLKLEL KDGQLFLKND NLFTNSSAYY FLTSLLVDGK LTYQSQPLTF      660
ALEPGESGTF ALPWPEVEDE KGEIVYQVTA HLKEDLPWAD EGFTVAEAEE AVTKLPEFYP      720
AGRPELVDSD YNLGIKGNGF RILFSKAKGW PVSIKYAGRE YLKRLPEFTF WRALTDNDRG      780
AGYGYDLAKW ENAGKYARLQ DISYEIKENS VLVKTAFTLP VALKGDLTIT YEVDSLGKIA      840
VTANFPGAVE NGLLPAFGLN FALPKELSDY RYYGLGPNES YADRLEGSYL GIYQGAVEKN      900
FTPYLRPQEV GNRSKVRYYQ LFDEEGGLEF TANGANLNLS ALPYSAAQIE AADHAFELTN      960
NYTWVRALAA QMGVGGDDSW GQKVHPEFCL DAQEARQLKL VIQPLFTE                  1008

SEQ ID NO: 32           moltype = AA   length = 1049
FEATURE                 Location/Qualifiers
source                  1..1049
                        mol_type = protein
                        organism = Bifidobacterium adolescentis
SEQUENCE: 32
MADTAELAIV HATTASASWL TDPTVFAANR KPAHSSHRYV IGETSEPKQS LDGEWKVRIE       60
QARNVDVESA PFAAVDFEDG DFGAIEVPGH LQMAGYLKNK YVNIQYPWDG HEDPQAPNIP      120
ENNHVAIYRR RFALDAQLAR TLENDGTVSL TFHGAATAIY VWLDGTFVGY GEDGFTPSEF      180
DVTEALRNGN GNAADSPEAE HTLTVACYEY SSASWLEDQD FWRLHGLFRT VELAAQPHTH      240
```

```
VETVQLEADY TAADTAGTAD TAELNAALTL RNPADAMTIE STLRDGDGNV VWESTQACNG   300
EIALNSGKMT NIAPWSAESP TLYTLTVRVV GHDGAIIETV TQKIGFRTFR IENGIMTLNG   360
KRIVFKGADR HEFDAKRGRA ITREDMLSDV VFCKRHNINA IRTSHYPNQE YWYDLCDEYG   420
LYLIDETNME THGTWVANNV ERPEDGIPGS RPEWEDACVD RINSMMRRDY NHPSVLIWSL   480
GNESSAGEVF RAMYRHAHTI DPNRPVHYEG SVHMREFDTV TDIESRMYAH ADEIERYLND   540
GSPAHTDGPK KPYISCEYMH AMGNSCGNMD EYTALERYPM YQGGFIWDFI DQAIETKLPD   600
GTTRMCYGGD FGDRPSDYEF SGDGLLFADR TPSPKAQEVK QLYANVKIAV SVDEARITND   660
NLFVSTGDYR FVLRILADGK PVWSTTRRFD VAAGESASFE VDWPVDDYRS NAEELVLEVS   720
QQLGNACDWA PAGYELAFGQ CVVAGAKTTA DAVDAAGAPA DGTVTLGRWN AGVRGQGREA   780
LFSRTQGGMV SYTFGEREFV LRRPSITTFR PLTDNDRGAG HAFERAAWAV AGKYARCVDC   840
AIANRGENAV EATYTYELAI PQRTKVTVRY VADTAGLVSL DVEYPGEKNG DLPTIPAFGI   900
EWALPVEYAN LRFYGAGPEE TYADRRHAKL GVWSTTAGDD CAPYLLPQET GNHEDVRWAE   960
ITDDSGHGVR VKRGAGAKPF AMSLLPYSST MLEEALHQDE LPKPRHMFLR LLAAQMGVGG  1020
DDSWMSPVHE QYQLPADQPL SLNVQLKLF                                   1049

SEQ ID NO: 33           moltype = AA   length = 1023
FEATURE                 Location/Qualifiers
source                  1..1023
                        mol_type = protein
                        organism = Bifidobacterium adolescentis
SEQUENCE: 33
MANETRIEHA SETWLADSTV FEVNRVPAHS DHKCYAHDSQ TNEWSDLRQS LDGEWRVEVV    60
QASDIEFNEE PFVRENFDDS AFERIQVPGH LQMAGLMNNK YVNIQYPWDG HENPAEPNIP   120
ENNHVALYRK TFTMANRLAD TKNAGGTVSI VFHGMATAIY VWVNGMFVGY GEDGFTPNEF   180
DITEMLHDGE NVVAVACYEY SSASWLEDQD FWRLHGLFRS VELAAQPHVH IENMQIESDW   240
DPESGSASLD AALTVRNAAD AATISATLKD SDGNVVWETA NCADPDTSIS TGSLNGIRPW   300
SAEDPVLYEF EVTVIDHAGN IAEVAVQKVG FRRFRIEDGI MTINGKRIVF KGADRHEFDP   360
KRGRAITEQD MIDDVVFCKR HNLNAIRTSH YPNQERWYEL CDEYGIYLID ETNLETHGSW   420
CLPGDVLTEE TAVPGSKAHW EGACVDRVNS MVRRDYNHPS VLIWSLGNES YTGDVFRAMY   480
KRVHDIDPNR PVHYEGVTHN RDYNDVTDIE TRMYAHADAI EEYLKNDPQK PYISCEYMHA   540
MGNSCGNMDE YTALERYPKY QGGFIWDFID QAIYATQPDG TTSLRYGGDF GDRPSDYEFS   600
GNGLVFADRK PTPKAQEVKQ LYSNVHIDVA EDSVTIKNDN LFTSTGEYTF VLRVLADGEP   660
VWQSERRFDV PAGSTEKLDV DWPLDLYRDG ASELVLEVSQ RLAKATNWAV AGYELAFGQT   720
VVAGSKKASA PVKPVDGIVT VGRWNVGVQG SGREVLLSRT QGGLVSYTFN NREFVLRRPA   780
VTTFRALTDN DRGAGHGFER AQWLGAGRYA RCIGNEIEQI DENTVKASYT YELATPQRTK   840
VTVSYTADTT GRVNLHVEYP GEPGDLPTIP AFGIEWTLPV QYSNLRFFGA GPEETYQDRK   900
HAKLGVWSTD AFKDHAPYLM PQETGNHEDV RWAEITDEKG HGLRISRAEG AEPFAMSLQP   960
YSSFMLEEAQ HQDELPAPKH MFLRVLAEQM GVGGDDSWMS PVHPQYHIPA DQPISLDVDL  1020
DLI                                                               1023

SEQ ID NO: 34           moltype = AA   length = 1305
FEATURE                 Location/Qualifiers
source                  1..1305
                        mol_type = protein
                        organism = Bifidobacterium bifidum
SEQUENCE: 34
MVEDATRSDS TTQMSSTPEV VYSSAVDSKQ NRTSDFDANW KFMLSDSVQA QDPAFDDSAW    60
QQVDLPHDYS ITQKYSQSNE AESAYLPGGT GWYRKSFTID RDLAGKRIAI NFDGVYMNAT   120
VWFNGVKLGT HPYGYSPFSF DLTGNAKFGG ENTIVVKVEN RLPSSRWYSG SGIYRDVTLT   180
VTDGVHVGNN GVAIKTPSLA TQNGGNVTMN LTTKVANDTE AAANITLKQT VFPKGGKTDA   240
AIGTVTTASK SIAAGASADV TSTITAASPK LWSIKNPNLY TVRTEVLNGD TVLDTYDTEY   300
GFRWTGFDAT SGFSLNGEKV KLKGVSMHHD QGSLGAVANR RAIERQVEIL QKMGVNSIRT   360
THNPAAKALI DVCNEKGVLV VEEVFDMWNR SKNGNTEDYG KWFGQTIAGD NAVLGGDKDE   420
TWAKFDLTST INRDRNAPSV IMWSLGNEMM EGISGSVSDF PATSAKLVAW TKAADSTRPM   480
TYGDNKIKAN WNESNTMGDN LTANGGVVGT NYSDGANYFK IRTTHPSWAI YGSETASAIN   540
SRGIYNRTTG GAQSSDKQLT SYDNSAVGWG AVASSAWYDV VQRDFVAGTY VWTGFDYLGE   600
PTPWNGTGSG AVGSWPSPKN SYFGIVDTAG FPKDTYYFYQ SQWNDDVHTL HILPAWNENV   660
VAKGSGNKVP VVVYTDAAKV KLYFTPKGST EKRLIGEKSF TKKTTAAGYT YQVYEGTDKD   720
STAHKNMYLT WNVPWAEGTI SAEAYDENNR LIPEGSTEGN ASVTTTGKAA KLKADADRKT   780
ITADGKDLSY IEVDVTDANG HIVPDAANRV TFDVKGAGKL VGVDNGSSPD HDSYQADNRK   840
AFSGKVLAIV QSTKEAGEIT VTAKADGLQS STVKIATTAV PGTSTEKTVR SFYYSRNYYV   900
KTGNKPILPS DVEVRYSDGT SDRQNVTWDA VSDDQIAKAG SFSVAGTVAG QKISVRVTMI   960
DEIGALLNYS ASTPVGTPAV LPGSRPAVLP DGTVTSANFA VHWTKPADTV YNTAGTVKVP  1020
GTATVFGKEF KVTATIRVQR SQVTIGSSVS GNALRLTQNI PADKQSDTLD AIKDGSTTVD  1080
ANTGGGANPS AWTNWAYSKA GHNTAEITFE YATEQQLGQI VMYFFRDSNA VRFPDAGKTK  1140
IQISADGKNW TDLAATETIA AQESSDRVKP YTYDFAPVGA TFVKVTVTNA DTTTPSGVVC  1200
AGLTEIELKT ATSKFVTNTS AALSSLTVNG TKVSDSVLAA GSYNTPAIIA DVKAEGEGNA  1260
SVTVLPAHDN VIRVITESED HVTRKTFTIN LGTEQEFPAD SDERD                  1305

SEQ ID NO: 35           moltype = AA   length = 1025
FEATURE                 Location/Qualifiers
source                  1..1025
                        mol_type = protein
                        organism = Kluyveromyces lactis
SEQUENCE: 35
MSCLIPENLR NPKKVHENRL PTRAYYYDQD IFESLNGPWA FALFDAPLDA PDAKNLDWET    60
AKKWSTISVP SHWELQEDWK YGKPIYTNVQ YPIPIDIPNP PTVNPTGVYA RTFELDSKSI   120
ESFEHRLRFE GVDNCYELYV NGQYVGFNKG SRNGAEFDIQ KYVSEGENLV VVKVFKWSDS   180
TYIEDQDQWW LSGIYRDVSL LKLPKKAHIE DVRVTTTFVD SQYQDAELSV KVDVQGSSYD   240
```

```
HINFTLYEPE DGSKVYDASS LLNEENGNTT FSTKEFISFS TKKNEETAFK INVKAPEHWT    300
AENPTLYKYQ LDLIGSDGSV IQSIKHHVGF RQVELKDGNI TVNGKDILFR GVNRHDHHPR    360
FGRAVPLDFV VRDLILMKKF NINAVRNSHY PNHPKVYDLF DKLGFWVIDE ADLETHGVQE    420
PFNRHTNLEA EYPDTKNKLY DVNAHYLSDN PEYEVAYLDR ASQLVLRDVN HPSIIIWSLG    480
NEACYGRNHK AMYKLIKQLD PTRLVHYEGD LNALSADIFS FMYPTFEIME RWRKNHTDEN    540
GKFEKPLILC EYGHAMGNGP GSLKEYQELF YKEKFYQGGF IWEWANHGIE FEDVSTADGK    600
LHKAYAYGGD FKEEVHDGVF IMDGLCNSEH NPTPGLVEYK KVIEPVHIKI AHGSVTITNK    660
HDFITTDHLL FIDKDTGKTI DVPSLKPEES VTIPSDTTYV VAVLKDDAGV LKAGHEIAWG    720
QAELPLKVPD FVTETAEKAA KINDGKRYVS VESSGLHFIL DKLLGKIESL KVKGKEISSK    780
FEGSSITFWR PPTNNDEPRD FKNWKKYNID LMKQNIHGVS VEKGSNGSLA VVTVNSRISP    840
VVFYYGFETV QKYTIFANKI NLNTSMKLTG EYQPPDFPRV GYEFWLGDSY ESFEWLGRGP    900
GESYPDKKES QRFGLYDSKD VEEFVYDYPQ ENGNHTDTHF LNIKFEGAGK LSIFQKEKPF    960
NFKISDEYGV DEAAHACDVK RYGRHYLRLD HAIHGVGSEA CGPAVLDQYR LKAQDFNFEF   1020
DLAFE                                                              1025

SEQ ID NO: 36           moltype = DNA   length = 30
FEATURE                 Location/Qualifiers
source                  1..30
                        mol_type = other DNA
                        organism = synthetic construct
                        note = Primer
modified_base           9
                        mod_base = OTHER
                        note = misc_feature - deoxyuracil
SEQUENCE: 36
attaaccatg cgacgcaact tcgaatggcc                                      30

SEQ ID NO: 37           moltype = DNA   length = 31
FEATURE                 Location/Qualifiers
source                  1..31
                        mol_type = other DNA
                        organism = synthetic construct
                        note = Primer
modified_base           9
                        mod_base = OTHER
                        note = misc_feature - deoxyuracil
SEQUENCE: 37
atcttctctt taccgcctta ccacgagcac g                                    31

SEQ ID NO: 38           moltype = DNA   length = 33
FEATURE                 Location/Qualifiers
source                  1..33
                        mol_type = other DNA
                        organism = synthetic construct
                        note = Primer
modified_base           9
                        mod_base = OTHER
                        note = misc_feature - deoxyuracil
SEQUENCE: 38
agagaagatt ttcagcctga tacagattaa atc                                  33

SEQ ID NO: 39           moltype = DNA   length = 33
FEATURE                 Location/Qualifiers
source                  1..33
                        mol_type = other DNA
                        organism = synthetic construct
                        note = Primer
modified_base           9
                        mod_base = OTHER
                        note = misc_feature - deoxyuracil
SEQUENCE: 39
atggttaatt cctcctgtta gcccaaaaaa cgg                                  33

SEQ ID NO: 40           moltype = DNA   length = 22
FEATURE                 Location/Qualifiers
source                  1..22
                        mol_type = other DNA
                        organism = synthetic construct
                        note = Primer
SEQUENCE: 40
cggcgtcaca ctttgctatg cc                                              22

SEQ ID NO: 41           moltype = DNA   length = 20
FEATURE                 Location/Qualifiers
source                  1..20
                        mol_type = other DNA
                        organism = synthetic construct
                        note = Primer
```

```
SEQUENCE: 41
ccgcgctact gccgccaggc                                              20
```